US007049403B2

(12) United States Patent
Itoh et al.

(10) Patent No.: US 7,049,403 B2
(45) Date of Patent: May 23, 2006

(54) INSULIN/IGF/RELAXIN FAMILY POLYPEPTIDES AND DNAS THEREOF

(75) Inventors: Yasuaki Itoh, Tsuchiura (JP); Nobuhiro Suzuki, Mino (JP); Kazunori Nishi, London (GB); Hideki Kizawa, Tsukuba (JP); Masataka Harada, Tsukuba (JP); Kazuhiro Ogi, Tsukuba (JP)

(73) Assignee: Takeda Pharmaceutical Company Limited, Osaka (JP)

(*) Notice: Subject to any disclaimer, the term of this patent is extended or adjusted under 35 U.S.C. 154(b) by 379 days.

(21) Appl. No.: 10/257,848

(22) PCT Filed: Apr. 20, 2001

(86) PCT No.: PCT/JP01/03399

§ 371 (c)(1),
(2), (4) Date: Oct. 17, 2002

(87) PCT Pub. No.: WO01/81562

PCT Pub. Date: Nov. 1, 2001

(65) Prior Publication Data

US 2003/0158381 A1 Aug. 21, 2003

(30) Foreign Application Priority Data

Apr. 21, 2000 (JP) ............................ 2000-126340
Jul. 3, 2000 (JP) ............................ 2000-205587
Aug. 10, 2000 (JP) ............................ 2000-247962
Dec. 22, 2000 (JP) ............................ 2000-395050

(51) Int. Cl.
*C07K 14/00* (2006.01)
*A01N 37/18* (2006.01)
*A61K 39/00* (2006.01)

(52) U.S. Cl. ...................... 530/350; 530/300; 530/399; 514/2; 514/12; 424/198.1

(58) Field of Classification Search ................ 530/300, 530/350, 399; 514/2, 12; 424/198.1; 435/810
See application file for complete search history.

(56) References Cited

FOREIGN PATENT DOCUMENTS

WO WO 99/15664 A1 4/1999

(Continued)

OTHER PUBLICATIONS

Bullesbach et al., SEQ ID No: 7 sequence alignment result.*

(Continued)

*Primary Examiner*—Jon Weber
*Assistant Examiner*—Rita Mitra
(74) *Attorney, Agent, or Firm*—Elaine M. Ramesh; Mark Chao

(57) ABSTRACT

The present invention relates to (1) a polypeptide containing the same or substantially the same amino acid sequence as the amino acid sequence represented by SEQ ID NO:7 (A chain), (2) a polypeptide containing the same or substantially the same amino acid sequence as the amino acid sequence represented by SEQ ID NO:8 (B chain), (3) a polypeptide wherein the A and B chains are bonded to each other via disulfide bonds (2 chains) or its salt, (4) DNAs encoding the same, etc.

These polypeptides and DNAs encoding the same can be used for the diagnosis, treatment, prevention, etc. for diseases, including abnormalities (e.g., diabetes mellitus, etc.) in metabolic regulation (sugar metabolism, lipid metabolism, etc.) of energy sources such as carbohydrates.

15 Claims, 18 Drawing Sheets

```
ATG GCC AGG TAC ATG CTG CTG CTG CTC CTG GCG GTA TGG GTG CTG ACC GGG GAG   54
Met Ala Arg Tyr Met Leu Leu Leu Leu Leu Ala Val Trp Val Leu Thr Gly Glu   18

CTG TGG CCG GGA GCT GAG GCC CGG GCA GCG CCT TAC GGG GTC AGG CTT TGC GGC  108
Leu Trp Pro Gly Ala Glu Ala Arg Ala Ala Pro Tyr Gly Val Arg Leu Cys Gly   36

CGA GAA TTC ATC CGA GCA GTC ATC TTC ACC TGC GGG GGC TCC CGG TGG AGA CGA  162
Arg Glu Phe Ile Arg Ala Val Ile Phe Thr Cys Gly Gly Ser Arg Trp Arg Arg   54

TCA GAC ATC CTG GCC CAC GAG GCT ATG GGA GAT ACC TTC CCG GAT GCA GAT GCT  216
Ser Asp Ile Leu Ala His Glu Ala Met Gly Asp Thr Phe Pro Asp Ala Asp Ala   72

GAT GAA GAC AGT CTG GCA GGC GAG CTG GAT GAG GCC ATG GGG TCC AGC GAG TGG  270
Asp Glu Asp Ser Leu Ala Gly Glu Leu Asp Glu Ala Met Gly Ser Ser Glu Trp   90

CTG GCC CTG ACC AAG TCA CCC CAG GCC TTT TAC AGG GGG CGA CCC AGC TGG CAA  324
Leu Ala Leu Thr Lys Ser Pro Gln Ala Phe Tyr Arg Gly Arg Pro Ser Trp Gln  108

GGA ACC CCT GGG GTT CTT CGG GGC AGC CGA GAT GTC CTG GCT GGC CTT TCC AGC  378
Gly Thr Pro Gly Val Leu Arg Gly Ser Arg Asp Val Leu Ala Gly Leu Ser Ser  126

AGC TGC TGC AAG TGG GGG TGT AGC AAA AGT GAA ATC AGT AGC CTT TGC TAG      429
Ser Cys Cys Lys Trp Gly Cys Ser Lys Ser Glu Ile Ser Ser Leu Cys ***      142
```

FOREIGN PATENT DOCUMENTS

| | | |
|---|---|---|
| WO | WO 00/21996 A2 | 4/2000 |
| WO | WO 00/32221 A2 | 6/2000 |
| WO | WO 00/47776 A2 | 8/2000 |
| WO | WO 01/68862 A1 | 9/2001 |
| WO | WO 02/22802 A1 | 3/2002 |

OTHER PUBLICATIONS

Bullesbach et al., SEQ ID No: 8 sequence alignment result.*
Bullesbach, et al. "Isolation, purification, and the sequence of relaxin from spiny dogfish (*Squalus acanthias*)" Eur. J. Biochem. 161: 335-341 (1986).
Gowan, et al., On the Primary and Tertiary Structure of Relaxin from The Sand Tiger Shark (*Odontaspis taurus*) Febs Letters 129(1): 80-82(Jun. 1981).
Haley, et al., "Porcine Relaxin—Gene Structure and Expression" The Journal of Biological Chemistry 262(25):11940-11946 (1987).
James, et al., "Primary structure of porcine relaxin: homology with insulin and related growth factors" NATURE 267:544-546 (Jun. 9, 1977).
Berger, et al. "Stastical Approach for Evolutionary Relationship of $\alpha$-Conotoxins and Members of Insulin-Superfamily" Horm. Metab. Res. 28:535-540(1996).
Daniele Bani "Relaxin: A Pleiotropic Hormone" Gen. Pharmac. 28(1): 13-22 (1997).
Büllesbach, et al. "The Relaxin-Like Factor Is a Hormone" ENDOCRINE 10(2): 167-169 (Apr. 1999).
XP-002282992, Jan. 27, 2000, EMBL:AC022098.

* cited by examiner

FIG. 1

ATG GCC AGG TAC ATG CTG CTG CTG CTC CTG GCG GTA TGG GTG CTG ACC GGG GAG 54
Met Ala Arg Tyr Met Leu Leu Leu Leu Leu Ala Val Trp Val Leu Thr Gly Glu 18

CTG TGG CCG GGA GCT GAG GCC CGG GCA GCG CCT TAC GGG GTC AGG CTT TGC GGC 108
Leu Trp Pro Gly Ala Glu Ala Arg Ala Ala Pro Tyr Gly Val Arg Leu Cys Gly 36

CGA GAA TTC ATC CGA GCA GTC ATC TTC ACC TGC GGG GGC TCC CGG TGG AGA CGA 162
Arg Glu Phe Ile Arg Ala Val Ile Phe Thr Cys Gly Gly Ser Arg Trp Arg Arg 54

TCA GAC ATC CTG GCC CAC GAG GCT ATG GGA GAT ACC TTC CCG GAT GCA GAT GCT 216
Ser Asp Ile Leu Ala His Glu Ala Met Gly Asp Thr Phe Pro Asp Ala Asp Ala 72

GAT GAA GAC AGT CTG GCA GGC GAG CTG GAT GAG GCC ATG GGG TCC AGC GAG TGG 270
Asp Glu Asp Ser Leu Ala Gly Glu Leu Asp Glu Ala Met Gly Ser Ser Glu Trp 90

CTG GCC CTG ACC AAG TCA CCC CAG GCC TTT TAC AGG GGG CGA CCC AGC TGG CAA 324
Leu Ala Leu Thr Lys Ser Pro Gln Ala Phe Tyr Arg Gly Arg Pro Ser Trp Gln 108

GGA ACC CCT GGG GTT CTT CGG GGC AGC CGA GAT GTC CTG GCT GGC CTT TCC AGC 378
Gly Thr Pro Gly Val Leu Arg Gly Ser Arg Asp Val Leu Ala Gly Leu Ser Ser 126

AGC TGC TGC AAG TGG GGG TGT AGC AAA AGT GAA ATC AGT AGC CTT TGC TAG 429
Ser Cys Cys Lys Trp Gly Cys Ser Lys Ser Glu Ile Ser Ser Leu Cys *** 142

FIG. 2
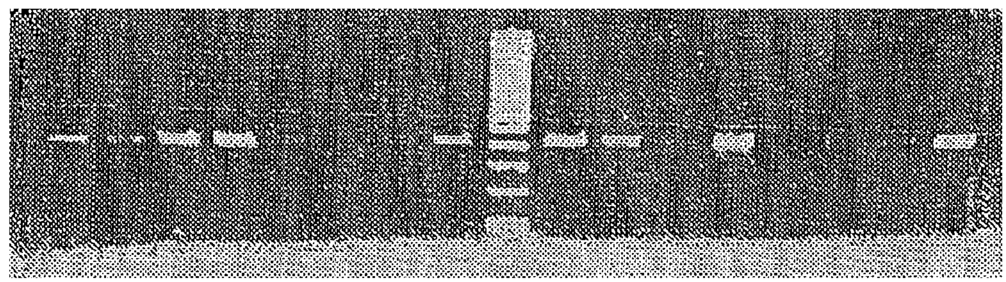
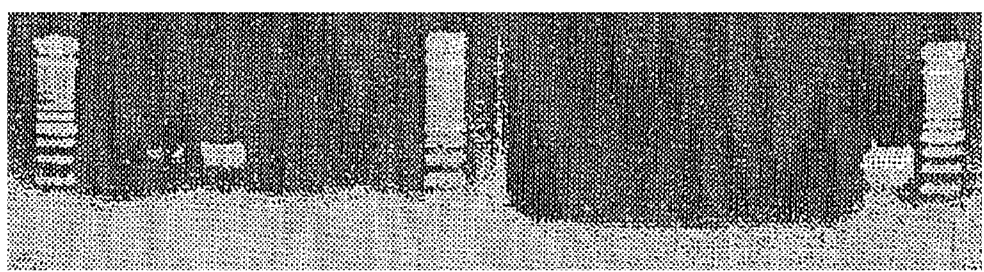

FIG. 3

```
Human.pro       M A - R Y M L L L L L A V W V L T G E L W P G A E A R A A   28
Mouse.pro       M A M L G - - L L L L A S W A L L G A L G L Q A E A R P A   27
Rat.pro         M A T R G - - L L L - A S W A L L G A L V L Q A E A R P A   26
Porcine.PRO     M A K R P L L L L L L A V W V L A G E L W L R T E A R A S   29

Human.pro       P Y G V R L C G R E F I R A V I F T C G G S R W R R S D I   57
Mouse.pro       P Y G V K L C G R E F I R A V I F T C G G S R W R R A D I   56
Rat.pro         P Y G V K L C G R E F I R A V I F T C G G S R W R R A D I   55
Porcine.PRO     P Y G V K L C G R E F I R A V I F T C G G S R W R R S D M   58

Human.pro       L A H E A M G D T F P D A D A D E D S L A G E L D E A M G   86
Mouse.pro       L A H E S L G D F F A D G E A N T D H L A S E L D E A V G   85
Rat.pro         L A H D P L G E F F A D G E A N T D H L A S E L D E A V G   84
Porcine.PRO     L A H E A L G D V F S D T D S N A D S - - - E L D E A M A   84

Human.pro       S S E W L A L T K S P Q A F Y R G R P S W Q G T P G V L R   115
Mouse.pro       S S E W L A L T K S P Q A F Y G G R A S W Q G S P G V V R   114
Rat.pro         S S E W L A L T K S P Q V F Y G G R S S W Q G S P G V V R   113
Porcine.PRO     S S E W L A L T K S P E T F Y G V Q P G W Q R T P G A L R   113

Human.pro       G S R D V L A G L S S S C C K W G C S K S E I S S L C       142
Mouse.pro       G S R D V L A G L S S S C C E W G C S K S Q I S S L C       141
Rat.pro         G S R D V L A G L S S S C C E W G C S K S Q I S S L C       140
Porcine.PRO     G S R D V L A G L S S N C C K W G C S K S E I S S L C       140
```

Lane No. 1 2 3 4 5 6 7 8 9 10

2, 4, 6, 8: before induction 3, 5, 7, 9: after induction 1, 10: Molecular Weight Marker 2, 3: Colony1

4, 5: Colony2

6, 7: Colony3

Human novel polypeptide

FIG. 13
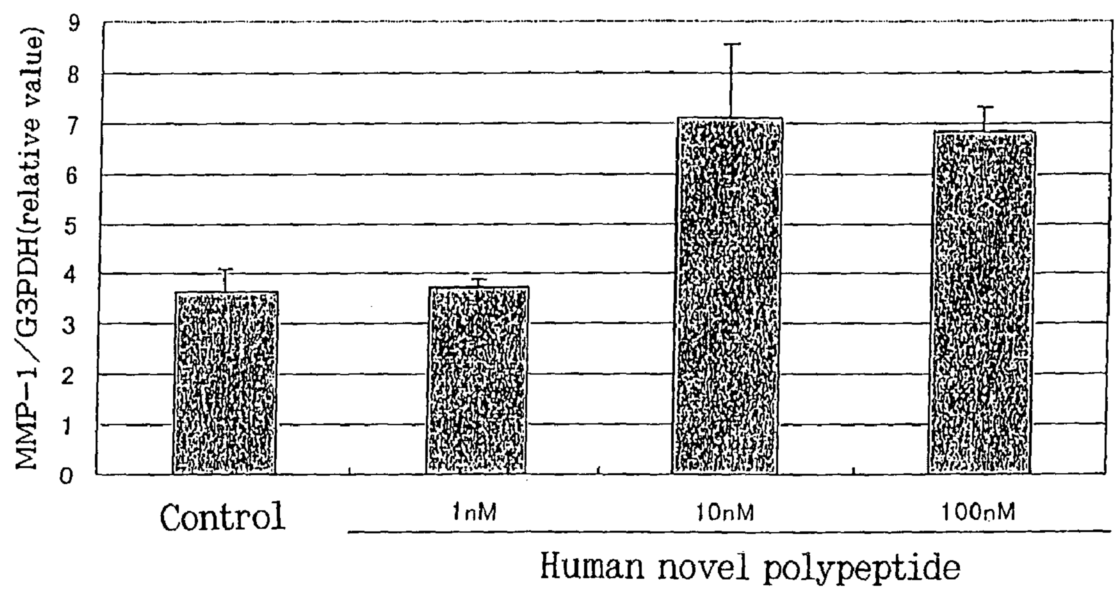
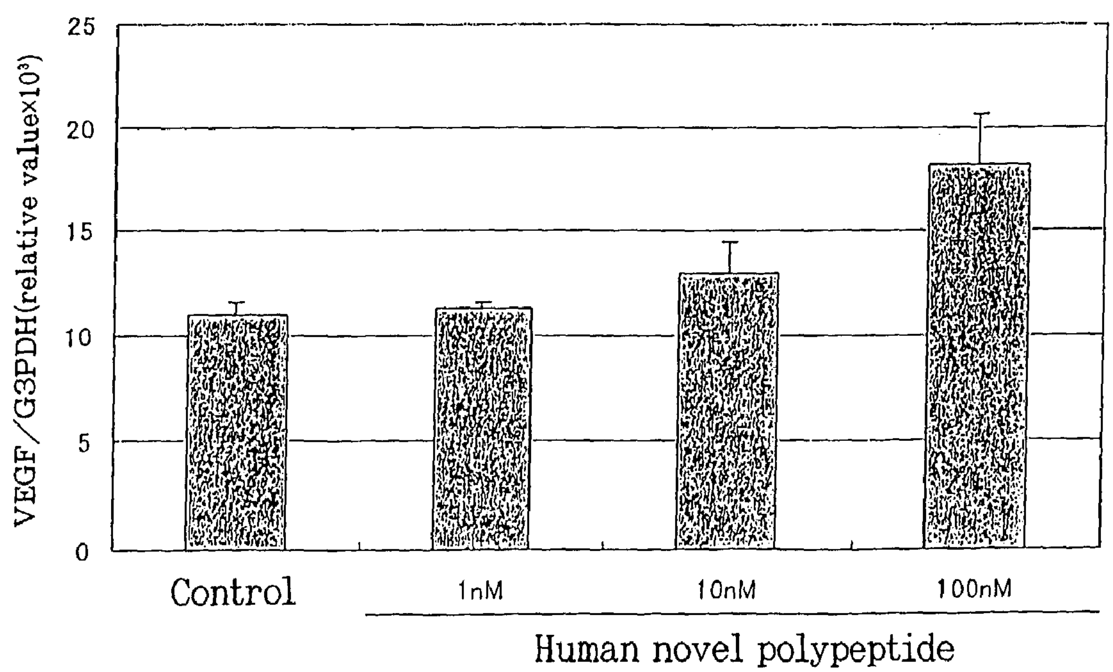

SEQUENCE LISTING

<160> NUMBER OF SEQ ID NOS: 86

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctggcggtat gggtgctgac 20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
actggggcat tggtcctggt g 21

<210> SEQ ID NO 3
<211> LENGTH: 142
<212> TYPE: PRT
<213> ORGANISM: Human

<400> SEQUENCE: 3

```
Met Ala Arg Tyr Met Leu Leu Leu Leu Leu Ala Val Trp Val Leu Thr
  1               5                  10                  15

Gly Glu Leu Trp Pro Gly Ala Glu Ala Arg Ala Ala Pro Tyr Gly Val
             20                  25                  30

Arg Leu Cys Gly Arg Glu Phe Ile Arg Ala Val Ile Phe Thr Cys Gly
         35                  40                  45

Gly Ser Arg Trp Arg Arg Ser Asp Ile Leu Ala His Glu Ala Met Gly
     50                  55                  60

Asp Thr Phe Pro Asp Ala Asp Ala Asp Glu Asp Ser Leu Ala Gly Glu
 65                  70                  75                  80

Leu Asp Glu Ala Met Gly Ser Ser Glu Trp Leu Ala Leu Thr Lys Ser
                 85                  90                  95

Pro Gln Ala Phe Tyr Arg Gly Arg Pro Ser Trp Gln Gly Thr Pro Gly
            100                 105                 110

Val Leu Arg Gly Ser Arg Asp Val Leu Ala Gly Leu Ser Ser Ser Cys
        115                 120                 125

Cys Lys Trp Gly Cys Ser Lys Ser Glu Ile Ser Ser Leu Cys
    130                 135                 140
```

<210> SEQ ID NO 4
<211> LENGTH: 1061
<212> TYPE: DNA
<213> ORGANISM: Human

<400> SEQUENCE: 4

```
ttcaaagcat ctccgtccag catggccagg tacatgctgc tgctgctcct ggcggtatgg     60

gtgctgaccg gggagctgtg gccgggagct gaggcccggg cagcgcctta cggggtcagg    120

ctttgcggcc gagaattcat ccgagcagtc atcttcacct gcgggggctc ccggtggaga    180

cgatcagaca tcctggccca cgaggctatg ggagatacct tcccggatgc agatgctgat    240
```

```
gaagacagtc tggcaggcga gctggatgag gccatggggt ccagcgagtg gctggccctg    300

accaagtcac cccaggcctt ttacaggggg cgacccagct ggcaaggaac ccctggggtt    360

cttcggggca gccgagatgt cctggctggc ctttccagca gctgctgcaa gtgggggtgt    420

agcaaaagtg aaatcagtag cctttgctag tttgagggct gggcagccgt gggcaccagg    480

accaatgccc cagtcctgcc atccactcaa ctagtgtctg gctgggcacc tgtctttcga    540

gcctcacaca ttcattcatt catctacaag tcacagaggc actgtgggct caggcacagt    600

ctcccgacac cacctatcca accctgccct ttgaccagcc tatcatgacc ctggccccta    660

aggaagctgt gcccctgcct ggtcaagtgg ggaccccccc atcctgaccc ctgacctctc    720

cccagcccta accatgcgtt tgcctggcct acacactcca ctgccacaac tgggtcccta    780

ctctacctag gctggccaca cagagacccc tgccccccttc ccagtccaaa ctgtggccat    840

tgtcccctga ccagctaaaa tcaagcctct gtctcagtcc agcctttgca cgcacgcttc    900

ctttgccctg ctttccatcc cctctccctc caactcccct gccagagttc caaggctgtg    960

gaccccagag aaggtggcag gtggcccccc taggagagct ctgggcacat tcgaatcttc   1020

ccaaactcca ataataaaaa ttcgaagact ttggcagaga g                       1061
```

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5

```
ccggatgcag atgctgatga a                                               21
```

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6

```
tggtcaaagg gcagggttgg                                                 20
```

<210> SEQ ID NO 7
<211> LENGTH: 24
<212> TYPE: PRT
<213> ORGANISM: Human

<400> SEQUENCE: 7

```
Asp Val Leu Ala Gly Leu Ser Ser Ser Cys Cys Lys Trp Gly Cys Ser
  1               5                  10                  15

Lys Ser Glu Ile Ser Ser Leu Cys
             20
```

<210> SEQ ID NO 8
<211> LENGTH: 27
<212> TYPE: PRT
<213> ORGANISM: Human

<400> SEQUENCE: 8

```
Arg Ala Ala Pro Tyr Gly Val Arg Leu Cys Gly Arg Glu Phe Ile Arg
  1               5                  10                  15

Ala Val Ile Phe Thr Cys Gly Gly Ser Arg Trp
             20                  25
```

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ggtgaagatg actgctcgga tga 23

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ccgcaaagcc tgaccccgta ag 22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gggggtgtag caaaagtgaa a 21

<210> SEQ ID NO 12
<211> LENGTH: 426
<212> TYPE: DNA
<213> ORGANISM: Human

<400> SEQUENCE: 12
atggccaggt acatgctgct gctgctcctg gcggtatggg tgctgaccgg ggagctgtgg 60
ccgggagctg aggcccgggc agcgccttac ggggtcaggc tttgcggccg agaattcatc 120
cgagcagtca tcttcacctg cgggggctcc cggtggagac gatcagacat cctggcccac 180
gaggctatgg gagatacctt cccggatgca gatgctgatg aagacagtct ggcaggcgag 240
ctggatgagg ccatggggtc cagcgagtgg ctggccctga ccaagtcacc ccaggccttt 300
tacagggggc gacccagctg gcaaggaacc cctggggttc ttcggggcag ccgagatgtc 360
ctggctggcc tttccagcag ctgctgcaag tgggggtgta gcaaaagtga aatcagtagc 420
ctttgc 426

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
gggcaggggt ctctgtgt 18

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14

```
ttcaaagcat ctccgtccag c                                                21
```

<210> SEQ ID NO 15
<211> LENGTH: 72
<212> TYPE: DNA
<213> ORGANISM: Human

<400> SEQUENCE: 15

```
gatgtcctgg ctggcctttc cagcagctgc tgcaagtggg ggtgtagcaa aagtgaaatc      60

agtagccttt gc                                                          72
```

<210> SEQ ID NO 16
<211> LENGTH: 81
<212> TYPE: DNA
<213> ORGANISM: Human

<400> SEQUENCE: 16

```
cgggcagcgc cttacggggt caggctttgc ggccgagaat tcatccgagc agtcatcttc      60

acctgcgggg gctcccggtg g                                                81
```

<210> SEQ ID NO 17
<211> LENGTH: 140
<212> TYPE: PRT
<213> ORGANISM: Rat

<400> SEQUENCE: 17

```
Met Ala Thr Arg Gly Leu Leu Leu Ala Ser Trp Ala Leu Leu Gly Ala
 1               5                  10                  15

Leu Val Leu Gln Ala Glu Ala Arg Pro Ala Pro Tyr Gly Val Lys Leu
            20                  25                  30

Cys Gly Arg Glu Phe Ile Arg Ala Val Ile Phe Thr Cys Gly Gly Ser
        35                  40                  45

Arg Trp Arg Arg Ala Asp Ile Leu Ala His Asp Pro Leu Gly Glu Phe
    50                  55                  60

Phe Ala Asp Gly Glu Ala Asn Thr Asp His Leu Ala Ser Glu Leu Asp
65                  70                  75                  80

Glu Ala Val Gly Ser Ser Glu Trp Leu Ala Leu Thr Lys Ser Pro Gln
                85                  90                  95

Val Phe Tyr Gly Gly Arg Ser Ser Trp Gln Gly Ser Pro Gly Val Val
            100                 105                 110

Arg Gly Ser Arg Asp Val Leu Ala Gly Leu Ser Ser Ser Cys Cys Glu
        115                 120                 125

Trp Gly Cys Ser Lys Ser Gln Ile Ser Ser Leu Cys
    130                 135                 140
```

<210> SEQ ID NO 18
<211> LENGTH: 420
<212> TYPE: DNA
<213> ORGANISM: Rat

<400> SEQUENCE: 18

```
atggcaactc gggggctgct gctggcttcc tgggctctcc tcggggctct ggtgctgcag      60

gccgaggcga ggcccgcgcc ctatggggtg aagctctgcg gtcgggagtt catccgcgcg     120

gtcatcttca cctgcggggg ctcacgatgg cgccgggcgg acatcttggc ccacgaccct     180

ctgggggaat tcttcgctga tggagaagcc aatacagacc acctggccag cgaactggac     240
```

```
gaagctgtgg gctccagcga gtggctggcc ctgaccaaat ccccccaggt cttctatggg    300

ggtcgatcca gctggcaagg gtctcccgga gtggttcggg gcagcagaga tgtgctggct    360

ggcctttcca gcagctgttg cgagtggggc tgtagtaaga gccaaattag cagcttgtgc    420


<210> SEQ ID NO 19
<211> LENGTH: 24
<212> TYPE: PRT
<213> ORGANISM: Rat, Mouse

<400> SEQUENCE: 19

Asp Val Leu Ala Gly Leu Ser Ser Ser Cys Cys Glu Trp Gly Cys Ser
 1               5                   10                  15

Lys Ser Gln Ile Ser Ser Leu Cys
            20


<210> SEQ ID NO 20
<211> LENGTH: 71
<212> TYPE: DNA
<213> ORGANISM: Rat

<400> SEQUENCE: 20

gagtgctggc tggcctttcc agcagctgtt gcgagtgggg ctgtagtaag agccaaatta     60

gcagcttgtg c                                                          71


<210> SEQ ID NO 21
<211> LENGTH: 27
<212> TYPE: PRT
<213> ORGANISM: Rat, Mouse

<400> SEQUENCE: 21

Arg Pro Ala Pro Tyr Gly Val Lys Leu Cys Gly Arg Glu Phe Ile Arg
 1               5                   10                  15

Ala Val Ile Phe Thr Cys Gly Gly Ser Arg Trp
            20                  25


<210> SEQ ID NO 22
<211> LENGTH: 81
<212> TYPE: DNA
<213> ORGANISM: Rat

<400> SEQUENCE: 22

aggcccgcgc cctatggggt gaagctctgc ggtcgggagt tcatccgcgc ggtcatcttc     60

acctgcgggg gctcacgatg g                                               81


<210> SEQ ID NO 23
<211> LENGTH: 141
<212> TYPE: PRT
<213> ORGANISM: Mouse

<400> SEQUENCE: 23

Met Ala Met Leu Gly Leu Leu Leu Leu Ala Ser Trp Ala Leu Leu Gly
 1               5                   10                  15

Ala Leu Gly Leu Gln Ala Glu Ala Arg Pro Ala Pro Tyr Gly Val Lys
            20                  25                  30

Leu Cys Gly Arg Glu Phe Ile Arg Ala Val Ile Phe Thr Cys Gly Gly
        35                  40                  45

Ser Arg Trp Arg Arg Ala Asp Ile Leu Ala His Glu Ser Leu Gly Asp
    50                  55                  60
```

-continued

```
Phe Phe Ala Asp Gly Glu Ala Asn Thr Asp His Leu Ala Ser Glu Leu
65                  70                  75                  80

Asp Glu Ala Val Gly Ser Ser Glu Trp Leu Ala Leu Thr Lys Ser Pro
                85                  90                  95

Gln Ala Phe Tyr Gly Gly Arg Ala Ser Trp Gln Gly Ser Pro Gly Val
            100                 105                 110

Val Arg Gly Ser Arg Asp Val Leu Ala Gly Leu Ser Ser Ser Cys Cys
        115                 120                 125

Glu Trp Gly Cys Ser Lys Ser Gln Ile Ser Ser Leu Cys
    130                 135                 140


<210> SEQ ID NO 24
<211> LENGTH: 423
<212> TYPE: DNA
<213> ORGANISM: Mouse

<400> SEQUENCE: 24

atggcaatgc tcgggctgct gctgctggct tcctgggctc tcctcggggc tctggggctg      60

caggccgagg cgaggccggc gccctacggg gtgaagctct gcggtcggga gttcatccgc     120

gcggtcatct tcacttgcgg aggctcacga tggcgccggg cggacatctt ggcccacgaa     180

tctctggggg acttcttcgc tgatggagaa gccaatacag accacctggc cagcgagctg     240

gatgaagcgg tgggctccag cgagtggctg gccctaacca aatcccccca ggctttctac     300

ggtggtcgag ccagctggca agggtcacct ggagtggttc ggggcagcag agatgtgttg     360

gctggccttt ccagcagttg ctgcgagtgg ggctgtagca agagccaaat tagcagcttg     420

tgc                                                                   423


<210> SEQ ID NO 25
<211> LENGTH: 72
<212> TYPE: DNA
<213> ORGANISM: Mouse

<400> SEQUENCE: 25

gatgtgttgg ctggcctttc cagcagttgc tgcgagtggg gctgtagcaa gagccaaatt      60

agcagcttgt gc                                                          72


<210> SEQ ID NO 26
<211> LENGTH: 81
<212> TYPE: DNA
<213> ORGANISM: Mouse

<400> SEQUENCE: 26

aggccggcgc cctacggggt gaagctctgc ggtcgggagt tcatccgcgc ggtcatcttc      60

acttgcggag gctcacgatg g                                                81


<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27

ggctcttact acagccccac tcgcaacagc                                      30
```

-continued

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
tgctggaaag gccagccagc acatctct 28

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
ggctgctagg ggtatggttg gag 23

<210> SEQ ID NO 30
<211> LENGTH: 28
<212> TYPE: DNA
<213> ORGANISM: Artificial Sequence
<220> FEATURE:
<223> OTHER INFORMATION: Primer

<400> SEQUENCE: 30
aagggtggcc taatggcttt cggatttc 28

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
ttaaaggcca ggcagaggtg tttccactg 29

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
cactctcctg attggcctcc tgctgctc 28

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
ggtcccgaga aagcttaaag gcaggcagag 30

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
ggagaagcca atacagacca cctg 24

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
agtggctggc cctaaccaaa tc 22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
ggtcgcaggc atctcagctg at 22

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
cttcccaatc gctcagccca 20

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
cgcttctcca ttgctcaacc ct 22

<210> SEQ ID NO 39
<211> LENGTH: 470
<212> TYPE: DNA
<213> ORGANISM: Rat

<400> SEQUENCE: 39
ggtcgcaggc atctcagctg atcatggcaa ctcgggggct gctgctggct tcctgggctc 60
tcctcggggc tctggtgctg caggccgagg cgaggcccgc gccctatggg gtgaagctct 120
gcggtcggga gttcatccgc gcggtcatct tcacctgcgg gggctcacga tggcgccggg 180
cggacatctt ggcccacgac cctctggggg aattcttcgc tgatggagaa gccaatacag 240
accacctggc cagcgaactg gacgaagctg tgggctccag cgagtggctg gccctgacca 300
aatcccccca ggtcttctat gggggtcgat ccagctggca agggtctccc ggagtggttc 360
ggggcagcag agatgtgctg gctggccttt ccagcagctg ttgcgagtgg ggctgtagta 420
agagccaaat tagcagcttg tgctaggatc tgggctgagc gattgggaag 470

-continued

<210> SEQ ID NO 40
<211> LENGTH: 475
<212> TYPE: DNA
<213> ORGANISM: Mouse

<400> SEQUENCE: 40

```
ggtcgcaggc atctcagctg atcatggcaa tgctcgggct gctgctgctg gcttcctggg     60
ctctcctcgg ggctctgggg ctgcaggccg aggcgaggcc ggcgccctac ggggtgaagc    120
tctgcggtcg ggagttcatc cgcgcggtca tcttcacttg cggaggctca cgatggcgcc    180
gggcggacat cttggcccac gaatctctgg gggacttctt cgctgatgga gaagccaata    240
cagaccacct ggccagcgag ctggatgaag cggtgggctc cagcgagtgg ctggccctaa    300
ccaaatcccc ccaggctttc tacggtggtc gagccagctg gcaagggtca cctggagtgg    360
ttcggggcag cagagatgtg ttggctggcc tttccagcag ttgctgcgag tggggctgta    420
gcaagagcca aattagcagc ttgtgctagg atcagggttg agcaatggag aagcg         475
```

<210> SEQ ID NO 41
<211> LENGTH: 184
<212> TYPE: DNA
<213> ORGANISM: Rat

<400> SEQUENCE: 41

```
atggcaactc gggggctgct gctggcttcc tgggctctcc tcggggctct ggtgctgcag     60
gccgaggcga ggcccgcgcc ctatggggtg aagctctgcg gtcgggagtt catccgcgcg    120
gtcatcttca cctgcggggg ctcacgatgg cgccgggcgg acatcttggc ccacgaccct    180
ctgg                                                                 184
```

<210> SEQ ID NO 42
<211> LENGTH: 236
<212> TYPE: DNA
<213> ORGANISM: Rat

<400> SEQUENCE: 42

```
gggaattctt cgctgatgga gaagccaata cagaccacct ggccagcgaa ctggacgaag     60
ctgtgggctc cagcgagtgg ctggccctga ccaaatcccc ccaggtcttc tatgggggtc    120
gatccagctg gcaagggtct cccggagtgg ttcggggcag cagagatgtg ctggctggcc    180
tttccagcag ctgttgcgag tggggctgta gtaagagcca aattagcagc ttgtgc        236
```

<210> SEQ ID NO 43
<211> LENGTH: 187
<212> TYPE: DNA
<213> ORGANISM: Mouse

<400> SEQUENCE: 43

```
atggcaatgc tcgggctgct gctgctggct tcctgggctc tcctcggggc tctggggctg     60
caggccgagg cgaggccggc gccctacggg gtgaagctct gcggtcggga gttcatccgc    120
gcggtcatct tcacttgcgg aggctcacga tggcgccggg cggacatctt ggcccacgaa    180
tctctgg                                                              187
```

<210> SEQ ID NO 44
<211> LENGTH: 236
<212> TYPE: DNA
<213> ORGANISM: Mouse

<400> SEQUENCE: 44
gggacttctt cgctgatgga gaagccaata cagaccacct ggccagcgag ctggatgaag 60
cggtgggctc cagcgagtgg ctggccctaa ccaaatcccc ccaggctttc tacggtggtc 120
gagccagctg gcaagggtca cctggagtgg ttcggggcag cagagatgtg ttggctggcc 180
tttccagcag ttgctgcgag tggggctgta gcaagagcca aattagcagc ttgtgc 236

<210> SEQ ID NO 45
<211> LENGTH: 140
<212> TYPE: PRT
<213> ORGANISM: Porcine

<400> SEQUENCE: 45

```
Met Ala Lys Arg Pro Leu Leu Leu Leu Leu Leu Ala Val Trp Val Leu
1               5                   10                  15

Ala Gly Glu Leu Trp Leu Arg Thr Glu Ala Arg Ala Ser Pro Tyr Gly
            20                  25                  30

Val Lys Leu Cys Gly Arg Glu Phe Ile Arg Ala Val Ile Phe Thr Cys
        35                  40                  45

Gly Gly Ser Arg Trp Arg Arg Ser Asp Met Leu Ala His Glu Ala Leu
    50                  55                  60

Gly Asp Val Phe Ser Asp Thr Asp Ser Asn Ala Asp Ser Glu Leu Asp
65                  70                  75                  80

Glu Ala Met Ala Ser Ser Glu Trp Leu Ala Leu Thr Lys Ser Pro Glu
                85                  90                  95

Thr Phe Tyr Gly Val Gln Pro Gly Trp Gln Arg Thr Pro Gly Ala Leu
            100                 105                 110

Arg Gly Ser Arg Asp Val Leu Ala Gly Leu Ser Ser Asn Cys Cys Lys
        115                 120                 125

Trp Gly Cys Ser Lys Ser Glu Ile Ser Ser Leu Cys
    130                 135                 140
```

<210> SEQ ID NO 46
<211> LENGTH: 420
<212> TYPE: DNA
<213> ORGANISM: Porcine

<400> SEQUENCE: 46
atggccaaac gtccactgct gctgctgctg ctggccgtat gggtgctggc tggggagctg 60
tggctgagga ctgaggcccg ggcgtcaccc tatggagtga agctttgcgg ccgtgaattc 120
atccgagcgg tcatctttac ctgcgggggc tcccggtgga gacggtcgga catgctggcc 180
catgaagctc tgggggatgt cttctcagac acagattcca acgcagacag cgagttggac 240
gaggcaatgg cctccagcga atggctggcc ctgaccaagt cccctgagac cttctatggg 300
gttcaaccag gctggcagag aacccctggg gctcttaggg gcagtcgtga tgtcctggct 360
ggcctctcca gcaactgctg caagtggggg tgcagcaaga gtgaaatcag cagcctctgc 420

<210> SEQ ID NO 47
<211> LENGTH: 24
<212> TYPE: PRT
<213> ORGANISM: Porcine

<400> SEQUENCE: 47

```
Asp Val Leu Ala Gly Leu Ser Ser Asn Cys Cys Lys Trp Gly Cys Ser
1               5                   10                  15

Lys Ser Glu Ile Ser Ser Leu Cys
            20
```

<210> SEQ ID NO 48
<211> LENGTH: 72
<212> TYPE: DNA
<213> ORGANISM: Porcine

<400> SEQUENCE: 48

```
gatgtcctgg ctggcctctc cagcaactgc tgcaagtggg ggtgcagcaa gagtgaaatc     60

agcagcctct gc                                                         72
```

<210> SEQ ID NO 49
<211> LENGTH: 27
<212> TYPE: PRT
<213> ORGANISM: Porcine

<400> SEQUENCE: 49

```
Arg Ala Ser Pro Tyr Gly Val Lys Leu Cys Gly Arg Glu Phe Ile Arg
1               5                   10                  15

Ala Val Ile Phe Thr Cys Gly Gly Ser Arg Trp
            20                  25
```

<210> SEQ ID NO 50
<211> LENGTH: 81
<212> TYPE: DNA
<213> ORGANISM: Porcine

<400> SEQUENCE: 50

```
cgggcgtcac cctatggagt gaagctttgc ggccgtgaat tcatccgagc ggtcatcttt     60

acctgcgggg gctcccggtg g                                               81
```

<210> SEQ ID NO 51
<211> LENGTH: 174
<212> TYPE: PRT
<213> ORGANISM: Rat

<400> SEQUENCE: 51

```
Met Ala Thr Arg Gly Leu Leu Leu Ala Ser Trp Ala Leu Leu Gly Ala
1               5                   10                  15

Leu Val Leu Gln Ala Glu Ala Arg Pro Ala Pro Tyr Gly Val Lys Leu
            20                  25                  30

Cys Gly Arg Glu Phe Ile Arg Ala Val Ile Phe Thr Cys Gly Gly Ser
        35                  40                  45

Arg Trp Arg Arg Ala Asp Ile Leu Ala His Asp Pro Leu Gly Glu Cys
    50                  55                  60

Gly Gly Lys Ala Met Asp Leu Glu Gln Val Ser Leu Ile Leu Gln Thr
65                  70                  75                  80

Arg Asp Val Ala Gly Phe Ser Pro Val His Pro Leu Ser Phe Ala Gly
                85                  90                  95

Glu Phe Phe Ala Asp Gly Glu Ala Asn Thr Asp His Leu Ala Ser Glu
            100                 105                 110

Leu Asp Glu Ala Val Gly Ser Ser Glu Trp Leu Ala Leu Thr Lys Ser
        115                 120                 125
```

-continued

```
Pro Gln Val Phe Tyr Gly Gly Arg Ser Ser Trp Gln Gly Ser Pro Gly
    130                 135                 140

Val Val Arg Gly Ser Arg Asp Val Leu Ala Gly Leu Ser Ser Ser Cys
145                 150                 155                 160

Cys Glu Trp Gly Cys Ser Lys Ser Gln Ile Ser Ser Leu Cys
                165                 170
```

```
<210> SEQ ID NO 52
<211> LENGTH: 522
<212> TYPE: DNA
<213> ORGANISM: Rat

<400> SEQUENCE: 52

atggcaactc gggggctgct gctggcttcc tgggctctcc tcggggctct ggtgctgcag     60

gccgaggcga ggcccgcgcc ctatggggtg aagctctgcg gtcgggagtt catccgcgcg    120

gtcatcttca cctgcggggg ctcacgatgg cgccgggcgg acatcttggc ccacgaccct    180

ctgggtgagt gcggagggaa agcaatggac ctggaacagg tgtccttgat cctccagacc    240

agagatgtag ccggattcag ccctgttcat ccactttctt ttgcagggga attcttcgct    300

gatggagaag ccaatacaga ccacctggcc agcgaactgg acgaagctgt gggctccagc    360

gagtggctgg ccctgaccaa atccccccag gtcttctatg gggtcgatc cagctggcaa    420

gggtctcccg gagtggttcg gggcagcaga gatgtgctgg ctggcctttc cagcagctgt    480

tgcgagtggg gctgtagtaa gagccaaatt agcagcttgt gc                       522


<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53

ggragccass mtgtataaat r                                               21


<210> SEQ ID NO 54
<211> LENGTH: 28
<212> TYPE: DNA
<213> ORGANISM: Artificial Sequence
<220> FEATURE:
<223> OTHER INFORMATION: Primer

<400> SEQUENCE: 54

cacccakags stcgtgggcc aagatgtc                                        28


<210> SEQ ID NO 55
<211> LENGTH: 159
<212> TYPE: DNA
<213> ORGANISM: Porcine

<400> SEQUENCE: 55

atggccaaac gtccactgct gctgctgctg ctggccgtat gggtgctggc tggggagctg     60

tggctgagga ctgaggcccg ggcgtcaccc tatggagtga agctttgcgg ccgtgaattc    120

atccgagcgg tcatctttac ctgcgggggc tcccggtgg                           159


<210> SEQ ID NO 56
<211> LENGTH: 239
<212> TYPE: DNA
<213> ORGANISM: Porcine
```

<400> SEQUENCE: 56
tccaggaggc accaaccatc agaaagctgc cttgctgcgt ccactctcac atctcaggca 60
gcccgtccag aatggccaaa cgtccactgc tgctgctgct gctggccgta tgggtgctgg 120
ctggggagct gtggctgagg actgaggccc gggcgtcacc ctatggagtg aagctttgcg 180
gccgtgaatt catccgagcg gtcatcttta cctgcggggg ctcccggtgg agacggtcg 239

<210> SEQ ID NO 57
<211> LENGTH: 29
<212> TYPE: DNA
<213> ORGANISM: Artificial Sequence
<220> FEATURE:
<223> OTHER INFORMATION: Primer

<400> SEQUENCE: 57
gctgccttgc tgcgtccact ctcacatct 29

<210> SEQ ID NO 58
<211> LENGTH: 29
<212> TYPE: DNA
<213> ORGANISM: Artificial Sequence
<220> FEATURE:
<223> OTHER INFORMATION: Primer

<400> SEQUENCE: 58
cactctcaca tctcaggcag cccgtccag 29

<210> SEQ ID NO 59
<211> LENGTH: 193
<212> TYPE: DNA
<213> ORGANISM: Porcine

<400> SEQUENCE: 59
atggccaaac gtccactgct gctgctgctg ctggccgtat gggtgctggc tggggagctg 60
tggctgagga ctgaggcccg ggcgtcaccc tatggagtga agctttgcgg ccgtgaattc 120
atccgagcgg tcatctttac ctgcgggggc tcccggtgga gacggtcgga catgctggcc 180
catgaagctc tgg 193

<210> SEQ ID NO 60
<211> LENGTH: 227
<212> TYPE: DNA
<213> ORGANISM: Porcine

<400> SEQUENCE: 60
gggatgtctt ctcagacaca gattccaacg cagacagcga gttggacgag gcaatggcct 60
ccagcgaatg gctggccctg accaagtccc ctgagacctt ctatggggtt caaccaggct 120
ggcagagaac ccctggggct cttaggggca gtcgtgatgt cctggctggc ctctccagca 180
actgctgcaa gtgggggtgc agcaagagtg aaatcagcag cctctgc 227

<210> SEQ ID NO 61
<211> LENGTH: 572
<212> TYPE: DNA
<213> ORGANISM: Rat

<400> SEQUENCE: 61
ggtcgcaggc atctcagctg atcatggcaa ctcgggggct gctgctggct tcctgggctc 60
tcctcggggc tctggtgctg caggccgagg cgaggcccgc gccctatggg gtgaagctct 120
gcggtcggga gttcatccgc gcggtcatct tcacctgcgg gggctcacga tggcgccggg 180

-continued

```
cggacatctt ggcccacgac cctctgggtg agtgcggagg gaaagcaatg gacctggaac    240

aggtgtcctt gatcctccag accagagatg tagccggatt cagccctgtt catccacttt    300

cttttgcagg ggaattcttc gctgatggag aagccaatac agaccacctg gccagcgaac    360

tggacgaagc tgtgggctcc agcgagtggc tggccctgac caaatccccc caggtcttct    420

atgggggtcg atccagctgg caagggtctc ccggagtggt tcggggcagc agagatgtgc    480

tggctggcct ttccagcagc tgttgcgagt ggggctgtag taagagccaa attagcagct    540

tgtgctagga tctgggctga gcgattggga ag                                  572
```

```
<210> SEQ ID NO 62
<211> LENGTH: 102
<212> TYPE: DNA
<213> ORGANISM: Rat

<400> SEQUENCE: 62

gtgagtgcgg agggaaagca atggacctgg aacaggtgtc cttgatcctc cagaccagag     60

atgtagccgg attcagccct gttcatccac tttcttttgc ag                       102


<210> SEQ ID NO 63
<211> LENGTH: 34
<212> TYPE: PRT
<213> ORGANISM: Rat

<400> SEQUENCE: 63

Gly Glu Cys Gly Gly Lys Ala Met Asp Leu Glu Gln Val Ser Leu Ile
 1               5                  10                  15

Leu Gln Thr Arg Asp Val Ala Gly Phe Ser Pro Val His Pro Leu Ser
            20                  25                  30

Phe Ala


<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64

ccggatccat gcgggcagcg cctta                                           25


<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65

atctcgactg ccccgaagaa cc                                              22


<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66

cagtcgaatg gatgtcctgg ctggc                                           25
```

-continued

```
<210> SEQ ID NO 67
<211> LENGTH: 29
<212> TYPE: DNA
<213> ORGANISM: Artificial Sequence
<220> FEATURE:
<223> OTHER INFORMATION: Primer

<400> SEQUENCE: 67

ccggatccta gcaaaggcta ctgatttca                                          29


<210> SEQ ID NO 68
<211> LENGTH: 399
<212> TYPE: DNA
<213> ORGANISM: Artificial Sequence
<220> FEATURE:
<223> OTHER INFORMATION:

<400> SEQUENCE: 68

atggctagca tgactggtgg acagcaaatg ggtcgcggat ccatgcgggc agcgccttac       60

ggggtcaggc tttgcggccg agaattcatc cgagcagtca tcttcacctg cgggggctcc      120

cggtggagac gatcagacat cctggcccac gaggctatgg gagatacctt cccggatgca      180

gatgctgatg aagacagtct ggcaggcgag ctggatgagg ccatggggtc cagcgagtgg      240

ctggccctga ccaagtcacc ccaggccttt tacagggggc gacccagctg gcaaggaacc      300

cctggggttc ttcggggcag ccgaatggat gtcctggctg gcctttccag cagctgctgc      360

aagtgggggt gtagcaaaag tgaaatcagt agcctttgc                              399


<210> SEQ ID NO 69
<211> LENGTH: 133
<212> TYPE: PRT
<213> ORGANISM: Artificial Sequence
<220> FEATURE:
<223> OTHER INFORMATION:

<400> SEQUENCE: 69

Met Ala Ser Met Thr Gly Gly Gln Gln Met Gly Arg Gly Ser Met Arg
                5                   10                  15

Ala Ala Pro Tyr Gly Val Arg Leu Cys Gly Arg Glu Phe Ile Arg Ala
            20                  25                  30

Val Ile Phe Thr Cys Gly Gly Ser Arg Trp Arg Arg Ser Asp Ile Leu
        35                  40                  45

Ala His Glu Ala Met Gly Asp Thr Phe Pro Asp Ala Asp Ala Asp Glu
    50                  55                  60

Asp Ser Leu Ala Gly Glu Leu Asp Glu Ala Met Gly Ser Ser Glu Trp
65                  70                  75                  80

Leu Ala Leu Thr Lys Ser Pro Gln Ala Phe Tyr Arg Gly Arg Pro Ser
                85                  90                  95

Trp Gln Gly Thr Pro Gly Val Leu Arg Gly Ser Arg Met Asp Val Leu
            100                 105                 110

Ala Gly Leu Ser Ser Ser Cys Cys Lys Trp Gly Cys Ser Lys Ser Glu
        115                 120                 125

Ile Ser Ser Leu Cys
    130


<210> SEQ ID NO 70
<211> LENGTH: 21
<212> TYPE: DNA
<213> ORGANISM: Artificial Sequence
<220> FEATURE:
<223> OTHER INFORMATION: Primer
```

<400> SEQUENCE: 70
acggataccc caaggacatc t 21

<210> SEQ ID NO 71
<211> LENGTH: 24
<212> TYPE: DNA
<213> ORGANISM: Artificial Sequence
<220> FEATURE:
<223> OTHER INFORMATION: Primer

<400> SEQUENCE: 71
ctcagaaaga gcagcatcga tatg 24

<210> SEQ ID NO 72
<211> LENGTH: 29
<212> TYPE: DNA
<213> ORGANISM: Artificial Sequence
<220> FEATURE:
<223> OTHER INFORMATION:

<400> SEQUENCE: 72
cagctccttt ggcttcccta gaactgtga 29

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
ccagcacata ggagagatga gc 22

<210> SEQ ID NO 74
<211> LENGTH: 21
<212> TYPE: DNA
<213> ORGANISM: Artificial Sequence
<220> FEATURE:
<223> OTHER INFORMATION: Primer

<400> SEQUENCE: 74
ggaacattta cacgtctgcg g 21

<210> SEQ ID NO 75
<211> LENGTH: 25
<212> TYPE: DNA
<213> ORGANISM: Artificial Sequence
<220> FEATURE:
<223> OTHER INFORMATION:

<400> SEQUENCE: 75
agcaagacaa gaaaatccct gtggg 25

<210> SEQ ID NO 76
<211> LENGTH: 19
<212> TYPE: DNA
<213> ORGANISM: Artificial Sequence
<220> FEATURE:
<223> OTHER INFORMATION: Primer

<400> SEQUENCE: 76
gaaggtgaag gtcggagtc 19

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gaagatggtg atgggatttc 20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
caagcttccc gttctcagcc 20

<210> SEQ ID NO 79
<211> LENGTH: 54
<212> TYPE: DNA
<213> ORGANISM: Artificial Sequence
<220> FEATURE:
<223> OTHER INFORMATION: for peptide

<400> SEQUENCE: 79
ctccagccta ggcttttgca aaaaccacca tggagctgag gccctggttg ctat 54

<210> SEQ ID NO 80
<211> LENGTH: 66
<212> TYPE: DNA
<213> ORGANISM: Artificial Sequence
<220> FEATURE:
<223> OTHER INFORMATION: for peptide

<400> SEQUENCE: 80
ttatttccta gggaattcat caatggtgat ggtgatgatg ggcctgactg gacgtgaggg 60
tcttgc 66

<210> SEQ ID NO 81
<211> LENGTH: 60
<212> TYPE: DNA
<213> ORGANISM: Artificial Sequence
<220> FEATURE:
<223> OTHER INFORMATION: for peptide

<400> SEQUENCE: 81
aacagtcaat tgccaccatg gcaagataca tgctgctgct gctcctggcg gtatgggtgc 60

<210> SEQ ID NO 82
<211> LENGTH: 120
<212> TYPE: DNA
<213> ORGANISM: Artificial Sequence
<220> FEATURE:
<223> OTHER INFORMATION: for peptide

<400> SEQUENCE: 82
tcagcaaagg ctactgattt cacttttgct gcaccccac ttgcaacagg agctgctaag 60
gccagccagg acatcgcggc ggccccgaag cctcccaggg gttccttgcc aggagggtcg 120

-continued

```
<210> SEQ ID NO 83
<211> LENGTH: 59
<212> TYPE: DNA
<213> ORGANISM: Artificial Sequence
<220> FEATURE:
<223> OTHER INFORMATION: for peptide

<400> SEQUENCE: 83

tttattagcg gccgctcagc aaaggctact gatttcactt ttgctacacc cccacttgc      59


<210> SEQ ID NO 84
<211> LENGTH: 70
<212> TYPE: DNA
<213> ORGANISM: Artificial Sequence
<220> FEATURE:
<223> OTHER INFORMATION: for peptide

<400> SEQUENCE: 84

aggcatgaat tcccaccatg gcaatgctcg ggctgctgct gctggcttcc tgggctctcc     60

tcggggctct                                                            70


<210> SEQ ID NO 85
<211> LENGTH: 120
<212> TYPE: DNA
<213> ORGANISM: Artificial Sequence
<220> FEATURE:
<223> OTHER INFORMATION: for peptide

<400> SEQUENCE: 85

caacgcggcc gctagcacaa gctgctaatt tggctcttgc tacagcccca ctcgcagcaa     60

ctgctggaaa ggccagccaa cacatctctc ctgccccgaa cccttccagg tgacccttgc    120


<210> SEQ ID NO 86
<211> LENGTH: 62
<212> TYPE: DNA
<213> ORGANISM: Artificial Sequence
<220> FEATURE:
<223> OTHER INFORMATION: for peptide

<400> SEQUENCE: 86

tcaacgcggc cgctagcaca agctgctaat ttggctcttg ctacagcccc actcgcagca     60

ac                                                                    62
```

INSULIN/IGF/RELAXIN FAMILY POLYPEPTIDES AND DNAS THEREOF

This application is the National Phase filing of International Patent Application No. PCT/JP01/03399, filed Apr. 20, 2001.

FIELD OF THE INVENTION

The present invention relates to a novel secretory biological function regulatory protein and its DNA, etc., and more particularly, to a novel protein of the insulin/IGF/relaxin family and its DNA, etc.

BACKGROUND ART

Organisms are engaged in signal transduction mutually between cells or tissues, thus maintaining well-balanced regulation of development, differentiation, proliferation, maintenance of homeostasis, etc. In many cases, proteinous factors mediate them. For example, many secretory factors (humoral factors) that participate in the immune system or the erythropoietic system were found and these factors are called cytokines. Lymphokines, monokines, interferons, colony-stimulating factors, tumor necrosis factors, etc. are included in cytokines. These cytokines have been actively studied on their involvement in diseases or applications to pharmaceuticals.

Humoral factors produced in endocrine tissues such as peptide hormones, growth factors, etc. also play some crucial roles for sustained homeostasis or growth and their application to medicaments have been extensively studied.

In view of their structural characteristics, insulin, insulin-like growth factor I (IGF-I), insulin-like growth factor II (IGF-II), relaxins H1 and H2 are considered to be humoral factors that constitute family members, and are responsible for a wide range of physiological roles in the body, including metabolic regulation of carbohydrates, growth promotion of tissues, control of reproductive functions, etc. [BioScience Term Library, Cytokine/Growth Factor, Yodosha, pages 108–109, 1995; Molecular Biology of Hormone 6, Development and Growth Factor/Hormone, Gakkai Shuppan Center, pages 1–23, 1996]. Moreover, new molecular species belonging to the same family are in the process of discovery [Molecular Endocrinology, 13, 2163–2174, 1999]. The structural characteristic of these precursor proteins lies in possessing the signal sequence-B domain-C domain-A domain structure. B and A domains, which are mature molecules, are connected via disulfide bonds. Furthermore, one disulfide bond located within the A domain is important for maintenance of the steric structure and expression of activities. Insulin, insulin-like growth factors and relaxins have a variety of physiological activities and are important factors for signal transduction in vivo. Insulin is secreted from β cells of the pancreas and important for regulation of energy metabolism, including promotion of sugar uptake in liver, muscle and adipose tissues, promotion of fatty acid synthesis, promotion of glycogen synthesis, etc. In addition, insulin has a cell proliferation activity. IGF-I is synthesized mainly in liver and promotes the proliferation or differentiation of many cells including bone-derived cells. IGF-II has a cell proliferation promoting activity and an insulin-like activity, like IGF-I. These factors bind to specific receptors to cause autophosphorylation of the receptors, which could be a trigger of a chain of subsequent reactions. Turning to relaxin, it was recently found to have a wide variety of physiological activities, including activities primarily associated with reproductive functions such as relaxation of birth canal, softening of connective tissues due to reconstruction of collagen, promotion of proliferation, differentiation of mammary gland, etc. These activities include, for example, promotion in dilation of blood vessels in uterus, mammary gland, lung, heart, etc., effects on heart strokes, inhibition of histamine release from mast cells, inhibition of platelet aggregation, secretory regulation of pituitary hormone, regulation of body fluid balance, regulation of proliferation or differentiation of breast cancer in the culture system, and the like [Gen. Pharmacol., 28, 13–22, 1997].

These proteinous and peptidergic factors, which are important for the living body, were discovered in the past, using as an indicator their inherent physiological activities. Also, by cloning techniques wherein homology to a known physiologically active protein will become a clue, similar genes having high homology have been found on their track. In order to maintain healthy conditions of the higher organisms, especially mammals, it is highly likely that humoral functional molecules other than known gene groups, which are yet unidentified by known means and their existence is yet unknown, would play some important physiological roles.

Recently, various investigations have been made with an attempt to take advantage of data processing technology using a computer and harness new gene products discovered from DNA sequencing information for biology, medicine, veterinary medicine, etc., that is, bioinformatics (Trends in Biotechnology, 14, 294–298, 1996]. Since a large scale sequencing of cDNA library becomes possible in these years, a huge number of new genes or candidates thereof come to be found by EST (expressed sequence tag) information thus accumulated. However, sequencing situation that published various databases related to the now existing cDNAs cannot cover all of the expression genes in each organism. Thus, it is not necessarily easy to further search for completely new useful gene products in these databases. On the other hand, sequencing of all DNAs possessed by one organism, namely, genome sequencing has already been completed in some species of bacteria, fungi (yeast, etc.), insects and plants; human genome sequencing is also expected to be completed in a few years. Indeed, a number of genes encoding secretory proteins or secretory peptides have been isolated so far, but in view of the entire genome, it can be hardly said to cover all of them. Since a novel substance belonging to the insulin/IGF/relaxin family will be applicable to medical treatment with high expectation, it has been strongly desired to develop such a substance.

DISCLOSURE OF THE INVENTION

An object of the invention is to provide a novel protein belonging to the insulin/IGF/relaxin family, which is available in biology, medicine, veterinary medicine, etc., its precursor protein and fragments thereof, as well as a polynucleotide encoding the same. Another object of the invention is to provide a recombinant vector containing such a polynucleotide, transformed host cells containing the vector, and a transgenic animal, to which a gene bearing such a polynucleotide is transfected. A further object of the invention is to provide a method of producing such a protein or a polypeptide, an antibody to such a protein or a polypeptide, an agonist or an antagonist, or a receptor, and a method of identification thereof. A still further object of the present invention is to provide a pharmaceutical composition comprising such a protein, polypeptide, polynucleotide, antagonist, antibody or receptor, a method of treating diseases, a method of preventing diseases, etc.

In order to solve the foregoing problems, the inventors made extensive studies and as a result, successfully discovered a novel gene expressed in human body and found that the protein encoded by the gene is a novel secretory biological function-regulating protein.

The inventors made further investigations and as a result, found novel rat, rat variant, mouse and porcine secretory physiological function regulatory proteins.

Based on these findings, the inventors have made extensive studies and come to accomplish the present invention.

That is, the present invention provides:

(1) A polypeptide containing the same or substantially the same amino acid sequence as the amino acid sequence represented by SEQ ID NO:7, its amide or ester, or a salt thereof;

(2) The polypeptide or its amide or ester, or a salt thereof, according to (1), wherein substantially the same amino acid sequence is represented by SEQ ID NO:19 or SEQ ID NO:47;

(3) A polypeptide containing the same or substantially the same amino acid sequence as the amino acid sequence represented by SEQ ID NO:8, its amide or ester, or a salt thereof;

(4) The polypeptide or its amide or ester, or a salt thereof, according to (3), wherein substantially the same amino acid sequence is represented by SEQ ID NO:21 or SEQ ID NO:49;

(5) The polypeptide or its amide or ester, or a salt thereof, according to (1) or 3, which contains the same or substantially the same amino acid sequence represented by SEQ ID NO:7, and the same or substantially the same amino acid sequence as the amino acid sequence represented by SEQ ID NO:8;

(6) The polypeptide or its amide or ester, or a salt thereof, wherein the same or substantially the same amino acid sequence as the amino acid sequence represented by SEQ ID NO:7, its amide or ester, or a salt thereof, or the same or substantially the same amino acid sequence as the amino acid sequence represented by SEQ ID NO:8, its amide or ester, or a salt thereof are bonded through disulfide bonds;

(7) The polypeptide or its amide or ester, or a salt thereof, according to (5) or (6), wherein the same or substantially the same amino acid sequence as the amino acid sequence represented by SEQ ID NO:7 is the amino acid sequence is represented by SEQ ID NO:19 or SEQ ID NO:47, and the same or substantially the same amino acid sequence as the amino acid sequence represented by SEQ ID NO:8 is the amino acid sequence is represented by SEQ ID NO:21 or SEQ ID NO:49;

(8) A DNA containing a DNA encoding the polypeptide according to (1) or 3;

(9) The polypeptide or its amide or ester, or a salt thereof, according to (1) or 3, which contains the same or substantially the same amino acid sequence as the amino acid sequence represented by SEQ ID NO:3;

(10) The polypeptide or its amide or ester, or a salt thereof, according to (9), wherein substantially the same amino acid sequence is the amino acid sequence represented by SEQ ID NO:17, SEQ ID NO:23, SEQ ID NO:45 or SEQ ID NO:51, or its amide or ester, or a salt thereof;

(11) The DNA according to (8), containing a DNA encoding the polypeptide according to (9);

(12) The DNA according to (10), having the base sequence represented by SEQ ID NO:12, SEQ ID NO:18, SEQ ID NO:24, SEQ ID NO:46 or SEQ ID NO:52;

(13) A recombinant vector containing the DNA according to (8);

(14) A transformant transformed with the recombinant vector of (13);

(15) A method of manufacturing the polypeptide or its amide or ester, or a salt thereof, according to (1), (3) or (6), which comprises culturing the transformant of (14) and producing the polypeptide according to (1), (3) or (6);

(16) An antibody to the polypeptide or its amide or ester, or a salt thereof, according to (1), (3) or (6);

(17) A method of screening a compound that promotes or inhibits the activity of the polypeptide or its amide or ester, or a salt thereof, according to (1), (3) or (6), which comprises using the polypeptide or its amide or ester, or a salt thereof, according to (1), (3) or (6);

(18) A kit for screening a compound or its salt that promotes or inhibits the activity of the polypeptide or its amide or ester, or a salt thereof, according to (1), (3) or (6), comprising the polypeptide or its amide or ester, or a salt thereof, according to (1), (3) or (6);

(19) A compound or its salt that promotes or inhibits the polypeptide, or its amide or ester, or a salt thereof, according to (1), (3) or (6), which is obtainable using the screening method according to (17) or the screening kit according to (18);

(20) A pharmaceuticals comprising a compound or its salt that promotes or inhibits the activity of the polypeptide, or its amide or ester, or a salt thereof, according to (1), (3) or (6), which is obtainable using the screening method according to (17) or the screening kit according to (18);

(21) A pharmaceuticals comprising the polypeptide, its amide or ester, or a salt thereof, according to (1), (3) or (6);

(22) A pharmaceuticals comprising the antibody according to (16);

(23) A prophylactic/therapeutic agent for abnormality of metabolic regulation, inhibition of growth/proliferation/differentiation of tissue, hypogonadism, dysplasia of connective tissue, fibrillation of tissue, circulatory disorders, endocrine disruption, abnormality of body fluid balance, central disease, immune system disease or angiogenic disorder, comprising (i) the polypeptide, its amide or ester, or a salt thereof, according to (1), (3) or (6), (ii) the compound or its salt according to (1)9, or (iii) the antibody according to (16);

(24) The agent according to (23), which is an agent for the prevention/treatment of liver cirrhosis, pulmonary fibrosis, scleroderma, renal fibrosis or peripheral arterial disease;

(25) A diagnostic agent comprising the antibody according to (16);

(26) Use of (i) the polypeptide, its amide or ester, or a salt thereof, according to (1), (3) or (6), (ii) a compound or its salt that promotes or inhibits the activity of the polypeptide, its amide or ester, or a salt thereof, according to (1), (3) or (6), which is obtainable using the screening method of (17) or the screening kit of (18), or (iii) the antibody according to (16), to manufacture a pharmaceutical having a prophylactic/therapeutic effect for abnormality of metabolic regulation, inhibition of growth/proliferation/differentiation of tissue, hypogonadism, dysplasia of connective tissue, fibrillation of tissue, circulatory disorders, endocrine disruption, abnormality of body fluid balance, central disease, immune system disease or angiogenic disorder;

(27) A method of preventing/treating abnormality of metabolic regulation, inhibition of growth/proliferation/differentiation of tissue, hypogonadism, dysplasia of connective tissue, fibrillation of tissue, circulatory disorders, endocrine disruption, abnormality of body fluid balance, central disease, immune system disease or angiogenic disorder, which comprises administering to a mammal (i) the polypeptide, its amide or ester, or a salt thereof, according to (1), (3) or (6), (ii) a compound or its salt that promotes or inhibits the activity of the polypeptide, its amide or ester, or a salt thereof, according to (1), (3) or (6), which is obtainable using the screening method of (17) or the screening kit of (18), or (iii) the antibody according to (16); and the like.

Furthermore, the DNA and the polypeptide, its amide or ester, or salts thereof, etc. in accordance with the present invention are available for basic studies of molecular weight markers, tissue markers, chromosome mapping, identification of hereditary diseases, primers, design of probes, etc.

BRIEF DESCRIPTION OF THE DRAWINGS

FIG. 1 shows the open reading frame (SEQ ID NO.: 4, bases 22—450) of novel protein (precursor protein) of the invention and the amino acid sequence encoded thereby (SEQ ID NO.: 3).

FIG. 2 shows the results obtained by analyzing the expression tissue of human polypeptide of the present invention by RT-PCR in EXAMPLE 4.

In the figure, lanes 1, 2, 3, 4, 5, 6, 7, 8, 9, 10, 11, 12, 13, 14, 15, 16, 17, 18, 19, 20, 21, 22, 23, 24, 25, 26, 27, 28 and 29 designate heart, brain, placenta, lung, liver, skeletal muscle, kidney, pancreas, spleen, thymus, prostate, testis, ovary, small intestine, colon, peripheral blood leukocyte, hypothalamus, hippocampus, pituitary, adipocyte, fetal brain, fetal lung, fetal liver, fetal kidney, fetal heart, fetal spleen, fetal thymus, fetal skeletal muscle and genomic DNA, respectively.

FIG. 3 shows the alignment of each of the amino acid sequences in human (human.pro SEQ ID NO.: 3), mouse (mouse.pro SEQ ID NO.: 23), rat (rat.pro SEQ ID NO.: 17) and porcine (porcine.pro SEQ ID NO.: 45) novel proteins (precursor proteins) of the present invention.

Figure 4:
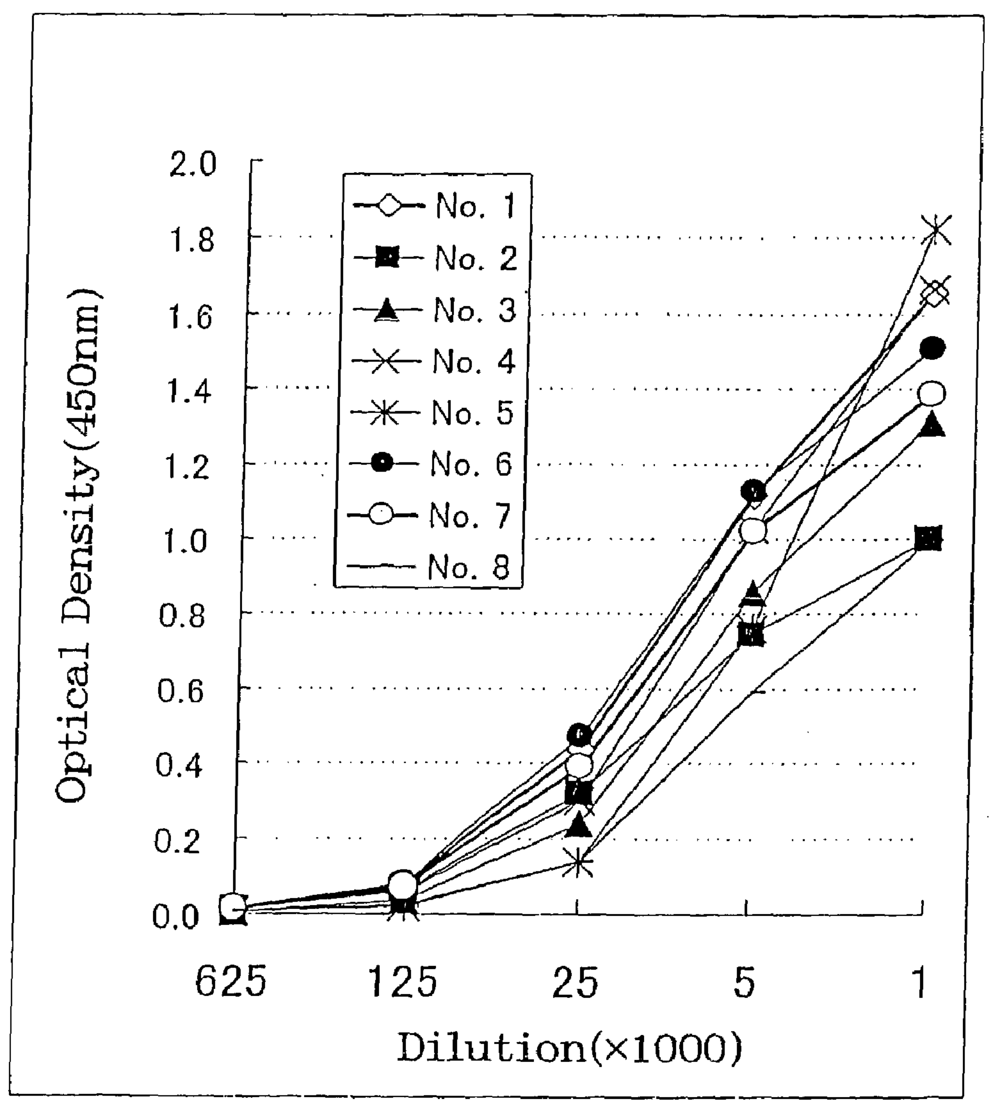

FIG. 4 shows the antibody titer of mouse antisera to the novel polypeptide A chain N-terminal peptide of the present invention.

Figure 5:
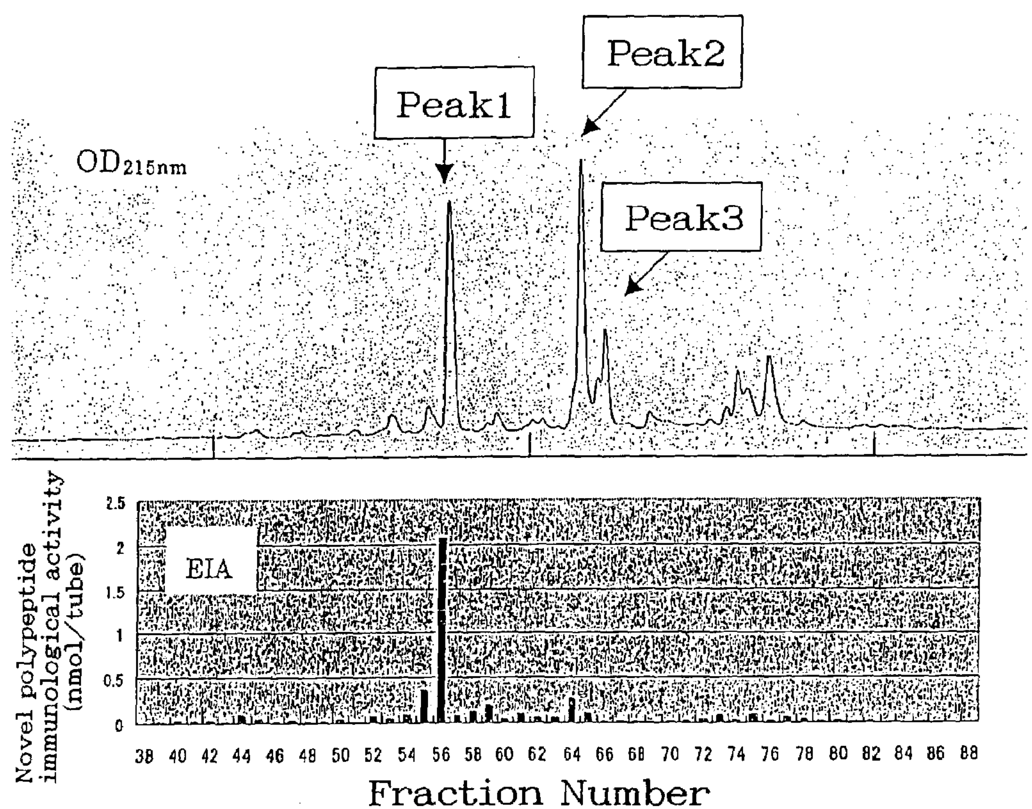

FIG. 5 shows the results detected by the absorbance at 215 nm and the immunological activity when the novel polypeptide of the present invention was purified from the culture supernatant of the novel polypeptide-introduced AtT20 cell line using reversed phase HPLC.

Figure 6:
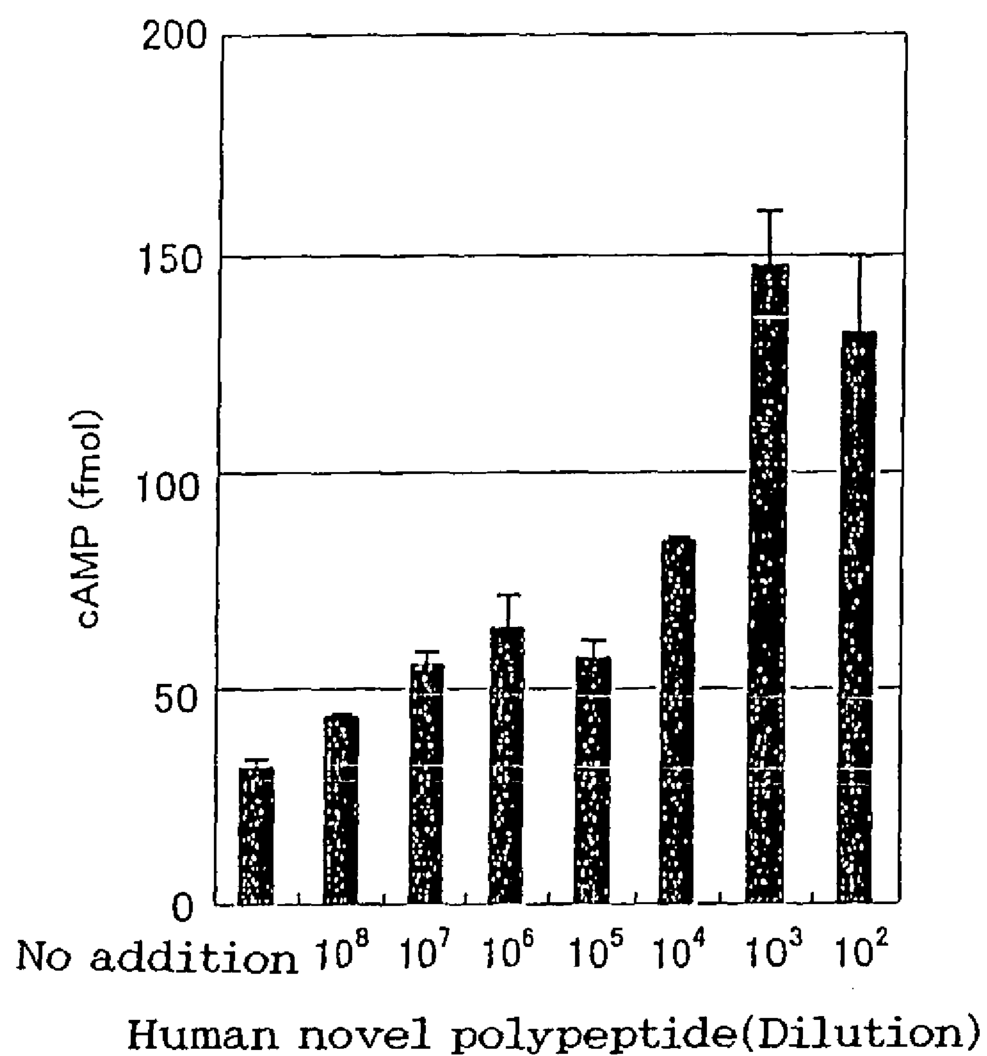

FIG. 6 shows the intracellular cAMP production-promoting activity in the THP-1 cell line of the purified human novel polypeptide preparation.

Figure 7:
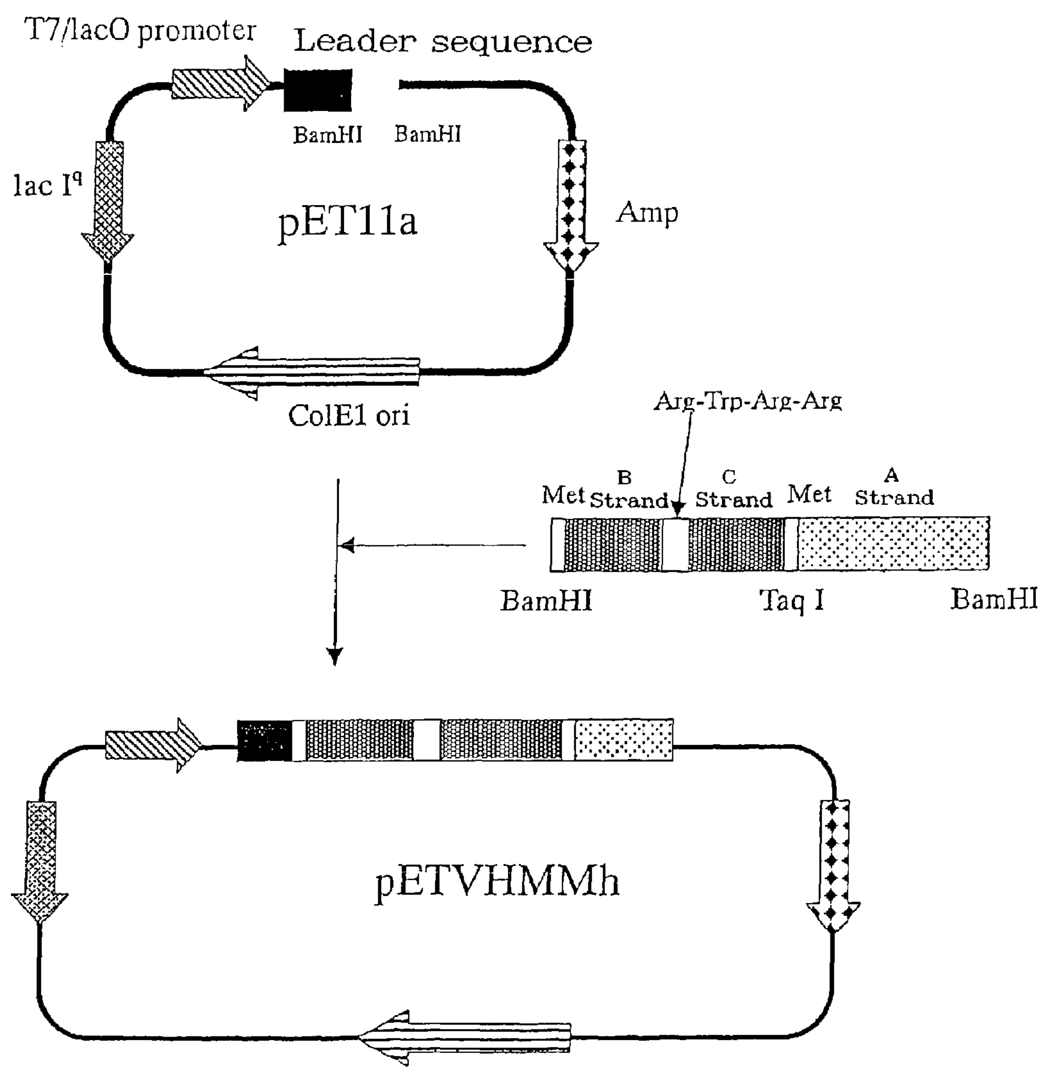

FIG. 7 shows the construction scheme of the plasmid for human novel polypeptide fused protein *E. coli* expression.

In the figure, "T7/lacO promoter," "Amp," "lac $I^q$," "B chain", "A chain" and "C chain" designate the T7 promoter and lac operator region, the ampicillin resistance region, the plasmid replication origin, the lac repressor region, the base sequence represented by SEQ ID NO:16, the base sequence represented by SEQ ID NO:15, and the 184–375 base sequence in the base sequence represented by SEQ ID NO:4, respectively.

Figure 8:
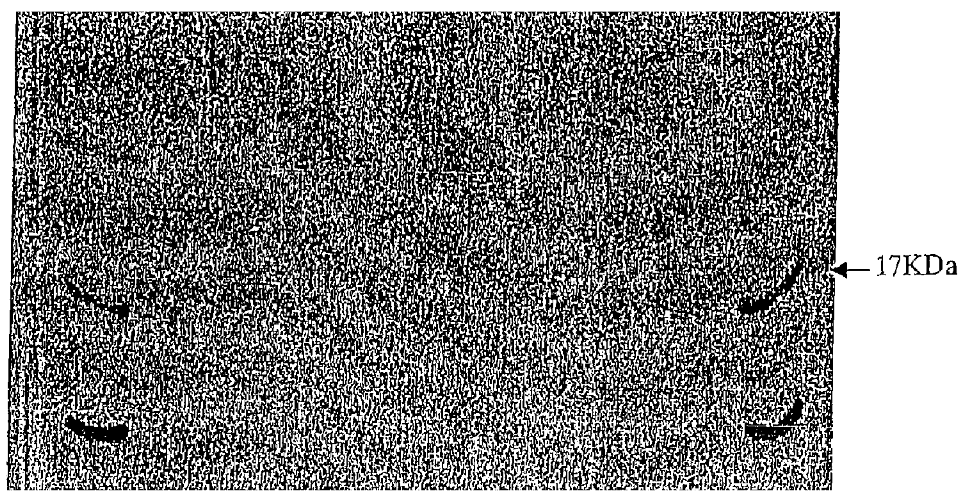

FIG. 8 shows the results of the whole cell protein prepared from human novel polypeptide-fused protein expressed recombinant *E. coli* on SDS-PAGE.

Figure 9:
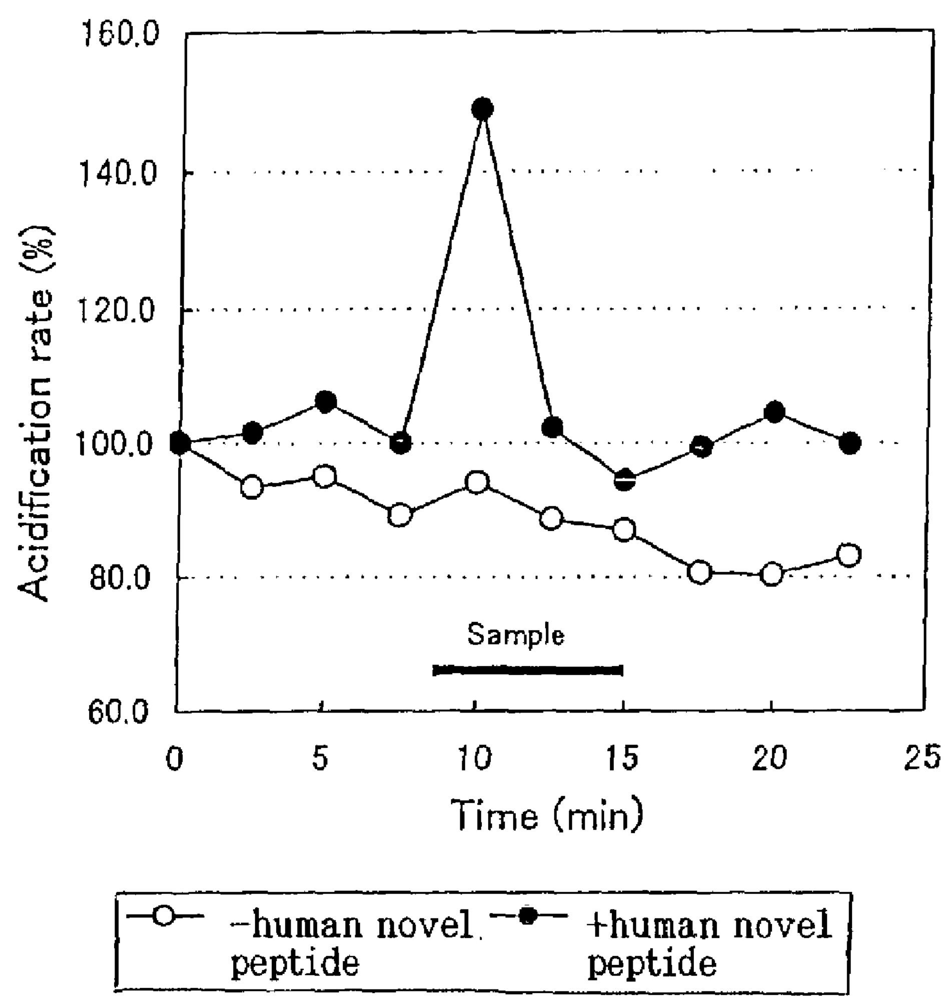

FIG. 9 shows the cell stimulating activity of the purified human novel polypeptide preparation on the THP-1 cell line.

Figure 10:
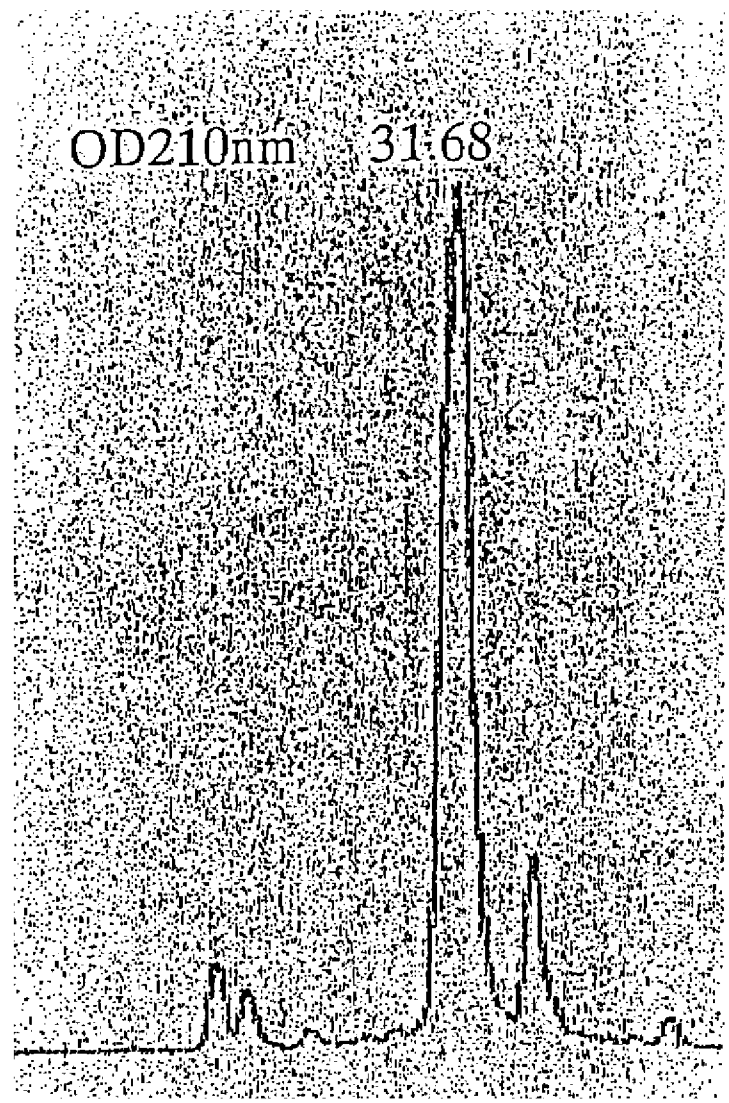

FIG. 10 shows a pattern of the reaction product obtained after treating (16–53)/(110–133) with trypsin and CPB, when the product was separated using TSKgel ODS-80Ts column.

Figure 11:
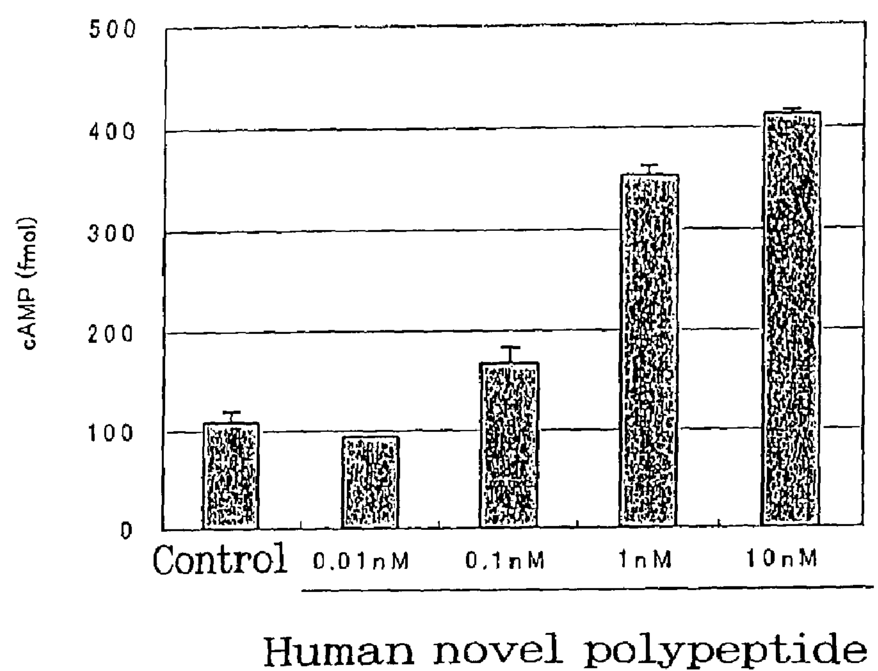

FIG. 11 shows the intracellular cAMP production promoting activity of the human novel polypeptide prepared from *E. coli* on the THP-1 cell line.

Figure 12:
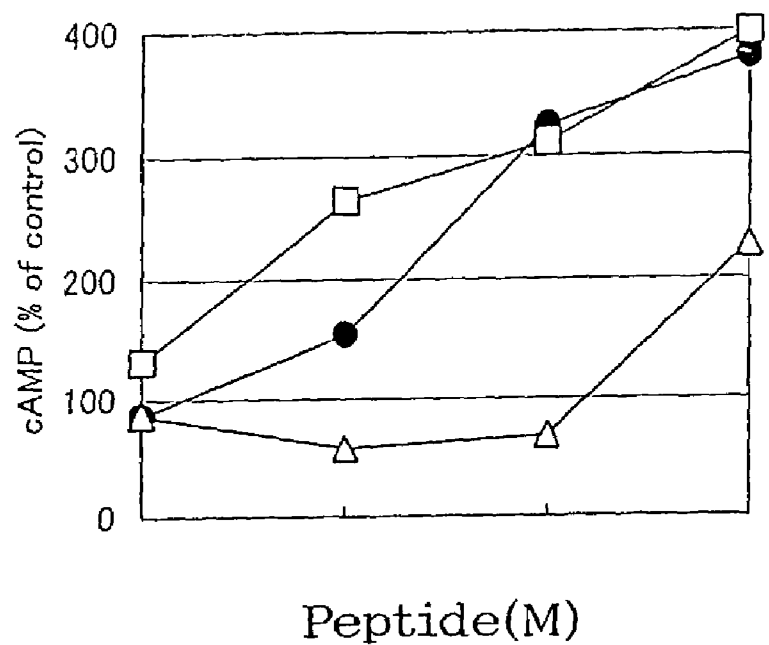

FIG. 12 shows the intracellular cAMP production promoting activity of the human novel polypeptide derivatives prepared from *E. coli* on the THP-1 cell line, wherein symbols-●-, -□- and -Δ- denote the human novel polypeptides (16–42)/(110–133), (16–53)/(110–133) and (16–41)/(110–133), respectively.

FIG. 13 shows the results of the expression promoting activity of MMP-1 and VEGF genes on normal human pulmonary fibroblast strain CCD-19Lu by the purified human novel polypeptide (16–42)/(110–133) preparation.

Figure 14:
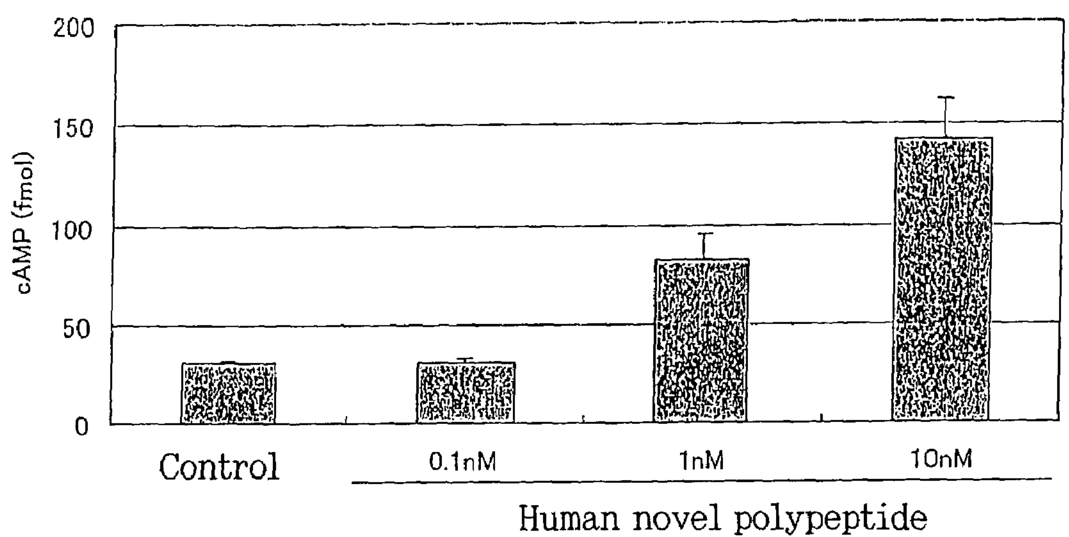

FIG. 14 shows the intracellular cAMP production promoting activity of the purified human novel polypeptide (16–42)/(110–133) preparation in normal human skin fibroblast strain NHDF.

Figure 15:
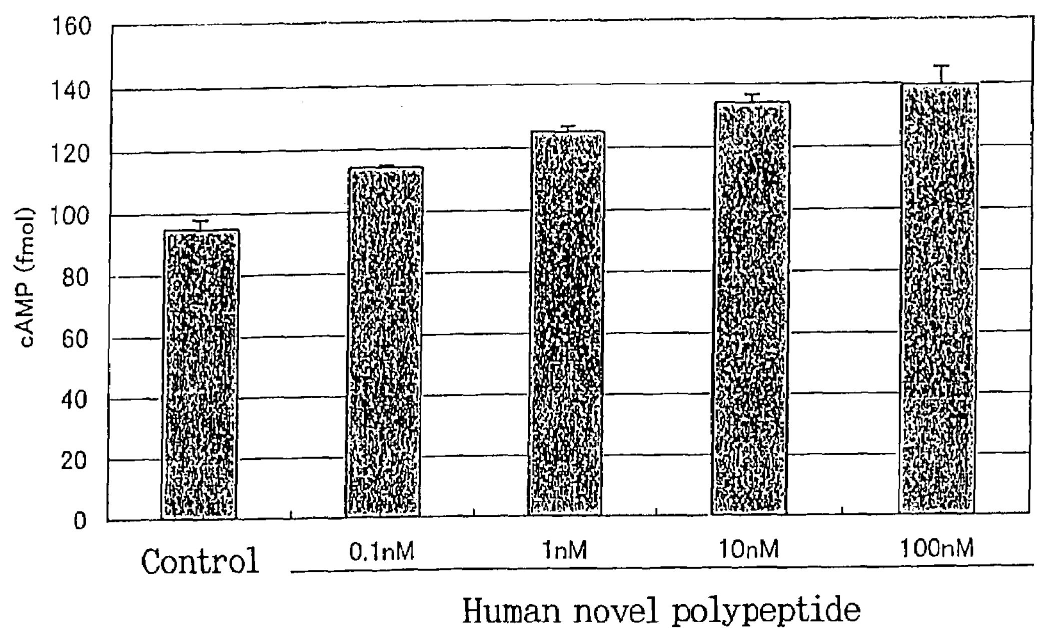

FIG. 15 shows the intracellular cAMP production promoting activity of the purified human novel polypeptide (16–42)/(110–133) preparation in primary culture cells of normal rat anterior pituitary.

Figure 16:
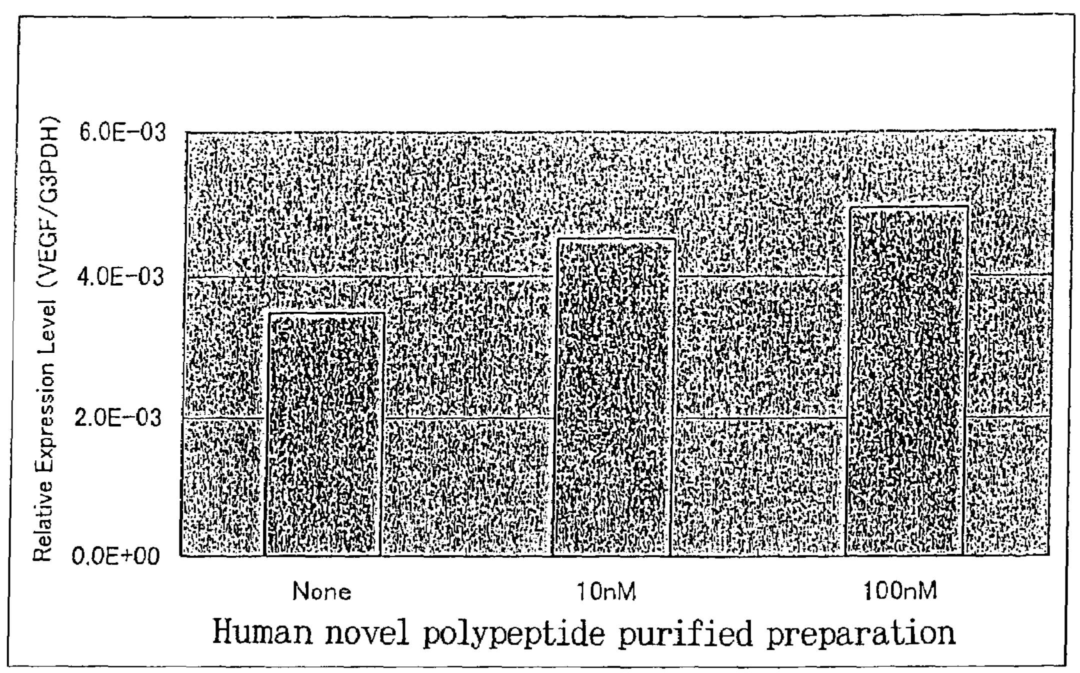

FIG. 16 shows the VEGF gene expression promoting activity of the purified human novel polypeptide (16–42)/(110–133) preparation on THP-1 cells.

Figure 17:
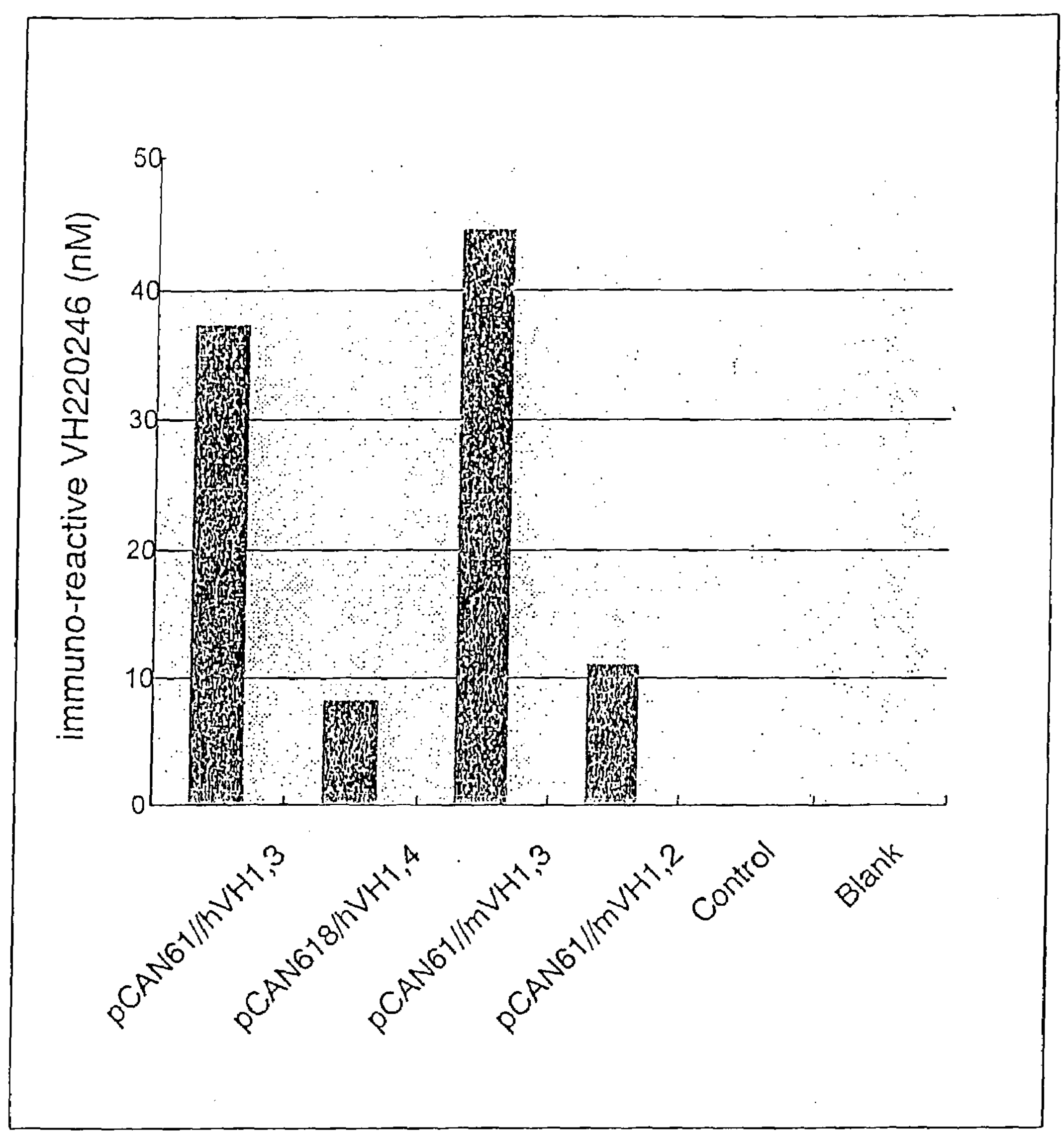

FIG. 17 shows the immuno-reactivity of novel polypeptides in the culture supernatants of COS-7 cells introduced with various novel polypeptide expression vectors, wherein Control and Blank show the immuno-reactivity in the culture supernatant of the parent plasmid pCAN618-introduced COS-7 cells and in the culture supernatant of COS-7 cells, respectively.

Figure 18:
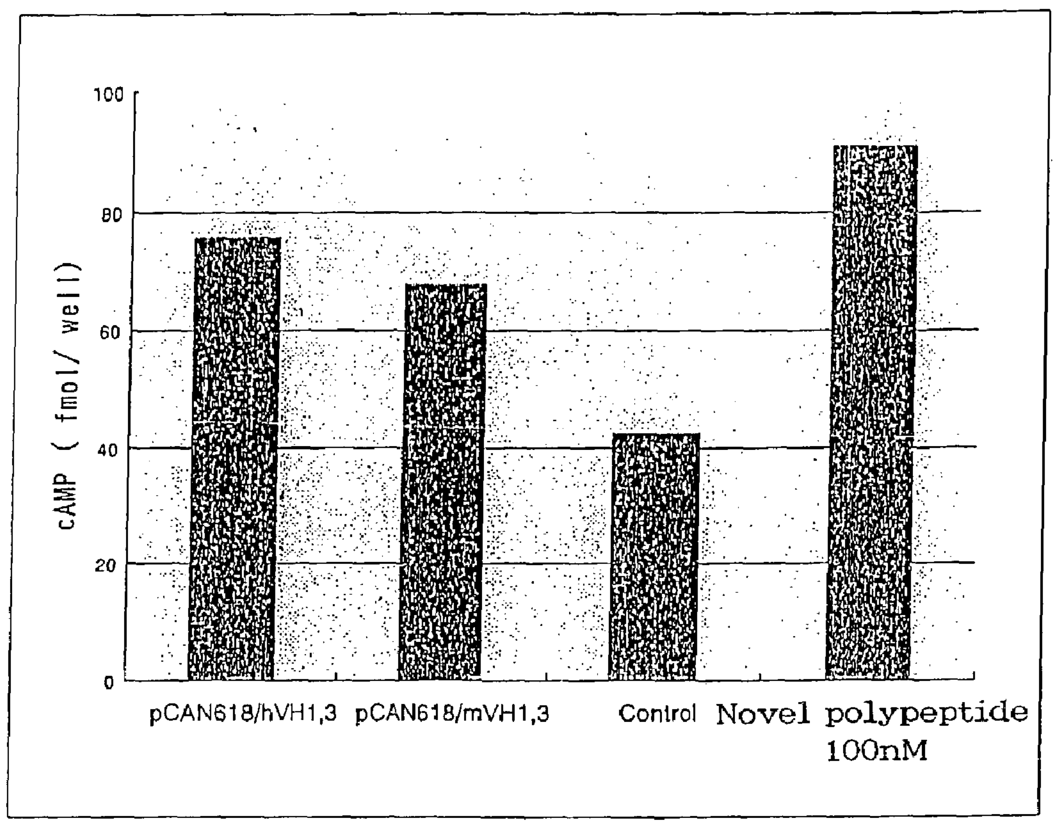

FIG. 18 shows the intracellular cAMP production promoting activity on THP-1 cells in the culture supernatant of the novel polypeptide expression vector-introduced COS-7 cells, wherein Control shows the intracellular cAMP production promoting activity on THP-1 cells when the culture supernatant of the parent plasmid pCAN618-introduced COS-7 cells was added, and 100 nM Novel Polypeptide shows the activity when 100 nM of the purified novel polypeptide preparation was added.

BEST MODE FOR CARRYING OUT THE INVENTION

The polypeptide of the present invention containing the same or substantially the same amino acid sequence as the amino acid sequence shown by SEQ ID NO:7 or SEQ ID NO:8 (hereinafter the polypeptide containing the same or substantially the same amino acid sequence as the amino acid sequence shown by SEQ ID NO:7 or SEQ ID NO:8 is sometimes collectively referred to as the polypeptide of the present invention) may be any polypeptide derived from any cells of human and other warm-blooded animals (e.g., guinea pig, rat, mouse, chicken, rabbit, swine, sheep, bovine, monkey, etc.) such as liver cells, splenocytes, nerve cells, endocrine cells, neuroendocrine cells, glial cells, β cells of pancreas, bone marrow cells, mesangial cells, Langerhans' cells, epidernic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes, dendritic cells), megakaryocyte, synovial cells, chondrocytes, bone cells, osteoblasts, osteoclasts, mammary gland cells, interstitial cells, etc., the corresponding precursor cells, stem cells, cancer cells, etc., or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, pituitary, stomach, pancreas, kidney, liver, gonad, thyroid, gall-bladder, bone marrow, adrenal gland, skin, muscle, lung, gastrointestinal tract (e.g., large intestine and small intestine), blood vessels, heart, thymus, spleen, submandibular gland, peripheral blood, prostate, testis, ovary, placenta, uterus, bone, cartilage, joint, skeletal muscle, etc.; the polypeptide may also be a recombinant polypeptide or a synthetic polypeptide.

When the polypeptide of the present invention contains a signal peptide, the polypeptide can be efficiently secreted extracellularly.

The amino acid sequence which has substantially the same amino acid sequence as the amino acid sequence represented by SEQ ID NO:7 or SEQ ID NO:8 includes an amino acid sequence having at least about 50% homology, preferably at least about 60% homology, further more preferably at least about 70% homology, much more preferably at least about 80% homology, much more preferably at least about 90% homology, and most preferably at least about 95% homology, to the amino acid sequence represented by SEQ ID NO:7 or SEQ ID NO:8.

The amino acid sequence represented by SEQ ID NO:3 contains both the amino acid sequence represented by SEQ ID NO:7 and the amino acid sequence represented by SEQ ID NO:8.

The amino acid sequence which has substantially the same amino acid sequence as the amino acid sequence represented by SEQ ID NO:3 includes an amino acid sequence having at least about 50% homology, preferably at least about 60% homology, further preferably at least about 70% homology, more preferably at least about 80% homology, much more preferably at least about 90% homology, and most preferably at least about 95% homology, to the amino acid sequence represented by SEQ ID NO:3.

Preferred examples of the polypeptide containing substantially the same amino acid sequence as the amino acid sequence shown by SEQ ID NO:7 or SEQ ID NO:8, are a polypeptide containing substantially the same amino acid sequence as that shown by SEQ ID NO:7 or SEQ ID NO:8 and having an activity substantially equivalent to that of the polypeptide containing the amino acid sequence shown by SEQ ID NO:7 or SEQ ID NO:8, and the like.

More specifically, the amino acid sequence substantially the same amino acid sequence as the amino acid sequence shown by SEQ ID NO:7 includes, for example, the amino acid sequence shown by SEQ ID NO:19 or SEQ ID NO:47, and the like.

More specifically, the amino acid sequence substantially the same amino acid sequence as the amino acid sequence shown by SEQ ID NO:8 includes, for example, the amino acid sequence shown by SEQ ID NO:21 or SEQ ID NO:49, and the like.

Preferred examples of the polypeptide which contains substantially the same amino acid sequence as that shown by SEQ ID NO:3 are a polypeptide containing substantially the same amino acid sequence as that shown by SEQ ID NO:3 and having an activity substantially equivalent to that of the polypeptide containing the amino acid sequence shown by SEQ ID NO:3, and the like.

Specific examples of the amino acid sequence substantially the same amino acid sequence as the amino acid sequence shown by SEQ ID NO:3 are the amino acid sequence shown by SEQ ID NO:17, SEQ ID NO:23, SEQ ID NO:45 or SEQ ID NO:51, etc.

The substantially equivalent activity includes, for example, an antigenic activity, an activity of functioning to be a humoral factor after secretion, an intracellular cyclic AMP production promoting activity, and the like. The term substantially equivalent means that the activity is equivalent qualitatively. Thus, the properties such as a secretory activity, solubility, a physiological activity, etc. are preferably equivalent in strength (e.g., about 0.1 to about 100 times, about 0.5 to about 10 times, more preferably about 0.5 to about 2 times), and even quantitative differences such as the strength of these activities, molecular weight of polypeptides, etc. may be present.

Specific examples of the polypeptide containing substantially the same amino acid sequence as the amino acid sequence shown by SEQ ID NO:7, SEQ ID NO:8 or SEQ ID NO:3 include so-called muteins such as polypeptides containing (i) an amino acid sequence represented by SEQ ID NO:7, SEQ ID NO:8 or SEQ ID NO:3, of which one, two, or more amino acids (preferably approximately 1 to 30, more preferably approximately 1 to 10, and most preferably several (1 to 5)) amino acids are deleted; (ii) an amino acid sequence represented by SEQ ID NO:7, SEQ ID NO:8 or SEQ ID NO:3, to which one, two, or more amino acids (preferably approximately 1 to 30, more preferably approximately 1 to 10, and most preferably several (1 to 5)) amino acids are added; (iii) an amino acid sequence represented by SEQ ID NO:7, SEQ ID NO:8 or SEQ ID NO:3, into which one, two, or more amino acids (preferably approximately 1 to 30, more preferably approximately 1 to 10, and most preferably several (1 to 5)) amino acids are inserted; (iv) an amino acid sequence represented by SEQ ID NO:7, SEQ ID NO:8 or SEQ ID NO:3, in which one, two, or more amino acids (preferably approximately 1 to 30, more preferably approximately 1 to 10, and most preferably several (1 to 5)) amino acids are substituted by other amino acids; and (v) a combination of the above amino acid sequences; and the like.

When an amino acid sequence(s) are inserted, deleted or substituted as described above, the positions of such insertion, deletion or substitution are not particularly limited, and such amino acid residues are those other than cysteine residue in the amino acid sequences shown by each sequencing identification number of SEQ ID NO:7, SEQ ID NO:8 or SEQ ID NO:3.

The polypeptide containing the same or substantially the same amino acid sequence as the amino acid sequence shown by SEQ ID NO:7 or the polypeptide containing the same or substantially the same amino acid sequence as the amino acid sequence shown by SEQ ID NO:8 further includes, in addition to a single chain polypeptide containing both the amino acid sequence shown by SEQ ID NO:7 and the amino acid sequence shown by SEQ ID NO:8, a polypeptide composed of 2 polypeptide chains (hereinafter sometimes simply referred to as 2 chain-polypeptide in the present specification) of a polypeptide containing the same or substantially the same amino acid sequence as the amino acid sequence shown by SEQ ID NO:7 (hereinafter sometimes simply referred to as the A chain in the present specification) and the polypeptide containing the same or substantially the same amino acid sequence as the amino acid sequence shown by SEQ ID NO:8 (hereinafter sometimes simply referred to as the B chain in the present specification).

More specifically, the 2 chain-polypeptide means a polypeptide wherein the same or substantially the same amino acid sequence as the amino acid sequence shown by SEQ ID NO:7 and the same or substantially the same amino acid sequence as the amino acid sequence shown by SEQ ID NO:8 are bound through disulfide bonds, and refers to a polypeptide that the cysteine residues in the A and B chains form the intermolecular and intramolecular disulfide bonds. For the pair of bonds between the cysteine residues, it is particularly desired to bind, e.g., Cys11 of the A chain (Cys11 of the A chain indicates the 11th cysteine residue from the N terminus of the amino acid sequence represented by SEQ ID NO:7, SEQ ID NO:19 or SEQ ID NO:47; hereinafter the same) and Cys10 of the B chain (Cys10 of the B chain indicates the 10th cysteine residue from the N terminus of the amino acid sequence represented by SEQ ID NO:8, SEQ ID NO:21 or SEQ ID NO:49; hereinafter the same), and bind Cys24 of the A chain and Cys22 of the B chain, and further bind Cys10 of the A chain and Cys5 of the A chain.

For the polypeptide containing the same or substantially the same amino acid sequence as the amino acid sequence represented by SEQ ID NO:3 (hereinafter sometimes simply referred to as the precursor protein), polypeptides preferably:

(1) in the case of SEQ ID NO:3, contain the amino acid sequence shown by SEQ ID NO:8 (i.e., the amino acid sequence encoding the B chain) in the 26 (Arg) to 52 (Trp) from the N terminus and contain the amino acid sequence shown by SEQ ID NO:7 (i.e., the amino acid sequence encoding the A chain) in the 119 (Asp) to 142 (Cys) from the N terminus of SEQ ID NO:3;

(2) in the case of SEQ ID NO:17, contain the amino acid sequence shown by SEQ ID NO:21 (i.e., the amino acid sequence encoding the B chain) in the 25 (Arg) to 51 (Trp) from the N terminus and contain the amino acid sequence shown by SEQ ID NO:19 (i.e., the amino acid sequence encoding the A chain) in the 118 (Asp) to 141 (Cys) from the N terminus of SEQ ID NO:17;

(3) in the case of SEQ ID NO:23, contain the amino acid sequence shown by SEQ ID NO:21 (i.e., the amino acid sequence encoding the B chain) in the 24 (Arg) to 50 (Trp) from the N terminus and contain the amino acid sequence shown by SEQ ID NO:19 (i.e., the amino acid sequence encoding the A chain) in the 117 (Asp) to 140 (Cys) from the N terminus of SEQ ID NO:23;

(4) in the case of SEQ ID NO:45, contain the amino acid sequence shown by SEQ ID NO:49 (i.e., the amino acid sequence encoding the B chain) in the 27 (Arg) to 53 (Trp) from the N terminus and contain the amino acid sequence shown by SEQ ID NO:47 (i.e., the amino acid sequence encoding the A chain) in the 117 (Asp) to 140 (Cys) from the N terminus of SEQ ID NO:23;

(5) in the case of SEQ ID NO:51, contain the amino acid sequence shown by SEQ ID NO:21 (i.e., the amino acid sequence encoding the B chain) in the 24 (Arg) to 50 (Trp) from the N terminus and contain the amino acid sequence shown by SEQ ID NO:19 (i.e., the amino acid sequence encoding the A chain) in the 151 (Asp) to 174 (Cys) from the N terminus of SEQ ID NO:19; and thus possess the property as the 2 chain-polypeptides having the A and B chains.

Throughout the present specification, the polypeptides (hereinafter the chain A, chain B, 2 chain-polypeptide and precursor protein are sometime collectively referred to as "polypeptide of the present invention") are represented in accordance with the conventional way of describing polypeptides, that is, the N-terminus (amino terminus) at the left hand and the C-terminus (carboxyl terminus) at the right hand. In the polypeptides of the present invention including the polypeptide containing the amino acid sequence shown by SEQ ID NO:3, SEQ ID NO:7 or SEQ ID NO:8, the C-terminus is usually in the form of a carboxyl group (—COOH) or a carboxylate (—COO$^-$) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like which is used widely as an ester for oral administration may also be used.

Where the polypeptide of the present invention contains a carboxyl group (or a carboxylate) at a position other than the C-terminus, it may be amidated or esterified and such an amide or ester is also included within the polypeptide of the present invention. As the ester group herein, the same esters as those described with respect to the above C-terminal are used.

Furthermore, examples of the polypeptide of the present invention include variants of the above polypeptides, wherein the amino group at the N-terminus (e.g., methionine residue) of the polypeptide is protected with a protecting group (e.g., a $C_{1-6}$ acyl group such as a $C_{1-6}$ alkanoyl group e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains.

The polypeptide of the present invention may be a monomer or a polymer such as a dimer, a tetramer, a hexamer, an octamer, etc.

The polypeptide of the present invention or its salt may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide of the present invention or salts thereof may be produced by a publicly known method used to purify a polypeptide (protein) from human or other warm-blooded animal cells or tissues described above, or may also be manufactured by culturing a transformant containing DNA encoding the polypeptide later described. Furthermore, the polypeptide of the present invention or salts thereof may also be manufactured by a modification of the peptide synthesis method, which will be described below.

Where the polypeptides of the present invention are produced from human or mammalian tissues or cells, human or mammalian tissues or cells are homogenized, then extracted with an acid or the like, and the extract is isolated and purified by a combination of chromatography techniques such as reversed phase chromatography, ion exchange chromatography, and the like.

To synthesize the polypeptide of the present invention, or its salts or amides, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptide or amides thereof.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide (protein) condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to polypeptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$—Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups, activation of functional groups involved in the reaction, etc. may be appropriately selected from publicly known groups and publicly known means.

In another method of obtaining the amides of the polypeptide, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group has been eliminated from the polypeptide and a polypeptide in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired polypeptide.

To prepare the esterified polypeptide, for example, the a-carboxyl group of the carboxy terminal amino acid is condensed with a desired alcohol to prepare the amino acid ester, which is followed by procedure similar to the preparation of the amidated polypeptide above to give the desired esterified polypeptide.

The polypeptide or its salts of the present invention can be manufactured by publicly known methods for peptide synthesis. For the methods for peptide synthesis, for example, either solid phase synthesis or liquid phase synthesis may be used. That is, the partial peptide or amino acids that can construct the partial peptide of the present invention are condensed with the remaining part. Where the product contains protecting groups, these protecting groups are removed to give the desired peptide. Publicly known methods for condensation and elimination of the protecting groups are described in (1)–(5) below.

(1) M. Bodanszky & M. A. Ondetti: Peptide Synthesis, Interscience Publishers, New York (1966)

(2) Schroeder & Luebke: The Peptide, Academic Press, New York (1965)

(3) Nobuo Izumiya, et al.: Peptide Gosei-no-Kiso to Jikken (Basics and experiments of peptide synthesis), published by Maruzen Co. (1975)

(4) Haruaki Yajima & Shunpei Sakakibara: Seikagaku Jikken Koza (Biochemical Experiment) 1, Tanpakushitsu no Kagaku (Chemistry of Proteins) IV, 205 (1977)

(5) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the polypeptide of the present invention. When the polypeptide obtained by the above methods is in a free form, the polypeptide can be converted into an appropriate salt by a publicly known method; when the polypeptide is obtained in a salt form, it can be converted into a free form or a different salt form by a publicly known method.

The DNA encoding the polypeptide of the present invention may be any DNA so long as it contains the base sequence encoding the polypeptide of the present invention described above. Such a DNA may also be any one of genomic DNA, cDNA derived from the cells or tissues described above, and synthetic DNA.

The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

Specifically, the DNA encoding the polypeptide of the present invention may be any one of, for example, a DNA having the base sequence represented by SEQ ID NO:12, SEQ ID NO:15, SEQ ID NO:16, SEQ ID NO:18, SEQ ID NO:20, SEQ ID NO:22, SEQ ID NO:24, SEQ ID NO:25, SEQ ID NO:26, SEQ ID NO:46, SEQ ID NO:48, SEQ ID NO:50 or SEQ ID NO:52; or any DNA containing a DNA having a base sequence hybridizable to the base sequence represented by SEQ ID NO:12, SEQ ID NO:15, SEQ ID NO:16, SEQ ID NO:18, SEQ ID NO:20, SEQ ID NO:22, SEQ ID NO:24, SEQ ID NO:25, SEQ ID NO:26, SEQ ID NO:46, SEQ ID NO:48, SEQ ID NO:50 or SEQ ID NO:52 under high stringent conditions and encoding a polypeptide having an activity substantially equivalent to that of the polypeptide of the present invention (e.g., an biological activity, an antigenic activity, an activity as a humoral factor after secretion, an intracellular cyclic AMP production promoting activity, etc.), and a DNA encoding a polypeptide which has an activity substantially equivalent to that of the polypeptide of the present invention.

Specific examples of the DNA that is hybridizable to the base sequence represented by SEQ ID NO:12, SEQ ID NO:15, SEQ ID NO:16, SEQ ID NO:18, SEQ ID NO:20, SEQ ID NO:22, SEQ ID NO:24, SEQ ID NO:25, SEQ ID NO:26, SEQ ID NO:46, SEQ ID NO:48, SEQ ID NO:50 or SEQ ID NO:52 under high stringent conditions include DNA having at least about 60% homology, preferably at least about 70% homology, more preferably at least about 80% homology, to the base sequence represented by SEQ ID NO:12, SEQ ID NO:15, SEQ ID NO:16, SEQ ID NO:18, SEQ ID NO:20, SEQ ID NO:22, SEQ ID NO:24, SEQ ID NO:25, SEQ ID NO:26, SEQ ID NO:46, SEQ ID NO:48, SEQ ID NO:50 or SEQ ID NO:52.

Specific examples of the DNA hybridizable to the base sequence represented by SEQ ID NO:12, SEQ ID NO:15, SEQ ID NO:16, SEQ ID NO:18, SEQ ID NO:20, SEQ ID NO:22, SEQ ID NO:24, SEQ ID NO:25, SEQ ID NO:26, SEQ ID NO:46, SEQ ID NO:48, SEQ ID NO:50 or SEQ ID NO:52 under high stringent conditions, include a DNA containing a DNA encoding a polypeptide which has an activity substantially equivalent to that of the polypeptide of the present invention (e.g., an biological activity, an antigenic activity, an activity as a humoral factor after secretion, an intracellular cyclic AMP production promoting activity, etc.) and has an activity substantially equivalent to that of the polypeptide of the present invention, and the like.

The hybridization can be carried out by publicly known methods or by a modification thereof, for example, according to the method described in Molecular Cloning, 2nd Ed., J. Sambrook et al., Cold Spring Harbor Lab. Press, (1989). A commercially available library may also be used according to the instructions of the attached manufacturer's protocol. The hybridization can be carried out preferably under high stringent conditions.

The high stringent conditions used herein are, for example, those in a sodium concentration at about 19 mM to about 40 mM, preferably about 19 mM to about 20 mM at a temperature of about 50° C. to about 70 C, preferably about 60 C to about 65° C.

For the DNA encoding the polypeptide of the present invention, there may be employed a DNA having the base sequence represented by SEQ ID NO:12, SEQ ID NO:15, SEQ ID NO:16, SEQ ID NO:18, SEQ ID NO:20, SEQ ID NO:22, SEQ ID NO:24, SEQ ID NO:25, SEQ ID NO:26, SEQ ID NO:46, SEQ ID NO:48, SEQ ID NO:50 or SEQ ID NO:52, or the like.

More specifically, the following examples are given for the DNA:

(I) for the DNA encoding the A chain (human type: a polypeptide containing the amino acid sequence shown by SEQ ID NO:7), there are, e.g., a DNA containing a DNA having the base sequence shown by SEQ ID NO:15;

(II) for the DNA encoding the A chain (rat type: a polypeptide containing the amino acid sequence shown by SEQ ID NO:19), there are, e.g., a DNA containing a DNA having the base sequence shown by SEQ ID NO:20;

(III) for the DNA encoding the A chain (mouse type: a polypeptide containing the amino acid sequence shown by SEQ ID NO:19), there are, e.g., a DNA containing a DNA having the base sequence shown by SEQ ID NO:25;

(IV) for the DNA encoding the A chain (porcine type: a polypeptide containing the amino acid sequence shown by SEQ ID NO:47), there are, e.g., a DNA containing a DNA having the base sequence shown by SEQ ID NO:48;

(V) for the DNA encoding the B chain (human type: a polypeptide containing the amino acid sequence shown by SEQ ID NO:8), there are, e.g., a DNA containing a DNA having the base sequence shown by SEQ ID NO:16;

(VI) for the DNA encoding the B chain (rat type: a polypeptide containing the amino acid sequence shown by SEQ ID NO:21), there are, e.g., a DNA containing a DNA having the base sequence shown by SEQ ID NO:22;

(VII) for the DNA encoding the B chain (mouse type: a polypeptide containing the amino acid sequence shown by SEQ ID NO:21), there are, e.g., a DNA containing a DNA having the base sequence shown by SEQ ID NO:26;

(VIII) for the DNA encoding the B chain (porcine type: a polypeptide containing the amino acid sequence shown by SEQ ID NO:49), there are, e.g., a DNA containing a DNA having the base sequence shown by SEQ ID NO:50;

(IX) for the DNA encoding the 2 chain-polypeptide (human type) and the precursor protein (human type: a polypeptide containing the amino acid sequence shown by SEQ ID NO:3), there are, e.g., a DNA containing a DNA having the base sequence shown by SEQ ID NO:12;

(X) for the DNA encoding 2 chain-polypeptide (rat type) and the precursor protein (rat type: a polypeptide containing the amino acid sequence shown by SEQ ID NO:17 or SEQ ID NO:51), there are, e.g., a DNA containing a DNA having the base sequence shown by SEQ ID NO:18 or 52;

(XI) for the DNA encoding 2 chain-polypeptide (mouse type) and the precursor protein (mouse type: a polypeptide containing the amino acid sequence shown by SEQ ID NO:23), there are, e.g., a DNA containing a DNA having the base sequence shown by SEQ ID NO:24;

(XII) for the DNA encoding 2 chain-polypeptide (porcine type) and the precursor protein (porcine type: a polypeptide containing the amino acid sequence shown by SEQ ID NO:45), there are, e.g., a DNA containing a DNA having the base sequence shown by SEQ ID NO:46; and the like.

For cloning of the DNA that completely encodes the polypeptide of the present invention, the DNA may be either amplified by publicly known PCR using synthetic DNA primers containing a part of the base sequence of the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989). The hybridization may also be performed using commercially available library in accordance with the protocol described in the attached instructions.

Conversion of the base sequence of DNA can be effected by publicly known methods such as the ODA-LA PCR method, the Gupped duplex method, the Kunkel method, etc., using PCR or a publicly known kit available as Mutan (trademark)-super Express Km (manufactured by Takara Shuzo Co., Ltd.) Mutan(trademark)-K (manufactured by Takara Shuzo Co., Ltd.), etc.

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be produced, for example, by (a) excising the objective DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1–11, pXT1, pRc/CMV, pRc/RSV, pcDNAI/Neo, pET-1, pET-2, pET-3, pET-4, pET-5, pET-11, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, β-actin promoter, etc.

Among them, CMV (cytomegalovirus) promoter, SRα promoter, β-actin promoter, etc. are preferably used. Where the host is bacteria of the genus *Escherichia,* preferred examples of the promoter include trp promoter, lac promoter, recA promoter, λPL promoter, lpp promoter, T7 promoter, etc. In the case of using bacteria of the genus Bacillus as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

Where the T7 promoter expression system is employed, any one of 17 promoters found on T7 DNA [J. L. Oakley, et al., Proc. Natl. Acad. Sci. USA, 74: 4266–4270 (1977), M.D. Rosa, Cell 16: 815–825 (1979), N. Panayotatos, et al., Nature, 280:35 (1979), J. J. Dunn, et al., J. Mol. Biol., 166: 477–535 (1983)] is usable as T7 promoter, but preferred is φ10 promoter [A. H. Rosenberg, et al., Gene, 56; 125–135 (1987)].

It is preferred to construct a vector by incorporating T7 promoter and T7 terminator into the vector described above, and such a vector includes pET-1, pET-2, pET-3, pET-4, pEt-5, pET-111 [A. H. Rosenberg, Gene, 56: 125–135 (1987)], etc.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, Geneticin resistance), etc. In particular, when dhfr gene is used as the selection marker together with dhfr gene of Chinese hamster's cells, selection can also be made on thymidine free media.

If necessary, a signal sequence that matches with a host is added to the N-terminus of the polypeptide of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MF α signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector bearing the DNA that encodes the polypeptide of the present invention thus constructed, transformants can be produced.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)), JM103 (Nucleic Acids Research, 9, 309 (1981)], JA221 [Journal of Molecular Biology, 120, 517 (1978)), HB101 [Journal of Molecular Biology, 41, 459 (1969)], C600 (Genetics, 39, 440 (1954)], etc.

When using the T7 promoter system, *Escherichia coli* strain incorporated with the T7 RNA polymerase gene [F. W. Studier, et al., J. Mol. Biol., 189: 113–130 (1986)], e.g., MM294, DH-1, C600, JM109, BL21, or *Escherichia coli* strain incorporated with the T7 RNA polymerase gene together with another plasmid, etc. are employed for the host of the transformant. It is preferred to use the MM294 strain, BL21 strain and BL21(DE3) strain, resulting from lysogenization of a λ phage incorporating the T7 RNA polymerase gene, and the like. In this case, the lac promoter, which induces expression in the presence of isopropyl-1-thio-β-D-galacto-pyranoside (IPTG), is used as a promoter for the T7 RNA polymerase gene.

Examples of the bacteria belonging to the genus *Bacillus* include *Bacillus subtilis* MI114 [Gene, 24, 255 (1983)], 207–21 [Journal of Biochemistry, 95, 87 (1984)], etc.

Examples of yeast include *Saccharomyces cereviseae* AH22, AH22R$^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell, which can be used, are Sf9 cell (ATCC CRL1711), Sf21 cell (both cells are described in Vaughn, J. L. et al., In Vivo, 13, 213–217 (1977)), etc.

As the insect, for example, a larva of *Bombyx mori*, etc. can be used [Maeda et al., Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as CHO (dhfr$^-$) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics; 168, 111 (1979), etc.

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in Saibo Kogaku (Cell Engineering), extra issue 8, *Shin Saibo Kogaku Jikken Protocol* (New Cell Engineering Experimental Protocol), 263–267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, yeast extract, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as 10% immobilized bovine serum is added. Preferably, pH of the medium is adjusted to about 6.2 to 6.4. Normally, the transformant is cultivated at about 27° C. for about 3 to 5 days and, if necessary, the culture can be aerated or agitated.

Where animal cells are employed as the host, the transformant is cultivated in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30 to 40° C. for about 15 to 60 hours and, if necessary, the culture can be aerated or agitated.

As described above, the polypeptide of the present invention can be produced in the transformant, intracellularly, on the cell membrane or extracellularly.

The polypeptide of the present invention can be separated and purified from the culture described above by the following procedures.

When the polypeptide of the present invention is extracted from the culture or cells, the following procedures are appropriately used, namely, after cultivation the transformants or cells are collected by a publicly known method and suspended in a appropriate buffer. The transformants or cells are then disrupted by publicly known methods such as ultrasonication, a treatment with lysozyme and/or freeze-thaw cycling, etc., followed by centrifugation, filtration, etc. to obtain the crude extract of the polypeptide. When the polypeptide produced by the recombinant forms an inclusion body in the cells, the cells are collected by centrifugation and then disrupted by ultrasonication, etc. The resulting inclusion body is solubilized using a modifier (2 to 8 M guanidine hydrochloride or 5 to 9 M urea, etc.) so that the polypeptide can be extracted. When the polypeptide is secreted in the culture broth, after completion of the cultivation the supernatant can be separated from the transformants or cells by a publicly known method to collect the supernatant.

The polypeptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charges such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein-modifying enzyme so that the polypeptide can be appropriately modified to partially remove a polypeptide. For the protein-modifying enzyme, there is used trypsin, chymotrypsin, arginyl endopeptidase, furin, prohormone convertase 1 (PC1), prohormone convertase 2 (PC2), carboxypeptidase B, protein kinase, glycosidase, or the like. Examples of chemical reactions include cleavage using cyanogen bromide (CNBr), etc The objective protein extracted or the objective protein separated and purified is subjected to refolding of protein, if necessary. Refolding can be performed by publicly known methods, e.g., as described in “Folding of Protein,” (edited by R. H. Pain, 245–279 (1995), Springer Verlag, Tokyo), or its modifications. Refolding may be effected in a buffer free of any extracting agent (e.g., a chaotropic solubilizer such as guanidine hydrochloride or urea, a surfactant such as n-laurylmethylglycine or SDS, etc.), or containing a low level of such an extracting agent, through one-step or multi-step dilution, or by dialysis using a semipermeable membrane, buffer exchange using gel filtration, or the like. In this case, arginine, polyethylene glycol, a neutral surfactant, etc. may be incorporated to prevent aggregation of the objective protein. In order to form disulfide bonds of proteins, air oxidation may be carried out, or the redox buffer system, etc. may be added. Examples of the redox buffer include glutathione, cysteine, dithiothreitol, 2-mercaptoethano, or a cysteamine-based buffer.

Also, the A and B chains, which are included in the polypeptide of the present invention, may be produced independently to couple the two through disulfide bonds. For example, DNA fragments encoding the A and B chains are bound, respectively, to lacZ (β-galactosidase) gene to produce a fused protein of β-galactosidase+the A chain and β-galactosidase+the B chain using *E. coli* as a host; then, the A and B chains can be excised out of the fused protein by the cyanogen bromide treatment or the enzyme treatment. The excised A and B chains are mixed with each other in a reduced state and the mixture is gradually oxidized, whereby the mixture can be converted into a protein of the A and B chains bound via disulfide bonds. The binding state of the A and B chains is preferably the binding between Cys11 of the A chain and Cys10 of the B chain, and between Cys24 of the A chain and Cys22 of the B chain and further between Cys10 of the A chain and Cys15 of the A chain. The exchange conditions in this case are made by a modification of the process for producing insulin molecules [Proc. Natl. Acad. Sci. USA, 76, 106 (1979)].

The presence of the thus produced polypeptide of the present invention or its salt can be determined by enzyme immunoassay using specific antibodies or western blotting analysis, etc.

The antibodies to the polypeptide of the present invention, its amide or esters, or salts thereof (hereinafter sometimes merely referred to as the polypeptide of the present invention) may be either polyclonal antibodies or monoclonal antibodies, so long as they are capable of recognizing the polypeptide of the present invention.

The antibodies to the polypeptide of the present invention may be manufactured by publicly known methods for manufacturing antibodies or antisera, using as antigens the polypeptide of the present invention.

[Preparation of Monoclonal Antibody]

(a) Preparation of Monoclonal Antibody-producing Cells

The polypeptide of the present invention is administered to warm-blooded animals either solely or together with carriers or diluents to the site where the antibody production is possible by the administration. In order to potentiate the antibody productivity upon the administration, complete Freund’s adjuvants or incomplete Freund’s adjuvants may be administered. The administration is usually carried out once every 2 to 6 weeks and 2 to 10 times in total. Examples of the applicable warm-blooded animals are monkeys, rabbits, dogs, guinea pigs, mice, rats, sheep, goats and chicken, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein (Nature, 256, 495, 1975). Examples of the fusion promoter are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at about 20 to 40° C., preferably at about 30 to 37° C. for about 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the polypeptide as an antigen directly or together with a carrier, adding an anti-immunoglobulin antibody (where mouse cells are used for the cell fusion, anti-mouse immunoglobulin antibody is used) labeled with a radioactive substance or an enzyme or protein A and detecting the monoclonal antibody bound to the solid phase, a method which comprises adding the culture supernatant of hybridoma to a solid phase adsorbed with an anti-immunoglobulin antibody or protein A, adding the polypeptide labeled with a radioactive substance or an enzyme and detecting the monoclonal antibody bound to the solid phase, and the like.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing about 1 to 20%, preferably about 10 to 20% fetal bovine serum, GIT medium (Wako Pure Chemical Industries, Ltd.) containing about 1 to 10% fetal bovine serum, a serum free medium for cultivation of a hybridoma (SFM-101, Nissui Seiyaku Co., Ltd.) and the like can be used for the selection and growth medium. The cultivation is carried out generally at about 20 to 40° C., preferably at about 37° C., for 5 days to 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, protein A or Protein G and dissociating the binding to obtain the antibody].

[Preparation of Polyclonal Antibody]

The polyclonal antibody of the present invention can be manufactured by publicly known methods or modifications thereof. For example, a warm-blooded animal is immunized with an immunogen (polypeptide antigen of the present invention) per se, or a complex of immunogen and a carrier protein is formed and a warm-blooded animal is immunized with the complex in a manner similar to the method described above for the manufacture of monoclonal antibodies. The product containing the antibody to the polypeptide of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin, hemocyanin, etc. is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group, and the like are used for the coupling.

The condensation product is administered to warm-blooded animals either solely or together with carriers or diluents to the site that can produce the antibody. In order to potentiate the antibody productivity upon the administration, complete Freund's adjuvant or incomplete Freund's adjuvant may be administered. The administration is usually made once every about 2 to 6 weeks and approximately 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as used for the determination of serum antibody titer described above. The separation and purification of the polyclonal antibody can be carried out, following the method for the separation and purification of immunoglobulins performed as in the separation and purification of monoclonal antibodies described hereinabove.

Also, using the polypeptide of the present invention, humanized antibodies can be produced by modifications of the methods described in Nat. Biotechnol., 14, 845–851 (1996), Nat. Genet., 15, 146–156 (1997), PNAS, 97 (2), 722–727 (2000), etc.

The antisense DNA having a complementary or substantial complementary base sequence to the DNA encoding the polypeptide of the present invention (hereinafter sometimes referred to as the DNA of the present invention) can be any antisense DNA, so long as it possesses a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). Particularly in the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal site of the polypeptide of the present invention (e.g., the base sequence around the initiation codon). These antisense DNAs can be synthesized using publicly known DNA synthesizers, etc.

When the polypeptide of the present invention contains a signal peptide, the polypeptide can be efficiently secreted outside the cells and exhibits important biological activities including the regulation of biological functions, etc., as a humoral factor.

Hereinafter, the polypeptide of the present invention, the DNA of the present invention, the antibodies to the polypeptide of the present invention or salts thereof (hereinafter sometimes merely referred to as the antibody of the present invention) and antisense DNA are explained in terms of their use.

(1) The polypeptide of the present invention is expressed tissue-specifically and can thus be employed as a tissue marker. That is, the polypeptide of the present invention is useful as a marker for detecting the differentiation of tissues, disease symptoms, cancer metastasis, etc. The polypeptide is also available for fractionation of the corresponding receptors, binding polypeptides, etc. The polypeptide is further available for investigations of biological activities by preparing panels for high throughput screening publicly known.

(2) Therapeutic/prophylactic agent for various diseases, with which the polypeptide of the present invention is associated The polypeptide of the present invention is present in vivo as a humoral factor and has the activity of promoting the expression of MMP-1 (matrix metalloprotease-1) or VEGF (vascular endothelial growth factor), as given in EXAMPLES later described. Thus, when the polypeptide of the present invention or the DNA of the present invention, etc. are found to be abnormal or deficient, or when their expression levels are abnormally reduced or enhanced, various diseases are caused, including abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, or the like. Therefore, the polypeptide of the present invention and the DNA of the present invention can be used as pharmaceuticals for the treatment/prevention of various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, or the like.

The polypeptide of the present invention forms a family with other insulin/IGF/relaxin family polypeptides. Thus, when the polypeptide of the other family or its DNA, etc. are found to be abnormal or deficient, or when their expression levels are abnormally reduced or enhanced, the polypeptide of the present invention can act complementarily with the other family, or even when any particular abnormality is not noted in the expression level, the polypeptide of the present invention can act based on its own pharmacological activity, the polypeptide of the present invention can be used as pharmaceuticals for the treatment/prevention of various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), endocrine disruption, abnormality of body fluid balance, central diseases, immune system diseases (e.g., allergy, inflammation, autoimmune disease, etc.), angiogenic disorders, or the like.

Furthermore, although it is preferred to form the polypeptide of the present invention by 1 pair of the disulfide bonds in the A chain and 2 pairs of the disulfide bonds between the A and B chains, as described above, molecular species of the A chain alone having 2 pairs of disulfide bonds or the B chain alone having 1 pair of disulfide bonds are also available. These molecular species of the later A chain or B chain alone can also be used as pharmaceuticals for the treatment/prevention of various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, or the like.

When a patient has a reduced level of, or deficient of the polypeptide of the present invention in his or her body so that signal transduction is not made sufficiently or properly in cells, the polypeptide of the present invention can provide its role sufficiently or properly for the patient, (a) by administering the DNA of the present invention to the patient to express the polypeptide of the present invention in vivo, (b) by inserting the DNA of the present invention into a cell, expressing the polypeptide of the present invention and then transplanting the cell to the patient, (c) by administering the polypeptide of the present invention to the patient, or the like.

Where the DNA of the present invention is used as the prophylactic/therapeutic agent described above, the DNA itself is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as an intact DNA, or prepared into pharmaceutical preparations together with physiologically acceptable carriers such as adjuvants to assist its uptake, which are administered by gene gun or through a catheter such as a hydrogel catheter.

Where the polypeptide of the present invention is used as the aforesaid therapeutic/prophylactic agents, the polypeptide or the protein is advantageously used on a purified level of at least 90%, preferably at least 95%, more preferably at least 98% and most preferably at least 99%. The polypeptide of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given. Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include vegetable oil such as olive oil, sesame oil, soybean oil, peanut oil, cotton seed oil, corn oil, etc., propylene glycol, etc., which may also be used in combination with a dissolution aid such as benzyl benzoate, benzyl alcohol, etc. The polypeptide of the present invention may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally. Since the thus obtained pharmaceutical preparation is safe and low toxic, and can be administered to, for example, warm-blooded animals (e.g., human, rat, mouse, guinea pig, rabbit, chicken, sheep, swine, bovine, horse, cat, dog, monkey, etc.).

The dose of the polypeptide of the present invention may vary depending on target disease, subject to be administered, route for administration, etc. When the polypeptide of the present invention is orally administered for the purpose of treating various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., the polypeptide of the present invention is administered to adult (as 60 kg) generally in a daily dose of approximately 0.01 mg to 1000 mg, preferably approximately 1 mg to 1000 mg, more preferably approximately 10 to 500 mg, and most preferably approximately 10 to 200 mg. When the polypeptide of the present invention is parenterally administered, a single dose of the polypeptide of the present invention may vary depending on subject to be administered, target disease, etc. When the polypeptide of the present invention is administered to adult (as 60 kg body weight) in the form of injection for the purpose of treating various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., it is desired to administer the polypeptide either by local injection to the affected area or systemic injection, generally in a daily dose of approximately 0.001 to 500 mg, preferably approximately 0.01 to 500 mg, more preferably approximately 0.1 to 200 mg, and most preferably approximately 0.1 to 100 mg. For other animal species, the corresponding dose as converted per 60 kg weight can be administered.

(2) Screening of Drug Candidate Compounds for Disease

Since the polypeptide of the present invention is present in vivo as a humoral factor, the compounds or salts thereof that promote the functions (activities) of the polypeptide of the present invention can be used as pharmaceuticals for the treatment/prevention of various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, or the like.

On the other hand, compounds or salts thereof that inhibit the functions (activities) of the polypeptide of the present invention can be used as pharmaceuticals for the treatment/prevention, etc. of diseases caused by excessive production of the polypeptide of the present invention.

Thus, the polypeptide of the present invention is useful as a reagent for screening the compounds or salts thereof that promote or inhibit the functions (activities) of the polypeptide of the present invention.

That is, the present invention provides:

(1) a method of screening the compounds or salts thereof that promote the functions (activities) of the polypeptide of the present invention, which comprises using the polypeptide of the present invention or salts thereof (hereinafter sometimes merely referred to as the promoter), or the compounds or salts thereof that inhibit the functions (activities) of the polypeptide of the present invention (hereinafter sometimes merely referred to as the inhibitor).

The screening kit of the present invention comprises the polypeptide of the present invention or a salt thereof.

Specifically, the method of screening the compounds or salts thereof that promote or inhibit the functions (activities) of the polypeptide of the present invention, characterized by using the polypeptide of the present invention includes:

a method of screening the compounds that alter the binding property between the polypeptide of the present invention and tissues, cells or membrane fractions thereof (the compounds that promote or inhibit the activities of the polypeptide of the present invention), or salts thereof, which comprises comparing (i) the case when the polypeptide of the present invention is brought in contact with tissues, cells or membrane fractions thereof, to which the polypeptide of the present invention is bound, and (ii) the case when the polypeptide of the present invention and a test compound are brought in contact with tissues, cells or membrane fractions thereof, to which the polypeptide of the present invention is bound; etc.

In the screening method of the present invention, a ligand binding amount, a cell stimulating activity, a tissue reactivity, or the like, to the tissues, cells or membrane fractions thereof to which the polypeptide of the present invention is bound, are measured (i) when the polypeptide of the present invention is brought in contact with the tissues, cells or membrane fractions thereof, to which the polypeptide of the present invention is bound, and (ii) when the polypeptide of the present invention and a test compound are brought in contact with the tissues, cells or membrane fractions thereof, to which the polypeptide of the present invention is bound, and (i) and (ii) are compared.

Specifically, the screening method of the present invention includes:

(1) a method of screening the compounds that alter the binding property between the polypeptide of the present invention and the tissues, cells or membrane fractions thereof to which the polypeptide of the present invention is bound (the compounds that promote or inhibit the activities of the polypeptide of the present invention), or salts thereof, which comprises measuring and comparing the binding amount of a labeled form of the polypeptide of the present invention to the tissues, cells or membrane fractions thereof to which the polypeptide of the present invention is bound, when the labeled polypeptide of the present invention is brought in contact with the tissues, cells or membrane fractions thereof to which the polypeptide of the present invention is bound, and when the labeled polypeptide of the present invention and a test compound are brought in contact with the tissues, cells or membrane fractions thereof to which the polypeptide of the present invention is bound;

(2) a method of screening the compounds that alter the binding property between the polypeptide of the present invention and a receptor to the polypeptide of the present invention (the compounds that promote or inhibit the activities of the polypeptide of the present invention), or salts thereof, which comprises measuring and comparing the binding amount of a labeled form of the polypeptide of the present invention to a cell containing the receptor to the polypeptide of the present invention or a membrane fraction of the cell, when the labeled polypeptide of the present invention is brought in contact with the cell or membrane fraction, and when the labeled polypeptide of the present invention and a test compound are brought in contact with the cell or membrane fraction;

(3) a method of screening the compounds that alter the binding property between the polypeptide of the present invention and a receptor to the polypeptide of the present invention (the compounds that promote or inhibit the activities of the polypeptide of the present invention), or salts thereof, which comprises measuring and comparing the binding amount of a labeled form of the polypeptide of the present invention to the receptor to the polypeptide of the present invention, when the labeled polypeptide of the present invention is brought in contact with the receptor to the polypeptide of the present invention expressed on a cell membrane by culturing the transformant bearing the DNA encoding the receptor to the polypeptide of the present invention, and when the labeled polypeptide of the present invention and a test compound are brought in contact with the receptor to the polypeptide of the present invention expressed on a cell membrane by culturing the transformant bearing the DNA encoding the receptor to the polypeptide of the present invention;

(4) a method of screening the compounds that alter the binding property between the polypeptide of the present invention and a receptor to the polypeptide of the present invention (the compounds that promote or inhibit the activities of the polypeptide of the present invention), or salts thereof, which comprises measuring and comparing a cell stimulating activity mediated by the receptor to the polypeptide of the present invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, NO production, production of physiologically active substances inherently produced by the cells, etc.), when a compound that activates the receptor to the polypeptide of the present invention (e.g., the polypeptide of the present invention) is brought in contact with a cell containing the receptor to the polypeptide of the present invention, and when a compound that activates the receptor to the polypeptide of the present invention and a test compound are brought in contact with a cell containing the receptor to the polypeptide of the present invention; and, (5) a method of screening the compounds that alter the binding property between the polypeptide of the present invention and a receptor to the polypeptide of the present invention (the compounds that promote or inhibit the activities of the polypeptide of the present invention), or salts thereof, which comprises measuring and comparing a cell stimulating activity mediated by the receptor to the polypeptide of the present invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, NO production, production of physiologically active substances inherently produced by the cells, etc.), when a compound that activates the receptor to the polypeptide of the present invention (e.g., the polypeptide of the present invention, etc.) is brought in contact with the receptor to the polypeptide of the present invention expressed on a cell membrane by culturing the transformant containing the DNA encoding the receptor to the polypeptide of the present invention, and when a compound that activates the receptor to the polypeptide of the present invention and a test compound are brought in contact with the receptor to the polypeptide of the present invention expressed on a cell membrane by culturing the transformant containing the DNA encoding the receptor to the polypeptide of the present invention; etc.

(6) The DNA encoding the receptor to the polypeptide of the present invention can be acquired by the following procedures. The polypeptide of the present invention is labeled with a radioisotope such as $^{125}I$, etc., a fluorescent substance such as fluorescein, etc. or biotin, etc. to find the cell line, tissues, organs, etc. capable of specifically binding the labeled polypeptide thereto. Then, mRNAs are extracted therefrom by publicly known methods and cDNAs are synthesized, followed by cloning to expression vectors for animal cells. The clones are transfected to COS7 cells, etc., and transformants inserted with the DNA encoding the receptor to the polypeptide of the present invention can be selected (expression cloning).

(7) Also, the novel receptor cDNA fragment belonging to the insulin receptor family can be acquired by preparing a primer mixture for the structural characteristic common to the insulin receptor family (e.g., amino acid sequences such as tyrosine kinase, etc.) and conducting RT-PCR. Subsequently, 5'-RACE and 3'-RACE PCR are carried out based on the DNA sequence obtained to acquire the full-length cDNA. This CDNA is inserted into the expression vector for animal cells to express in appropriate animal culture cells such as CHO cells, COS7 cells, etc. By confirming that the polypeptide of the present invention specifically binds, it can be confirmed that the DNA encodes the receptor to the polypeptide of the present invention.

The screening methods of the present invention are specifically explained below.

First, the tissues, cells or membrane fractions thereof, etc. used for the screening methods of the present invention, to which the polypeptide of the present invention is bound, namely, the receptor to the polypeptide of the present invention may be any of them, so long as the polypeptide of the present invention can specifically bind thereto. Preferred are the organs of human or other warm-blooded animals, culture cells, or membrane fractions thereof. Since human-derived organs are obtained only with extreme difficulty, human recombinant receptors, etc. expressed in large quantities by use of recombinants are suitable.

To produce the receptor to the polypeptide of the present invention, the aforesaid methods for producing the polypeptide of the present invention, etc. are applied.

When cells containing the receptor to the polypeptide of the present invention or membrane fractions of these cells are employed in the screening methods of the present invention, they may be prepared following the procedures later described.

Where cells containing the receptor to the polypeptide of the present invention are employed, the cells may be fixed using glutaraldehyde, formalin, etc. The fixation can be made by publicly known methods.

The cells containing the receptor to the polypeptide of the present invention refer to the cell line wherein the receptor to the polypeptide of the present invention is expressed, and such may be transformants, which host cells are *Escherichia coli, Bacillus subtilis*, yeast, insect cells, animal cells, etc. The host cells that have expressed the receptor to the polypeptide of the present invention may be acquired in a similar manner to the aforesaid method of producing transformants transformed by the expression vector containing the polypeptide of the present invention.

The cell membrane fraction is a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor to the polypeptide of the present invention expressed and membrane components such as cell-derived phospholipids and membrane proteins.

The amount of the receptor to the polypeptide of the present invention in the cells containing the receptor to the polypeptide of the present invention or in the membrane fraction is preferably $10^3$ to $10^8$ molecules per cell, more preferably $10^5$ to $10^7$ molecules per cell. As the amount of expression increases, the ligand binding activity per unit of the membrane fraction (specific activity) increases so that not only the highly sensitive screening system can be constructed but also large quantities of samples can be assayed with the same lot.

To perform the methods (1) through (3) for screening the compound that alters the binding property between the polypeptide of the present invention and the receptor to the polypeptide of the present invention (the compound that promotes or inhibits the activity of the polypeptide of the present invention), an appropriate receptor fraction to the polypeptide of the present invention and a labeled form of the polypeptide of the present invention are employed. For the receptor fraction to the polypeptide of the present invention, the receptor fractions of naturally occurring tissues or cells to the polypeptide of the present invention or recombinant receptor fractions having an activity equivalent thereto, or the like are desirable. Herein, the equivalent activity refers to an equivalent ligand binding activity, etc. As the labeled ligands, there may be used the labeled form of the polypeptide of the present invention, etc. The polypeptide of the present invention labeled with [$^{3}H$], [$^{125}I$], [$^{14}C$], [$^{35}S$], a fluorescent dye, biotin, an enzyme such as β galactosidase, peroxidase, etc. may be employed.

Specifically, the screening of the compound that alters the binding property between the polypeptide of the present invention and the receptor to the polypeptide of the present invention can be performed by the following procedures. First, a receptor preparation is prepared by suspending cells containing the receptor to the polypeptide of the present invention or their membrane fractions in a buffer appropriate for screening. Any buffer can be used so long as it does not interfere with ligand-receptor binding, such buffers including a phosphate buffer or a Tris-HCl buffer having pH of 4 to 10 (preferably pH of 6 to 8), etc. For the purpose of minimizing non-specific binding, a surfactant such as CHAPS, Tween-80™ (manufactured by Kao-Atlas Inc.), digitonin or deoxycholate may be added to the buffer. Further for the purpose of suppressing the degradation of the receptor or the polypeptide of the present invention by a protease, a protease inhibitor such as PMSF, leupeptin, E-64 (manufactured by Peptide Institute, Inc.) and pepstatin may also be added. A given amount (5,000 cpm to 500,000 cpm) of a labeled form of the polypeptide of the present invention is added to 0.01 ml to 10 ml of the receptor solution, and at the same time, $10^{-10}$ to $10^{-6}$M of a test compound is co-present. To determine the amount of non-specific binding (NSB), a reaction tube containing a large excess of the polypeptide of the present invention in an unlabeled form is also provided. The reaction is carried out at 0° C. to 50° C., preferably about 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$-NSB) is made 100%, a test compound having the specific binding (B-NSB) of, e.g., 50% or less can be selected as a candidate material capable of competitive inhibition.

To perform the method (4) or (5) given above for screening the compound that alters the binding property between the polypeptide of the present invention and the receptor to the polypeptide of the present invention (the compound that promotes or inhibits the activity of the polypeptide of the present invention), the cell-stimulating activities mediated by the receptor to the polypeptide of the present invention (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, NO production, production of physiologically active substances inherently produced by the cells, etc.) may be determined by a publicly known method, or using an assay kit commercially available. Specifically, the cells containing the receptor to the polypeptide of the present invention are first cultured on a multi-well plate, etc. Prior to the screening, the medium is replaced with a fresh medium or with an appropriate non-cytotoxic buffer, followed by culturing for a given period of time in the presence of a test compound, etc. Subsequently, the cells are extracted or the supernatant is recovered and the resulting product is quantified by appropriate procedures. Where it is difficult to detect the production of the indicator substance for the cell-stimulating activity (e.g., arachidonic acid, etc.) due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production can be detected. As to the pH reduction in extracellular fluids, a change in the acidification rate can be measured using a microphysiometer (Cytosensor™, etc.).

To perform the screening by assaying the cell stimulating activity, cells in which an appropriate receptor to the polypeptide of the present invention is expressed are required. As the cells wherein the receptor to the polypeptide of the present invention is expressed, naturally occurring cell lines, cell lines wherein the receptor to the polypeptide of the present invention described above is expressed, etc. are desirable.

Examples of the test compound include peptides, proteins, non-peptide compounds, synthetic compounds, fermentation products, cell extracts, plant extracts, animal tissue extracts, and the like.

The kit for screening the compound that alters the binding property between the polypeptide of the present invention and the receptor to the polypeptide of the present invention (the compound that promotes or inhibits the activity of the polypeptide of the present invention) or salts thereof, comprises, the polypeptide of the present invention, and the object to which the polypeptide of the present invention binds (the receptor to the polypeptide of the present invention, cells containing the receptor to the polypeptide of the present invention, membrane fractions of the cells containing the receptor to the polypeptide of the present invention, etc.).

The compounds or salts thereof, which are obtainable using the screening methods or screening kits of the present invention, are compounds that alter the binding (inhibit or promote the binding) between the polypeptide of the present invention and the receptor to the polypeptide of the present invention (the compound that promotes or inhibits the activity of the polypeptide of the present invention), and specifically, compounds having the cell stimulating activities via the receptor to the polypeptide of the present invention, or salts thereof (so-called agonists of the receptor to the polypeptide of the present invention), or compounds having no such stimulating activities (so-called antagonists of the receptor to the polypeptide of the present invention). Examples of these compounds include peptides, proteins, non-peptide compounds, synthetic compounds, fermentation products, and the like. These compounds may be publicly known compounds.

To specifically determine if the compound is the agonist or antagonist of the receptor to the polypeptide of the present invention, the following method (i) or (ii) may be used.

(i) After the compound that alters the binding property between the polypeptide of the present invention and the receptor to the polypeptide of the present invention (especially inhibits the binding) is obtained, it is determined if the compound has the aforesaid cell-stimulating activity mediated by the receptor to the polypeptide of the present invention. The compound having the cell-stimulating activity or its salt is an agonist of the receptor to the polypeptide of the present invention, whereas the compound or its salt having no such activity is an antagonist of the receptor to the polypeptide of the present invention.

(ii) (a) A test compound is brought in contact with cells containing the receptor to the polypeptide of the present invention to assay the aforesaid cell-stimulating activity mediated by the receptor to the polypeptide of the present invention. The compound or its salt having the cell-stimulating activity is an agonist of the receptor to the polypeptide of the present invention.

(b) The cell-stimulating activity mediated by the receptor to the polypeptide of the present invention is measured, both when the compound that activates the receptor to the polypeptide of the present invention (e.g., the polypeptide of the present invention, or an agonist of the receptor to the polypeptide of the present invention, etc.) is brought in contact with cells containing the receptor to the polypeptide of the present invention and when the compound that activates the receptor to the polypeptide of the present invention and a test compound are brought in contact with cells containing the receptor to the polypeptide of the present invention, and comparison is made on the cell-stimulating activity between the two cases. The compound capable of reducing the cell-stimulating activity by the compound or its salt that activate the receptor to the polypeptide of the present invention is an antagonist of the receptor to the polypeptide of the present invention.

The agonists of the receptor to the polypeptide of the present invention exhibit similar activities to the physiological activities possessed by the polypeptide of the present invention on the receptor to the polypeptide of the present invention, and are thus useful as safe and low toxic drugs, likewise the polypeptide of the present invention.

Conversely, since the antagonists of the receptor to the polypeptide of the present invention can suppress the physiological activities that the polypeptide of the present invention possesses on the receptor to the polypeptide of the present invention, they are useful as safe and low toxic drugs that suppress the activities caused when the polypeptide of the present invention is excessive.

Examples of the compounds or salts thereof, which are obtainable using the screening methods or screening kits of the present invention, are compounds selected from, e.g., peptides, proteins, non-peptide compounds, synthetic compounds, fermentation products, cell extracts, plant extracts, animal tissue extracts, plasma, and the like, and are the compounds that promote or inhibit the functions of the polypeptide of the present invention.

For salts of these compounds, the same salts as those given for the polypeptide of the present invention above may be used.

When the compounds obtainable using the screening methods or screening kits of the present invention are used as the therapeutic/prophylactic agents described above, a conventional manner may apply thereto. The compounds may be prepared in the form of tablets, capsules, elixirs, microcapsules, sterile solutions, suspensions, etc.

Since the thus obtained pharmaceutical preparation is safe and low toxic, the preparation can be administered to, for example, warm-blooded animal (e.g., human, mouse, rat, rabbit, sheep, swine, bovine, horse, chicken, cat, dog, monkey, etc.).

The dose of the compound or its salt may vary depending on its action, target disease, subject to be administered, route for administration, etc. When the compound that promotes the function of the polypeptide of the present invention is orally administered for the purpose of treating various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., the compound is administered to adult (as 60 kg body weight) generally in a daily dose of approximately 0.01 to 1000 mg, preferably approximately 0.1 to 1000 mg, more preferably approximately 1.0 to 200 mg, and most preferably approximately 1.0 to 50 mg. When it is parenterally administered, a single dose of the compound may vary depending on subject to be administered, target disease, etc. When the compound that promotes the function of the polypeptide of the present invention is administered to adult (as 60 kg) in the form of injection for the purpose of treating various diseases, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., it is desired to administer the polypeptide either by local injection to the affected area or systemic injection, generally in a daily dose of approximately 0.01 to 30 mg, preferably approximately 0.1 to 20 mg, and more preferably approximately 0.1 to 10 mg. For other animal species, the corresponding dose as converted per 60 kg weight can be administered.

On the other hand, when the compound that inhibits the function of the polypeptide of the present invention is orally administered, the compound is administered to adult (as 60 kg body weight) generally in a daily dose of approximately 0.01 to 1000 mg, preferably approximately 0.1 to 1000 mg, more preferably approximately 1.0 to 200 mg, and most preferably approximately 1.0 to 50 mg. In the case of parenteral administration, a single dose of the compound may vary depending on subject to be administered, target disease, etc. When the compound that inhibits the function of the polypeptide of the present invention is administered to adult (as 60 kg) in the form of injection, it is advantageous to intravenously administer the compound in a daily dose of approximately 0.01 to 30 mg, preferably approximately 0.1 to 20 mg, and more preferably approximately 0.1 to 10 mg. For other animal species, the corresponding dose as converted per 60 kg can be administered.

(3) Quantification for the Polypeptide or its Salt of the Present Invention:

The antibody to the polypeptide of the present invention (hereinafter sometimes merely referred to as the antibody of the present invention) is capable of specifically recognizing the polypeptide of the present invention and thus, can be used for quantification of the polypeptide of the present invention in a test sample fluid, in particular, for quantification by the sandwich immunoassay.

That is, the present invention provides:

(i) a method for quantification of the polypeptide of the present invention in a test sample fluid, which comprises competitively reacting the antibody of the present invention, a test sample fluid and a labeled form of the polypeptide of the present invention, and measuring the ratio of the labeled polypeptide of the present invention bound to said antibody; and, (ii) a method for quantification of the polypeptide of the present invention in a test sample fluid, which comprises reacting the test sample fluid simultaneously or continuously with the antibody of the present invention immobilized on a carrier and a labeled form of the antibody of the present invention, and then measuring the activity of the labeling agent on the insoluble carrier.

The monoclonal antibody to the polypeptide of the present invention (hereinafter sometimes merely referred to as the monoclonal antibody of the present invention) may be used to quantify the polypeptide of the present invention. Besides, the polypeptide of the present invention may also be detected by means of a tissue staining. For these purposes, the antibody molecule per se may be used or $F(ab')_2$, Fab' or Fab fractions of the antibody molecule may be used as well.

There is no particular limitation to the method of quantifying the polypeptide of the present invention using the antibody of the present invention; any method may be used, so far as it relates to a method in which the amount of antibody, antigen or antibody-antigen complex can be detected by a chemical or a physical means, depending on or corresponding to the amount of antigen (e.g., the amount of the polypeptide of the present invention) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be later described, is particularly preferred.

Examples of the labeling agent used in the assay method using the labeling substance are radioisotopes, enzymes, fluorescent substances, luminescent substances, etc. Examples of the radioisotope are [$^{125}$I], [$^{121}$I], [$^{3}$H], [$^{14}$C], etc. Preferred examples of the enzyme are those that are stable and have a high specific activity, which include β-galactosidase, β-glucosidase, alkaline phosphatase, peroxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding conventionally used for immobilization of proteins or enzymes may be used as well. Examples of the carrier include insoluble polysaccharides such as agarose, dextran and cellulose; synthetic resins such as polystyrene, polyacrylamide, silicone, etc.; glass; and the like.

In the sandwich method, a test sample fluid is reacted with an immobilized form of the monoclonal antibody of the present invention (primary reaction), then reacted with another labeled form of the monoclonal antibody of the present invention (secondary reaction) and the activity of the labeling agent on the insoluble carrier is assayed, whereby the amount of the polypeptide of the present invention in the test sample fluid can be quantified. The primary and secondary reactions may be carried out in a reversed order, simultaneously or sequentially with an interval. The type of the labeling agent and the method for immobilization may be effected by modifications of those described hereinabove. In the immunoassay by the sandwich method, it is not always necessary that the antibody used for the labeled antibody and for the solid phase should be one type or one species but a mixture of two or more antibodies may be used as well, for the purpose of improving the measurement sensitivity, etc.

In the method for assaying the polypeptide of the present invention by the sandwich method according to the present invention, preferred monoclonal antibodies of the present invention used for the primary and the secondary reactions are antibodies, which binding sites to the polypeptide of the present invention are different from one another. Thus, the antibodies used in the primary and the secondary reactions are those wherein, when the antibody used in the secondary reaction recognizes the C-terminal region of the polypeptide of the present invention, the antibody recognizing the site other than the C-terminal regions, e.g., recognizing the N-terminal region, is preferably used in the primary reaction.

The monoclonal antibody of the present invention may be used in an assay system other than the sandwich method, such as a competitive method, an immunometric method, nephrometry, etc.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody described above is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the quantification method of the present invention, any special conditions or operations are not required to set forth. The assay system for the polypeptide of the present invention may be constructed in addition to conditions or operations conventionally used for each of the methods, taking the technical consideration by one skilled in the art into account. For the details of such conventional technical means, a variety of reviews, reference books, etc. may be referred to (for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.):

"Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, the polypeptide of the present invention can be quantified with high sensitivity, using the antibody of the present invention.

Furthermore, when an increase or decrease in the concentration of the polypeptide of the present invention is detected by quantifying the concentration of the polypeptide of the present invention using the antibody of the present invention, it can be diagnosed that the following diseases are involved or it is highly likely to suffer from these disease in the future; for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc.

The antibody of the present invention can be employed for detecting the polypeptide of the present invention which may be present in a test sample fluid such as a body fluid, a tissue, etc. The antibody can also be used to prepare an antibody column for purification of the polypeptide of the present invention, detection of the polypeptide of the present invention in the fractions when purified, and analysis of the behavior of the polypeptide of the present invention in the cells under investigation, etc.

(4) Gene Diagnostic Agent

By using the DNA of the present invention, e.g., as a probe, an abnormality (gene abnormality) of the DNA or mRNA encoding the polypeptide of the present invention in warm-blooded animal (e.g., human, rat, mouse, guinea pig, rabbit, chicken, sheep, swine, bovine, horse, cat, dog, monkey, etc.)can be detected. Therefore, the DNA of the present invention is useful as a gene diagnostic agent for the damage to the DNA or mRNA, its mutation, or its decreased expression, or increased expression or overexpression of the DNA or mRNA. By performing chromosomal mapping, the DNA of the present invention may also be used for studies of hereditary diseases.

The gene diagnosis described above using the DNA of the present invention can be performed by, for example, the publicly known Northern hybridization assay, the PCR-SSCP assay (Genomics, 5, 874–879 (1989); Proceedings of the National Academy of Sciences of the United States of America, 86, 2766–2770 (1989)) or the DNA microarray (Science, 270, 467–470 (1995)), etc.

For example, when reduced expression is detected by northern hybridization, DNA microarray, etc. or when mutation of DNA is detected by PCR-SS or DNA microarray, it can be diagnosed that the following diseases are involved or it is highly likely to suffer in the future from these disease; for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc.

(5) Pharmaceutical Composition Comprising Antisense DNA

Antisense DNA that binds to the DNA of the present invention complementarily to inhibit expression of the DNA can suppress the function of the polypeptide of the present invention or the DNA of the present invention in the body, and thus used as the agent for the treatment/prevention of diseases caused by, e.g., overexpression of the polypeptide of the present invention.

The antisense DNA described above can be employed as the above therapeutic/prophylactic agent similarly to the therapeutic/prophylactic agent for various disease comprising the DNA of the present invention described above.

For example, the antisense DNA alone is administered directly, or the antisense DNA is inserted into an appropriate vector such as retrovirus vector, adenovirus vector, adenovirus-associated virus vector, etc., which is then administered in a conventional manner. The antisense DNA may be administered as it stands, or prepared into pharmaceutical preparations together with physiologically acceptable carriers such as adjuvants to assist its uptake, and such preparations are administered by gene gun or through a catheter like a hydrogel catheter. Alternatively, the antisense DNA may be prepared in the form of aerosol and intratracheally administered as an inhalant.

The dose of the antisense DNA may vary depending upon target disease, subject to be administered, route for administration, etc. When the antisense DNA of the present invention is topically administered intratracheally, e.g., as an inhalant, the antisense DNA is administered to adult (60 kg body weight) generally in a daily dose of approximately 0.1 to 100 mg.

In addition, the antisense DNA may also be employed as an oligonucleotide probe for diagnosis to examine the presence of the DNA of the present invention in tissues or cells, or the states of its expression.

(6) Pharmaceuticals Comprising the Antibody of the Present Invention

The antibody of the present invention which possesses the effect of neutralizing the activities of the polypeptide of the present invention can be used as drugs for the treatment/prevention of diseases caused by overexpression of the polypeptide of the present invention.

The therapeutic/prophylactic agent containing the antibody of the present invention described above may be administered orally or parenterally to mammal (e.g., human, rat, rabbit, sheep, swine, bovine, cat, dog, monkey, etc.) as a liquid preparation in its original form, or as a pharmaceutical composition in an appropriate drug form. The dose varies depending on subject to be administered, target disease, symptom, route for administration, etc.; for example, it is advantageous to intravenously administer the antibody of the present invention to adult normally in a single dose of approximately 0.01 to 20 mg/kg body weight, preferably approximately 0.1 to 10 mg/kg body weight, and more preferably approximately 0.1 to 5 mg/kg per day approximately 1 to 5 times a day, preferably approximately 1 to 3 times. In parenteral administration in other route and in oral administration, a dose similar to those given above can be administered. Where conditions are serious, the dose may be increased depending on the conditions.

The antibody of the present invention may be administered in itself or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. may be used in combination. For the oily solution, for example, vegetable oil such as olive oil, sesame oil, soybean oil, peanut oil, cotton seed oil, corn oil, etc., vegetable oil such as olive oil, sesame oil, soybean oil, peanut oil, cotton seed oil, corn oil, etc., are used, and dissolution aids such as benzyl benzoate, benzyl alcohol, etc. may be used in combination. The thus prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of approximately 5 to 500 mg per unit dosage form, approximately 5 to 100 mg especially for injections and approximately 10 to 250 mg for other preparations.

Each composition described above may further contain other active components unless formulation with the antibody causes any adverse interaction.

(7) DNA Transgenic Animal

The present invention provides a non-human mammal bearing the DNA encoding the polypeptide of the present invention, which is exogenous (hereinafter is simply referred to as the exogenous DNA of the present invention) or its mutant DNA (sometimes simply referred to as the exogenous mutant DNA of the present invention).

Thus, the present invention provides: (1) a non-human mammal bearing the exogenous DNA or its mutant DNA; (2) the mammal according to (1), wherein the non-human mammal is a rodent; (3) the mammal according to (1), wherein the rodent is mouse or rat; and, (4) a recombinant vector bearing the exogenous DNA of the present invention or its mutant DNA and capable of expressing in a mammal.

The non-human mammal bearing the exogenous DNA of the present invention or its mutant DNA (hereinafter simply referred to as the DNA transgenic animal of the present invention) can be created by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell or the like, by the DNA transfection methods, and utilize the transformant for cell culture, tissue 3s culture, etc. In addition, these cells may be fused with the above-described germinal cell by a publicly known cell fusion method to create the transgenic animal of the present invention.

Examples of the non-human mammal that can be used include monkeys, bovine, swine, sheep, goat, rabbits, dogs, cats, guinea pigs, hamsters, mice, rats and the like. Above all, preferred are rodents, especially mice (e.g., C57BL/6 strain, DBA2 strain, etc. for a pure line and for a cross line, $B6C3F_1$ strain, $BDF_1$ strain $B6D2F_1$ strain, BALB/c strain, ICR strain, etc.) or rats (Wistar, SD, etc.) and the like, since they are relatively short in ontogeny and life cycle from a standpoint of creating model disease animals, and are easy in breeding.

"Mammals" in a recombinant vector that can be expressed in mammals include, in addition to the aforesaid non-human mammals, human, etc.

The exogenous DNA of the present invention refers to the DNA of the present invention that is once isolated and extracted from mammals, not the DNA of the present invention inherently possessed by the non-human mammals. The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA. The abnormal DNA is intended to mean the DNA that expresses the abnormal polypeptide of the present invention and exemplified by such a DNA that expresses a polypeptide capable of suppressing the functions of the normal polypeptide of the present invention, or the like.

The exogenous DNA of the present invention may be any one of those derived from a mammal of the same species as, or a different species from, the mammal as the target animal. In transfecting the DNA of the present invention to the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target mammal, e.g., a fertilized egg of mouse, downstream the various promoters capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, etc., retroviruses such as Moloney leukemia virus, etc., animal viruses such as vaccinia virus, baculovirus, etc. Of these vectors, *Escherichia coli*-derived plasmids, *Bacillus subtilis*-derived plasmids, yeast-derived plasmids, etc. are preferably used.

Examples of these promoters for regulating the DNA expression include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human polypeptide elongation factor 1α (EF-1α) promoters, human and chicken β actin promoters etc., which can achieve high expression in the whole body, are preferred.

It is preferred that the vectors described above have a sequence for terminating the transcription of the desired messenger RNA in the DNA transgenic animal (generally called a terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region can be prepared, as a DNA construct capable of being expressed in the transgenic animal, by a conventional DNA engineering technique, in which the DNA is ligated downstream the aforesaid promoter and if desired, upstream the translation termination site.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal, in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells of the target mammal. The fact that the exogenous DNA of the present invention is excessively present in the germinal cells of the prepared animal after transfection means that all of the offspring of the animal prepared have the exogenous DNA of the present invention excessively in all of the germinal cells and somatic cells thereof. The offspring of the animal of this kind that inherits the exogenous DNA of the present invention excessively have the DNA of the present invention in all of the germinal cells and somatic cells thereof.

By obtaining a homozygotic animal having the transfected DNA in both of homologous chromosomes and mating a male and female of the animal, all offspring can be passaged to excessively retain the DNA.

In a non-human mammal bearing the normal DNA of the present invention, the normal DNA of the present invention is expressed to a high level, and may eventually develop the hyperfunction of the polypeptide of the present invention by promoting the functions of endogenous normal DNA. Therefore, the animal can be utilized as a pathologic model animal for such a disease. Specifically, using the normal DNA transgenic animal of the present invention, it becomes possible to elucidate the hyperfunction of the polypeptide of the present invention and to clarify the pathological mechanism of the disease associated with the polypeptide of the present invention and to determine how to treat these diseases.

Furthermore, since a mammal transfected the exogenous normal DNA of the present invention exhibits an increasing symptom of the librated polypeptide of the present invention, the animal is usable for screening of therapeutic agents agent for the disease associated with the polypeptide of the present invention.

On the other hand, non-human mammal having the exogenous abnormal DNA of the present invention can be passaged under normal breeding conditions as the DNA-bearing animal by confirming the stable retaining of the exogenous DNA via crossing. In addition, the objective exogenous DNA can be utilized as a starting material by inserting the objective exogenous DNA into the plasmid described above. The DNA construct with a promoter can be prepared using conventional DNA engineering techniques. The transfection of the abnormal DNA of the present invention at the fertilized egg cell stage is preserved to be present in all of the germinal and somatic cells of the mammals to be targeted. The fact that the abnormal DNA of the present invention is present in the germinal cells of the animal after DNA transfection means that all of the offspring of the prepared animal have the abnormal DNA of the present invention in all of the germinal and somatic cells. The offspring of such an animal that inherits the exogenous DNA of the present invention has the abnormal DNA of the present invention in all the germinal and somatic cells. A homozygous animal having the introduced DNA on both of homologous chromosomes can be acquired and then by mating these male and female animals, all the offspring can be bred to have the DNA.

Since the non-human mammal having the abnormal DNA of the present invention expresses the abnormal DNA of the present invention at a high level, the animal may cause the function inactive type inadaptability of the polypeptide of the present invention by inhibiting the functions of the endogenous normal DNA, and can be utilized as its disease model animal. For example, using the abnormal DNA-transferred animal of the present invention, it is possible to elucidate the mechanism of the function inactive type inadaptability of the polypeptide of the present invention and to study a method for treatment of this disease.

In its specific applicability, the transgenic animal of the present invention expressing the abnormal DNA of the present invention to a high level is also expected to serve as an experimental model for the elucidation of the mechanism of the functional inhibition (dominant negative effect) of a normal polypeptide by the abnormal polypeptide of the present invention in the function inactive type inadaptability of the polypeptide of the present invention.

A mammal bearing the abnormal exogenous DNA of the present invention is also expected to serve for screening a candidate drug for the treatment of the function inactive type inadaptability of the polypeptide of the present invention, since the polypeptide of the present invention is increased in such an animal in its free form.

Other potential applicability of the two kinds of the transgenic animals described above include:

(1) use as a cell source for tissue culture;

(2) elucidation of the association with a polypeptide that is specifically expressed or activated by the polypeptide of the present invention, through direct analysis of DNA or RNA in tissue of the DNA transgenic animal of the present invention or by analysis of the polypeptide tissue expressed by the DNA;

(3) research in the function of cells derived from tissues that are cultured usually only with difficulty, using cells of tissue bearing the DNA cultured by a standard tissue culture technique;

(4) screening for a drug that enhances the functions of cells using the cells described in (3) above; and, (5) isolation and purification of the variant polypeptide of the present invention and preparation of an antibody thereto.

Furthermore, clinical conditions of a disease associated wit the polypeptide of the present invention, including the function inactive type inadaptability of the polypeptide of the present invention can be determined using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the polypeptide of the present invention, and as studies on association with apoptosis, differentiation or propagation or on the mechanism of signal transduction in these properties to inspect any abnormality therein. Thus, the DNA transgenic animal of the present invention can provide an effective research material for the polypeptide of the present invention and for elucidating the function and effect thereof.

To develop pharmaceuticals for the treatment of diseases associated with the polypeptide of the present invention, including the function inactive type inadaptability of the polypeptide of the present invention, using the DNA transgenic animal of the present invention, an effective and rapid method for screening the pharmaceuticals for the treatment of diseases can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human mammal embryonic stem cell in which the DNA of the present invention is inactivated;

(2) the embryonic stem cell according to (1), wherein the DNA is inactivated by introducing a reporter gene (e.g., β-galactosidase gene derived from *Escherichia coli*);

(3) the embryonic stem cell according to (1), which is resistant to neomycin;

(4) the embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA of the present invention is inactivated;

(7) the non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;

(8) the non-human mammal according to (6), which is a rodent;

(9) the non-human mammal according to (8), wherein the rodent is mouse; and,

(10) a method for screening a compound or its salt that promotes or inhibits the promoter activity for the DNA of the present invention, which comprises administering a test compound to the mammal of (7) and detecting expression of the reporter gene.

The non-human mammalian embryonic stem cell, in which the DNA of the present invention is inactivated, refers to a non-human mammalian embryonic stem cell that suppresses the ability of the non-human mammalian to express the DNA by artificially mutating the DNA of the present invention possessed in the non-human mammal, or the DNA has no substantial ability to express the polypeptide of the present invention (hereinafter sometimes referred to as the knockout DNA of the present invention) by substantially inactivating the activities of the polypeptide of the present invention encoded by the DNA (hereinafter merely referred to as ES cell).

As the non-human mammalian, the same examples as described above apply.

Techniques for artificially mutating the DNA of the present invention include deletion of a part or all of the DNA sequence and insertion of or substitution with other DNA, e.g., by genetic engineering. By these variations, the knockout DNA of the present invention may be prepared, for example, by shifting the reading frame of a codon or by disrupting the function of a promoter or exon.

Specifically, the non-human mammalian embryonic stem cell, in which the DNA of the present invention is inactivated (hereinafter merely referred to as the ES cell with the DNA of the present invention inactivated or the knockout ES cell of the present invention), can be obtained by, for example, isolating the DNA of the present invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby to destroy the functions of exon, or by inserting into the intron site between exons a DNA sequence which terminates gene transcription (e.g., polyA-added signal, etc.) thereby to disable the synthesis of complete messenger RNA, into a chromosome of the animal cells by, e.g., homologous recombination. The thus-obtained ES cells are analyzed by the Southern hybridization using as a probe a DNA sequence on or near the DNA of the present invention, or by PCR using as primers a DNA sequence on the targeting vector and another DNA sequence near the DNA of the present invention which is not included in the targeting vector, and the knockout ES cell of the present invention is selected.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the BDF, mouse ($F_1$ hybrid between C57BL/6 and DBA/2), wherein the low ovum collection per C57BL/6 mouse or C57BL/6 has been improved by crossing with DBA/2, may be preferably used, instead of obtaining a pure line of ES cells with the clear immunological genetic background. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently, by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1–10000 U/nl) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in monolayers or to form cell aggregates in suspension under appropriate conditions, it is possible to differentiate them to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the functions of the polypeptide of the present invention in vitro cytologically or molecular biologically.

The non-human mammal deficient in expression of the DNA of the present invention can be identified from a normal animal by measuring the amount of mRNA in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes thereof, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The cells with the DNA of the present invention in which the DNA of the present invention is rendered knockout can be identified by the Southern hybridization analysis using as a probe a DNA sequence on or near the DNA of the present invention, or by PCR analysis using as primers a DNA sequence on the targeting vector and another DNA sequence which is not included in the DNA of the present invention derived from mouse, which is used as the targeting vector. When non-human mammalian embryonic stem cells are used, the cell line wherein the DNA of the present invention is inactivated is cloned by homologous recombination; the resulting cloned cell line is injected to, e.g., a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, in which all tissues are composed of cells having an artificially mutated locus of the DNA of the present invention, can be selected from a series of offspring obtained by crossing between such a chimeric animal and a normal animal, e.g., by coat color identification, etc. The individuals thus obtained are normally deficient in heterozygous expression of the polypeptide of the present invention. The individuals deficient in homozygous expression of the polypeptide of the present invention can be obtained from offspring of the intercross between the heterozygotes.

When an oocyte is used, a DNA solution may be injected, e.g., to the prenucleus by microinjection thereby to obtain a transgenic non-human mammal having a targeting vector introduced into its chromosome. From such transgenic non-human mammals, those having a mutation at the locus of the DNA of the present invention can be obtained by selection based on homologous recombination.

As described above, individuals wherein the DNA of the present invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention fails to express, lacks various biological activities induced by the polypeptide of the present invention, such an animal can be a disease model suspected of inactivated biological activities of the polypeptide of the present invention and thus, offers an effective study to investigate causes for and therapy for these diseases.

(8a) Method for Screening of Compounds Having Therapeutic/Prophylactic Effects for Diseases Caused by Deficiency, Damages, etc. of the DNA of the Present Invention The non-human mammal deficient in expression of the DNA of the present invention can be used to screen the compounds having therapeutic/prophylactic effects for diseases caused by deficiency, damages, etc. of the DNA of the present invention (abnormalities (e.g., diabetes mellitus, obesity, etc.) in metabolic regulation (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc.).

That is, the present invention provides a method for screening of a compound or its salt having therapeutic/prophylactic effects for diseases caused by deficiency, damages, etc. of the DNA of the present invention, which comprises administering a test compound to the non-human mammal deficient in expression of the DNA of the present invention, and observing and measuring a change occurred in the animal.

As the non-human mammal deficient in expression of the DNA of the present invention used for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. and these compounds may be novel compounds or publicly known compounds.

Specifically, the non-human mammal deficient in the expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, the amount of a test compound administered can be appropriately selected depending on administration route, nature of the test compound, or the like.

For example, in the case of screening a compound having a therapeutic/prophylactic effect for diseases such as pancreas function disorders, the non-human mammal deficient in expression of the DNA of the present invention is subjected to a sugar loading treatment, a test compound is administered before or after the sugar loading treatment and, blood sugar level, body weight change, etc. of the animal is measured with passage of time.

The compound obtained using the above screening methods is a compound selected from the test compounds described above and exhibits a therapeutic/prophylactic effect for the diseases caused by deficiencies, damages, etc. of the polypeptide of the present invention (abnormalities (e.g., diabetes mellitus, obesity, etc.) in metabolic regulation (e.g., diabetes mellitus, obesity, etc.) in metabolic regulation (sugar metabolism, lipid metabolism, etc.) of energy sources such as carbohydrates; inhibition of growth/proliferation/ differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc.). Therefore, the compound can be used as a safe and low toxic drug for the treatment/prevention, etc. for these diseases. Furthermore, compounds derived from such a compound obtained by the screening supra can be used as well.

The compound obtained by the screening above may be in the form of salts. As the salts of the compound, there may be used salts with physiologically acceptable acids (e.g., inorganic acids or organic acids) or bases (e.g., alkali metal salts), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical containing the compound or salts thereof obtained by the above screening methods may be manufactured in a manner similar to the method for preparing the composition containing the polypeptide of the present invention described hereinabove.

Since the pharmaceutical composition thus obtained is safe and low toxic, it can be administered to mammal (e.g., human, rat, mouse, guinea pig, rabbit, sheep, swine, bovine, horse, cat, dog, monkey, etc.).

The dose of the compound or its salt may vary depending on target disease, subject to be administered, route for administration, etc. When the compound is orally administered for the purpose of treating, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., the compound is administered to adult (as 60 kg body weight) generally in a daily dose of approximately 0.01 to 1000 mg, preferably approximately 0.1 to 1000 mg, more preferably approximately 1.0 to 200 mg, and most preferably approximately 1.0 to 50 mg. In parenteral administration, a single dose of the compound may vary depending on subject to be administered, target disease, etc. When the compound is administered to adult (as 60 kg) in the form of injection for the purpose of treating, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., it is desired to intravenously administer the compound in the form of injection, generally in a daily dose of approximately 0.01 to 30 mg, preferably approximately 0.1 to 20 mg, and more preferably approximately 0.1 to 10 mg. For other animal species, the corresponding dose as converted per 60 kg weight can be administered.

(8b) Method of Screening a Compound that Promotes or Inhibits the Activities of a Promoter to the DNA of the Present Invention The present invention provides a method of screening a compound or its salt that promotes or inhibits the activities of a promoter to the DNA of the present invention, which comprises administering a test compound to a non-human mammal deficient in expression of the DNA of the present invention and detecting expression of the reporter gene. In the screening method described above, the non-human mammal deficient in expression of the DNA of the present invention is selected from the aforesaid non-human mammal deficient in expression of the DNA of the present invention for an animal, in which the DNA of the present invention is inactivated by introducing a reporter gene and the reporter gene can be expressed under control of a promoter to the DNA of the present invention. The same examples given above for the test compound apply to the test compound. As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is substituted with a reporter gene, the reporter gene is present under control of a promoter to the DNA of the present invention. Thus, the activity of the promoter can be detected by tracing the expression of a substance encoded by the reporter gene.

For example, when a part of the DNA region encoding the polypeptide of the present invention is substituted with, e.g., β-galactosidase gene (lacZ) derived from *Escherichia coli*, β-galactosidase is expressed in a tissue where the polypeptide of the present invention should originally be expressed, in place of the polypeptide of the present invention. Thus, the expression state of the polypeptide of the present invention can be readily observed in vivo of an animal, by staining with a reagent, e.g., 5-bromo-4-chloro-3-indolyl-β-D-galactopyranoside (X-gal), which is a substrate for β-galactosidase. Specifically, a mouse deficient in the polypeptide of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening methods supra are compounds selected from the test compounds described above, which promote or inhibit the promoter activity for the DNA of the present invention.

The compound obtained by the screening methods may be in the form of salts. The salts of the compound used are salts with physiologically acceptable acids (e.g., inorganic acids) or bases (e.g., organic acids), and physiologically acceptable acid addition salts are preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compounds or salts thereof that promote the promoter activity to the DNA of the present invention can promote the expression of the polypeptide of the present invention, or can promote the functions of the polypeptide, they are useful as safe and low toxic pharmaceuticals for the treatment/prevention, etc. of various diseases such as abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc.

In addition, compound derived from the compounds obtained by the screening above may be employed as well.

A pharmaceutical containing the compounds or salts thereof obtained by the screening methods supra may be prepared in a manner similar to the method for preparing the pharmaceutical containing the polypeptide of the present invention or its salts described above.

Since the pharmaceutical preparation thus obtained is safe and low toxic, it can be administered to mammal (e.g., human, rat, mouse, guinea pig, rabbit, sheep, swine, bovine, horse, cat, dog, monkey, etc.).

The dose of the compound or salts thereof varies depending on target disease, subject to be administered, route for administration, etc.; for example, when the compound that promotes the promoter activity to the DNA of the present invention is orally administered for the purpose of treating, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., they may be administered to adult (as 60 kg body weight) normally in a daily dose of about 0.01 to about 1000 mg, preferably about 0.1 to about 1000 mg, more preferably about 1.0 to about 200 mg, most preferably about 1.0 to about 50 mg. In parenteral administration, a single dose of the compound may vary depending upon subject to be administered, target disease, etc.; when the compound that promotes the promoter activity to the DNA of the present invention is administered in the form of injectable preparation for the purpose of treating, for example, abnormalities (e.g., diabetes mellitus, obesity, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), arteriosclerosis, endocrine disruption, abnormality of body fluid balance, central diseases, immune system diseases (e.g., allergy, inflammation, autoimmune disease, etc.), angiogenic disorders, etc., it is advantageous to administer the compound intravenously to adult (as 60 kg) in a daily dose of about 0.01 to about 30 mg, preferably about 0.1 to about 20 mg, more preferably about 0.1 to about 10 mg. For other animal species, the corresponding dose as converted per 60 kg can be administered.

On the other hand, for example, when the compound that inhibits the promoter activity to the DNA of the present invention is orally administered, the compound is administered to adult (as 60 kg body weight) in a daily dose of approximately 0.1 to 1000 mg, preferably approximately 1.0 to 200 mg, more preferably approximately 1.0 to 50 mg. In parenteral administration, a single dose of the compound may vary depending on subject to be administered, target disease, etc.; when the compound that inhibits the promoter activity to the DNA of the present invention is administered to adult (as 60 kg) in the form of injectable preparation, it is advantageous to administer the compound intravenously in a daily dose of approximately 0.01 to 30 mg, preferably approximately 0.1 to 20 mg, more preferably approximately 0.1 to 10 mg. For other animal species, the corresponding dose as converted per 60 kg weight can be administered.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly or G | glycine |
| Ala or A | alanine |
| Val or V | valine |
| Leu or L | leucine |
| Ile or I | isoleucine |
| Ser or S | serine |
| Thr or T | threonine |
| Cys or C | cysteine |
| Met or M | methionine |
| Glu or E | glutamic acid |
| Asp or D | aspartic acid |
| Lys or K | lysine |
| Arg or R | arginine |
| His or H | histidine |
| Phe or F | phenylalanine |
| Tyr or Y | tyrosine |
| Trp or W | tryptophan |
| Pro or P | proline |
| Asn or N | asparagine |
| Gln or Q | glutamine |

-continued

| | |
|---|---|
| pGlu | pyroglutamic acid |
| Hse | homoserine |

Also, substituents, protecting groups, and reagents frequently used in this specification are presented by the codes below.

| | |
|---|---|
| Me | methyl group |
| Et | ethyl group |
| Bu | butyl group |
| Ph | phenyl group |
| TC | thiazolidine-4(R)-carboxamido group |
| Tos | p-toluenesulfonyl |
| CHO | formyl |
| Bzl | benzyl |
| $Cl_2Bzl$ | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dichlorohexylcarbodiimide |

The sequence identification numbers in the sequence listing of the specification indicates the following sequence, respectively.

[SEQ ID NO:1]

This shows the base sequence of the primer used in EXAMPLE 1.

[SEQ ID NO:2]

This shows the base sequence of the primer used in EXAMPLES 1 and 3.

[SEQ ID NO:3]

This shows the amino acid sequence of the novel protein precursor (human type) of the present invention.

[SEQ ID NO:4]

This shows the base sequence of cDNA fragment encoding the novel protein precursor (human type) of the present invention found in EXAMPLES 1 and 2.

[SEQ ID NO:5]

This shows the base sequence of the primer used in EXAMPLES 2 and 4.

[SEQ ID NO:6]

This shows the base sequence of the primer used in EXAMPLE 4.

[SEQ ID NO:7]

This shows the amino acid sequence of A chain (human type) in the novel polypeptide.

[SEQ ID NO:8]

This shows the amino acid sequence of B chain (human type) in the novel polypeptide.

[SEQ ID NO:9]

This shows the base sequence of the primer used in EXAMPLE 2.

[SEQ ID NO:10]

This shows the base sequence of the primer used in EXAMPLE 2.

[SEQ ID NO:1]

This shows the base sequence of the primer used in EXAMPLE 2.

[SEQ ID NO:12]

This shows the base sequence of open reading frame (ORF) in the cDNA fragment encoding the novel protein precursor (human type) of the present invention obtained in EXAMPLE 3.

[SEQ ID NO:13]

This shows the base sequence of the primer used in EXAMPLE 3.

[SEQ ID NO:14]

This shows the base sequence of the primer used in EXAMPLE 3.

[SEQ ID NO:15]

This shows the base sequence of DNA encoding A chain (human type).

[SEQ ID NO:16]

This shows the base sequence of DNA encoding B chain (human type).

[SEQ ID NO:17]

This shows the amino acid sequence of the novel protein precursor (rat type) of the present invention.

[SEQ ID NO:18]

This shows the amino acid sequence of the DNA encoding the amino acid sequence shown by SEQ ID NO:17.

[SEQ ID NO:19]

This shows the amino acid sequence of A chain (rat type, mouse type).

[SEQ ID NO:20]

This shows the base sequence of the DNA encoding the amino acid sequence of A chain (rat type).

[SEQ ID NO:21]

This shows the amino acid sequence of B chain (rat type, mouse type).

[SEQ ID NO:22]

This shows the base sequence of the DNA encoding the amino acid sequence of B chain (rat type).

[SEQ ID NO:23]

This shows the amino acid sequence of the novel protein precursor (mouse type) of the present invention.

[SEQ ID NO:24]

This shows the base sequence of the DNA encoding the amino acid sequence shown by SEQ ID NO:23.

[SEQ ID NO:25]

This shows the base sequence of DNA encoding mouse MLP bearing the amino acid sequence shown by SEQ ID NO:26.

[SEQ ID NO:26]

This shows the base sequence of the DNA encoding the amino acid sequence of B chain (mouse type).

[SEQ ID NO:27]

This shows the base sequence of primer R1 employed in EXAMPLE 5, which will be later described.

[SEQ ID NO:28]

This shows the base sequence of primer R2 employed in EXAMPLE 5, which will be later described.

[SEQ ID NO:29]

This shows the base sequence of primer L1 employed in EXAMPLE 5, which will be later described.

[SEQ ID NO:30]

This shows the base sequence of primer R8 employed in EXAMPLE 5, which will be later described.

[SEQ ID NO:31]

This shows the base sequence of primer R9 employed in EXAMPLE 5, which will be later described.

[SEQ ID NO:32]

This shows the base sequence of primer R6 employed in EXAMPLE 5, which will be later described.

[SEQ ID NO:33]

This shows the base sequence of primer R7 employed in EXAMPLE 5, which will be later described.

[SEQ ID NO:34]

This shows the base sequence of primer U1 employed in EXAMPLE 5, which will be later described.

[SEQ ID NO:35]

This shows the base sequence of primer U2 employed in EXAMPLE 5, which will be later described.

[SEQ ID NO:36]

This shows the base sequence of primer UP employed in EXAMPLES 6 and 7, which will be later described.

[SEQ ID NO:37]

This shows the base sequence of primer RL employed in EXAMPLE 6, which will be later described.

[SEQ ID NO:38]

This shows the base sequence of primer ML employed in EXAMPLE 7, which will be later described.

[SEQ ID NO:39]

This shows the base sequence of the DNA containing rat ORF obtained in EXAMPLE 6, which will be later described.

[SEQ ID NO:40]

This shows the base sequence of the DNA containing mouse ORF obtained in EXAMPLE 7, which will be later described.

[SEQ ID NO:41]

This shows the base sequence of the first exon region in the DNA encoding the rat type precursor clarified in EXAMPLE 5, which will be later described.

[SEQ ID NO:42]

This shows the base sequence of the second exon region in the DNA encoding the rat type precursor clarified in EXAMPLE 5, which will be later described.

[SEQ ID NO:43]

This shows the base sequence of the first exon region in the DNA encoding the mouse type precursor clarified in EXAMPLE 5, which will be later described.

[SEQ ID NO:44]

This shows the base sequence of the second exon region in the DNA encoding the mouse type precursor clarified in EXAMPLE 5, which will be later described.

[SEQ ID NO:45]

This shows the amino acid sequence of the novel protein precursor (porcine type) of the present invention.

[SEQ ID NO:46]

This shows the base sequence of the DNA encoding the amino acid sequence represented by SEQ ID NO:45.

[SEQ ID NO:47]

This shows the amino acid sequence of A chain (porcine type).

[SEQ ID NO:48]

This shows the base sequence of the DNA encoding the amino acid sequence of A chain (porcine type).

[SEQ ID NO:49]

This shows the amino acid sequence of B chain (porcine type).

[SEQ ID NO:50]

This shows the base sequence of the DNA encoding the amino acid sequence of B chain (porcine type).

[SEQ ID NO:51]

This shows the amino acid sequence of the novel protein precursor (rat type variant) of the present invention.

[SEQ ID NO:52]

This shows the base sequence of the DNA encoding the amino acid sequence shown by SEQ ID NO:51.

[SEQ ID NO:53]

This shows the base sequence of sense strand primer ex1F1 used in EXAMPLE 8, which will be described later.

[SEQ ID NO:54]

This shows the base sequence of antisense strand primer ex1R1 used in EXAMPLE 8, which will be described later.

[SEQ ID NO:55]

This shows the base sequence of the DNA encoding the N-terminus to the B chain peptide via the signal peptide of the porcine type precursor protein obtained in EXAMPLE 8, which will be described later.

[SEQ ID NO:56]

This shows the base sequence of the PCR product obtained in EXAMPLE 8 the base sequence of sense strand primer ex1F1 used in EXAMPLE 8, which will be described later.

[SEQ ID NO:57]

This shows the base sequence of oligo DNA (PORex1F1) used in EXAMPLE 8, which will be described later.

[SEQ ID NO:58]

This shows the base sequence of oligo DNA (PORex1F2) used in EXAMPLE 8, which will be described later.

[SEQ ID NO:59]

This shows the base sequence of the first exon region in the DNA encoding the porcine type precursor clarified in EXAMPLE 8, which will be later described.

[SEQ ID NO:60]

This shows the base sequence of the second exon region in the DNA encoding the porcine type precursor clarified in EXAMPLE 8, which will be later described.

[SEQ ID NO:61]

This shows the base sequence of the DNA containing open reading frame (ORF) encoding the rat type precursor variant clarified in EXAMPLE 9, which will be described later.

[SEQ ID NO:62]

This shows the base sequence of the DNA encoding a part of the rat type precursor variant clarified in EXAMPLE 9, which will be described later.

[SEQ ID NO:63]

This shows the amino acid sequence encoded by the DNA base sequence shown by SEQ ID NO:62 clarified in EXAMPLE 9, which will be described later.

[SEQ ID NO:64]

This shows the base sequence of the sense strand primer employed in EXAMPLE 19, which will be described later.

[SEQ ID NO:65]

This shows the base sequence of the antisense strand primer employed in EXAMPLE 19, which will be described later.

[SEQ ID NO:66]

This shows the base sequence of the sense strand primer employed in EXAMPLE 19, which will be described later.

[SEQ ID NO:67]

This shows the base sequence of the antisense strand primer employed in EXAMPLE 19, which will be described later.

[SEQ ID NO:68]

This shows the base sequence of the DNA encoding the fused protein obtained in EXAMPLE 19, which will be described later.

[SEQ ID NO:69]

This shows the amino acid sequence of the fused protein obtained in EXAMPLE 19, which will be described later.

[SEQ ID NO:70]

This shows the base sequence of the sense strand primer employed in EXAMPLE 23, which will be described later.

[SEQ ID NO:71]

This shows the base sequence of the antisense strand primer employed in EXAMPLE 23, which will be described later.

[SEQ ID NO:72]

This shows the base sequence of the oligo DNA segment of TaqMan probe employed in EXAMPLE 23, which will be described later.

[SEQ ID NO:73]

This shows the base sequence of the sense strand primer employed in EXAMPLE 23, which will be described later.

[SEQ ID NO:74]

This shows the base sequence of the antisense strand primer employed in EXAMPLE 23, which will be described later.

[SEQ ID NO:75]

This shows the base sequence of the oligo DNA segment of TaqMan probe employed in EXAMPLE 23, which will be described later.

[SEQ ID NO:76]

This shows the base sequence of the sense strand primer employed in EXAMPLE 23, which will be described later.

[SEQ ID NO:77]

This shows the base sequence of the antisense strand primer employed in EXAMPLE 23, which will be described later.

[SEQ ID NO:78]

This shows the base sequence of the oligo DNA segment of TaqMan probe employed in EXAMPLE 23, which will be described later.

[SEQ ID NO:79]

This shows the base sequence of synthetic DNA employed in EXAMPLE 29, which will be described later.

[SEQ ID NO:80]

This shows the base sequence of synthetic DNA employed in EXAMPLE 29, which will be described later.

[SEQ ID NO:81]

This shows the base sequence of synthetic DNA employed in EXAMPLE 29, which will be described later.

[SEQ ID NO:82]

This shows the base sequence of synthetic DNA employed in EXAMPLE 29, which will be described later.

[SEQ ID NO:83]

This shows the base sequence of synthetic DNA employed in EXAMPLE 29, which will be described later.

[SEQ ID NO:84]

This shows the base sequence of synthetic DNA employed in EXAMPLE 30, which will be described later.

[SEQ ID NO:85]

This shows the base sequence of synthetic DNA employed in EXAMPLE 30, which will be described later.

[SEQ ID NO:86]

This shows the base sequence of synthetic DNA employed in EXAMPLE 30, which will be described later.

Transformant *Escherichia coli* INVαF'/pVH7U5Lh obtained in EXAMPLE 1 later described has been deposited with the Ministry of International Trade and Industry, Agency of Industrial Science and Technology, National Institute of Bioscience and Human-Technology (NIBH) at No. 1–3, Higashi 1-chome, Tsukuba-shi, Ibaraki-ken, Japan, under the Accession Number FERM BP-7130 since Apr. 12, 2000, and with Institute for Fermentation, Osaka (IFO) at No. 17–85, Juso-honmachi 2-chome, Yodogawa-ku, Osaka, Japan, under the Accession Number IFO 16423 since Apr. 18, 2000. Transformant *Escherichia coli* transformant INVαF'/pVHNC5Lh obtained in EXAMPLE 3 later described has been deposited with the Ministry of International Trade and Industry, Agency of Industrial Science and Technology, National Institute of Bioscience and Human-Technology (NIBH) at No. 1–3, Higashi 1-chome, Tsukuba-shi, Ibaraki-ken, Japan, under the Accession Number FERM BP-7139 since Apr. 18, 2000, and with Institute for Fermentation, Osaka (IFO) at No. 17–85, Juso-honmachi 2-chome, Yodogawa-ku, Osaka, Japan, under the Accession Number IFO 16424 since Apr. 18, 2000. Plasmid pVHUPTr obtained in EXAMPLE 6 later described has been deposited with the Ministry of International Trade and Industry, Agency of Industrial Science and Technology, National Institute of Bioscience and Human-Technology (NIBH) at No. 1–3, Higashi 1-chome, Tsukuba-shi, Ibaraki-ken, Japan, under the Accession Number FERM BP-7204 since Jul. 3, 2000. Transformant *Escherichia coli* TOP10/pVHUPTr obtained in EXAMPLE 6 later described has been deposited with Institute for Fermentation, Osaka (IFO) at No. 17–85, Juso-honmachi 2-chome, Yodogawa-ku, Osaka, Japan, under the Accession Number IFO 16455 since Jul. 17, 2000. Plasmid pVHUPTm obtained in EXAMPLE 7 later described has been deposited with the Ministry of International Trade and Industry, Agency of Industrial Science and Technology, National Institute of Bioscience and Human-Technology (NIBH) at No. 1–3, Higashi 1-chome, Tsukuba-shi, Ibaraki-ken, Japan, under the Accession Number FERM BP-7205 since Jul. 3, 2000. Transformant *Escherichia coli* TOP10/pVHUPTm obtained in EXAMPLE 7 later described has been deposited with Institute for Fermentation, Osaka (IFO) at No. 17–85, Juso-honmachi 2-chome, Yodogawa-ku, Osaka, Japan, under the Accession Number IFO 16454 since Jul. 17, 2000. Transformant *Escherichia coli* TOP10/pVHABDr obtained in EXAMPLE 9 later described has been deposited with the Ministry of International Trade and Industry, Agency of Industrial Science and Technology, National Institute of Bioscience and Human-Technology (NIBH) at No. 1–3, Higashi 1-chome, Tsukuba-shi, Ibaraki-ken, Japan, under the Accession Number FERM BP-7268 since Aug. 10, 2000, and with Institute for Fermentation, Osaka (IFO) at No. 17–85, Juso-honmachi 2-chome, Yodogawa-ku, Osaka, Japan, under the Accession Number IFO 16461 since Aug. 3, 2000. Transformant *Escherichia coli* BL21-Gold (DE3)/pETVHMMh obtained in EXAMPLE 19 later described has been deposited with Institute for Fermentation, Osaka (IFO) at No. 17–85, Juso-honmachi 2-chome, Yodogawa-ku, Osaka, Japan, under the Accession Number IFO 16531 FERM BP-8043 since Feb. 1, 2001. Hybridoma HK4-144-10 obtained in EXAMPLE 14 later described has been deposited with the Ministry of International Trade and Industry, Agency of Industrial Science and Technology, National Institute of Bioscience and Human-Technology (NIBH) at No. 1–3, Higashi 1-chome, Tsukuba-shi, Ibaraki-ken, Japan, under the Accession Number FERM BP-7520 since Mar. 26, 2001.

EXAMPLES

Hereinafter, the present invention will be specifically described with reference to EXAMPLES, but is not limited thereto. The gene manipulation procedures using *Escherichia coli* were performed in accordance with the methods described in the Molecular Cloning.

Example 1

Cloning of cDNA Encoding the Novel Polypeptide cDNA encoding the novel polypeptide of the present invention was acquired by the following PCR. There was prepared a 50 μl mixture containing 5 pmols of the oligo DNA (CTGGCGGTATGGGTGCTGAC) shown by SEQ ID NO:1 as a sense strand primer, 5 pmols of the oligo DNA (ACTGGGGCATTGGTCCTGGTG) shown by SEQ ID NO:2 as an antisense strand primer, 5 μl of 100 mM Tris-hydrochloride buffer (pH 9.0), 5 pi of 500 mM potassium chloride solution, 3 μl of 25 mM magnesium chloride solution, 4 μl of 2.5 mM deoxyribonucleotide solution, 1 μl of cDNA solution prepared from Human Testis polyA™ RNA (Clontech) as a template DNA, and 0.5 μl of TaKaRa Taq™ Using TaKaRa PCR Thermal Cycler MP (Takara Shuzo Co., Ltd.), PCR was carried out by the program to first maintain at 95° C. for 1 minute, then repeat the reaction cycle set to include 95° C. for 30 seconds, 65° C. for 1 minute and 72° C. for 1 minute 35 times, and then react at 72° C. for further 10 minutes. After completion of the reaction, the reaction solution was electrophoresed on 1.0% agarose gel and stained with ethidium bromide, whereby the band corresponding to the DNA amplified by the PCR was confirmed at the position around 0.45 kb as converted by a molecular marker. After the DNA fragment was recovered using GENE CLEAN SPIN KIT (BIO101, Inc.) and subjected to TA cloning using pCR (registered trademark) 2.1 (Invitrogen, Inc.) to determine the base sequence, the plasmid was introduced into competent cells of *E. coli* INVαF' strain. Clones bearing the foreign DNA fragment-inserted plasmid were selected from the colonies of ampicillin-resistant transformants appeared on ampicillin-containing LB agar medium, to prepare the plasmid DNA, pVH7U5Lh. In order to determine the base sequence of the inserted DNA, sequencing was performed on TaKaRa PCR Thermal Cycler MP (Takara Shuzo Co., Ltd.) under the conditions of the attached brochure using ABI PRISM™ BigDye Terminator Cycle Sequencing FS Ready Reaction Kit (Perkin-Elmer, Inc.), using pVH7U5Lh as a template and the oligo DNAs shown by SEQ ID NO:1 and SEQ ID NO:2 as sequencing primers. Thereafter, the reaction sample was analyzed by DNA Sequencer ABI PRISM™ 377 (Perkin-Elmer, Inc.).

The results revealed that pVH7U5Lh encoded the base sequence corresponding to the 49th to 494th shown by SEQ ID NO:4, that is, the region corresponding to the amino acid sequence of the C-terminal 133 residues except for the N-terminal 9 amino acid residues, in the novel polypeptide shown by SEQ ID NO:3, composed of 142 amino acids. In the amino acid sequence of the corresponding region, the primary structure characteristic of the insulin/IGF/relaxin family (N-terminal hydrophobic domain, the A chain (SEQ ID NO:7) and B chain (SEQ ID NO:8) inserted between basic amino acid residues and having Cys residues) was observed in the corresponding amino acid sequence.

The thus acquired plasmid pVH7U5Lh was transfected to *Escherichia coli* INVαF' to give *Escherichia coli* INVαF'/pVH7U5Lh.

Example 2

Analysis of cDNA Encoding the Novel Polypeptide by 5' RACE and 3' RACE

Following the procedures below, the full-length cDNA encoding the novel polypeptide was analyzed by performing 5' RACE (Rapid Amplification of cDNA End) PCR and 3' RACE PCR. For a template DNA of the RACE PCR, Marathon™-Ready cDNA Human Testis (Clontech) was employed. In the primary PCR of 5' RACE, the oligo DNA shown by SEQ ID NO:9 was used as an antisense strand primer and AP1 attached to Marathon™-Ready cDNA Human Testis was used as a sense strand primer, based on the inserted DNA sequence of pVH7U5Lh obtained in EXAMPLE 1. In the following nested PCR, the oligo DNA shown by SEQ ID NO:10 was used as an antisense strand primer and as a sense strand primer, AP2 attached to Marathon™-Ready cDNA Human Testis was used. The reaction was carried out under the conditions given in the manual attached to the kit, and the cycle for PCR was repeated 35 times and in the subsequent nest PCR, the cycle was repeated 20 times. The amplified PCR fragments were separated on 2.0% agarose gel and recovered by electrophoresis and elution. Then, the base sequence of the PCR fragment was directly determined using the synthetic DNA shown by SEQ ID NO:10 as a sequencing primer. The results newly revealed the base sequence corresponding to the 1st to the 48th, which is shown by SEQ ID NO:4, and the amino acid sequence corresponding to the 1st to the 9th, which is shown by SEQ ID NO:3.

Next, based on the inserted DNA sequence of pVH7U5Lh obtained in EXAMPLE 1, 3' RACE PCR was performed by the following procedures. Using the oligo DNA shown by SEQ ID NO:5 as a sense strand primer and AP1 attached to Marathon™-Ready cDNA Human Testis as an antisense strand primer in the primary PCR, and in the following nested PCR, using the oligo DNA shown by SEQ ID NO:11 as a sense strand primer and AP2 attached to Marathon™-Ready cDNA Human Testis as an antisense strand primer, the reaction was carried out. After completion of the reaction, the product was electrophoresed on 2.0% agarose gel and stained with ethidium bromide, whereby the band corresponding to the PCR product was detected at the position of 0.7 kb. Thus, the DNA fragment was recovered and purified using QIAquick Gel Extraction Kit (Qiagen). After the DNA fragment was subjected to TA cloning using pCR (registered trademark) 2.1-TOPO (Invitrogen, Inc.) to determine the base sequence, the plasmid was introduced into competent cells of *E. coli* DH5a strain. Four clones bearing the foreign DNA fragment-inserted plasmid were selected from the colonies of ampicillin-resistant transformants appeared on ampicillin-containing LB agar medium, to prepare the plasmid DNA. Thereafter the base sequence of the inserted DNA fragment was determined. The results revealed that the DNA fragment bearing the base sequence corresponding to the 413th to the 1061st shown by SEQ ID NO:4 starting from the nested primer shown by SEQ ID NO:11 and the following poly A sequence further added to the 3' end, was inserted in the plasmids of all clones. From the foregoing results, the open reading frame shown by SEQ ID NO:4 was clarified, and based on the characteristics (signal sequence, A chain (SEQ ID NO:7) and B chain (SEQ ID NO:8) inserted between basic amino acid residues and having Cys residues) of the protein shown by SEQ ID NO:3 encoded by the open reading frame, the novel protein of the present invention was found to be a novel secretory biological function regulatory protein precursor belonging to the insulin/IGF/relaxin family (FIG. 1).

Example 3

Cloning of Full-Length cDNA Encoding the Novel Polypeptide (Precursor Polypeptide)

The full-length cDNA encoding the novel polypeptide (precursor polypeptide) was acquired by the 5'-RACE method as described below.

Using the 5'-RACE System (GIBCO BRL), a solution of cDNA was prepared by reverse transcription wherein Human Testis poly $A^+$ RNA (Clontech) was employed as a template, using as a primer the oligo DNA (GGGCAGGGGTCTCTGTGT) shown by SEQ ID NO:13 prepared based on the inserted DNA sequence of pVH7U5Lh obtained in EXAMPLE 1. Using this cDNA as a template, the primary PCR was carried out using AAP attached to the 5'-RACE System as a sense strand primer and the oligo DNA supra shown by SEQ ID NO:13 as an antisense strand primer. Next, the nested PCR was performed using as a sense strand primer the oligo DNA (TTCAAAGCATCTCCGTCCAGC) shown by SEQ ID NO:14 prepared based on the inserted DNA sequence of pVH7U5Lh obtained in EXAMPLE 1 and as an antisense strand primer the oligo DNA supra (ACTGGGGCATTGGTCCTGGTG) shown by SEQ ID NO:2. After completion of the reaction, the reaction solution was electrophoresed on 1.0% agarose gel and stained with ethidium bromide, whereby the band was detected at the position of 0.5 kb. Next, the DNA fragment was recovered using GENE CLEAN SPIN KIT (BIO110, Inc.) and subjected to TA cloning using pCR (registered trademark) 2.1 (Invitrogen, Inc.) to determine the base sequence. The plasmid was then introduced into competent cells of *E. coli* INVαF' strain. Clones bearing the foreign DNA fragment-inserted plasmid were selected from the colonies of ampicillin-resistant transformants appeared on ampicillin-containing LB agar medium, to prepare the plasmid DNA, pVHNC5Lh. In order to determine the base sequence of the inserted DNA, sequencing was performed on TaKaRa PCR Thermal Cycler MP (Takara Shuzo Co., Ltd.) under the conditions of the attached brochure using ABI PRISM™ BigDye Terminator Cycle Sequencing FS Ready Reaction Kit (Perkin-Elmer, Inc.), using pVHNC5Lh as a template and as sequencing primers the oligo DNA (TTCAAAGCATCTCCGTCCAGC) shown by SEQ ID NO:14 and the oligo DNA (ACTGGGGCATTGGTCCTGGTG) shown by SEQ ID NO:2. Thereafter, the reaction sample was analyzed by DNA Sequencer ABI PRISM™ 377 (Perkin-Elmer, Inc.).

The results revealed that pVHNC5Lh contained the base sequence corresponding to the 1st to 494th shown by SEQ ID NO:4, that is, the open reading frame (ORF) encoding the novel polypeptide composed of 142 amino acids shown by SEQ ID NO:3 (FIG. 1).

The thus acquired plasmid pVHNC5Lh was transfected to *Escherichia coli* INVαF' to give *Escherichia coli* INVαF/pVHNC5Lh.

Example 4

Analysis of the Novel Polypeptide on Tissue Expression Distribution

By the PCR described below, tissues to express the novel polypeptide were examined. First, there was prepared 25 μl of a mixture containing 2.5 pmols of the oligo DNA (CCGGATGCAGATGCTGATGAA) shown by SEQ ID NO:5 as a sense strand primer, 2.5 pmols of the oligo DNA (TGGTCAAAGGGCAGGGTTGG) shown by SEQ ID NO:6 as an antisense strand primer, 2.5 μl of 100 mM Tris-hydrochloride buffer (pH 9.0), 2.5 μl of 500 mM potassium chloride solution, 1.5 μl of 25 mM magnesium chloride solution, 2 μl of 2.5 mM deoxyribonucleotide solution, 1 μl of a cDNA solution of each tissue from Human Multiple Tissue cDNA (MTC™) panels (Clontech) as a template DNA, and 0.25 μl of TaKaRa Taq™. PCR was carried out by the program to first maintain at 95° C. for 1 minute, then repeat the reaction cycle set to include 95° C. for 30 seconds, 66° C. for 1 minute and 72° C. for 1 minute 35 times. After completion of the reaction, the reaction solution was electrophoresed on 1.5% agarose gel and stained with ethidium bromide to examine if the amplified product was produced. The results revealed that the 0.45 kb DNA fragment derived from the DNA encoding the novel polypeptide was detected mainly in the reaction solutions of placenta, lung, testis, pituitary, etc., indicating that the novel polypeptide was expressed in these vital tissues (FIG. 2).

Example 5

Chromosomal Genes Encoding the Rat Counterpart and Mouse Counterpart of the Novel Polypeptide (Precursor Polypeptide) and cDNA Sequencing For cloning of cDNAs encoding the rat and mouse counterparts of the human-derived novel polypeptide (precursor polypeptide) obtained in EXAMPLE 3, the structures of the chromosomal genes in the two animal species were first analyzed by the genome walking method described below. For test materials, Rat GenomeWalker™ Kit (Clontech) and Mouse GenomeWalker™ Kit (Clontech) were employed for rat and mouse chromosomal DNAs, respectively. PCR was conducted following the procedures given in the instructions attached to the respective kits, except that TaKaRa Ex Taq™ (Takara Shuzo Co., Ltd.) was used as an enzyme for PCR. In the first genome walking toward the 5' upstream direction, based on the base sequences of EST, AW523625 and AW521175 considered to include the 3' end site of CDNA encoding the rat counterpart of the human novel polypeptide (precursor polypeptide) shown by SEQ ID NO:12, which was found from public EST (Expressed Sequence Tag) database by querying against the base sequence of cDNA encoding the polypeptide, 3 oligo DNAs (R1 (SEQ ID NO:27), R2 (SEQ ID NO:28) and L1 (SEQ ID NO:29)) having sequences complementary to a part of these base sequences were chemically synthesized and made gene specific primers. As a result, with regard to the rat chromosomal DNA, the amplified specific DNA fragments were obtained in the reaction systems using R1 for the first PCR and R2 for the subsequent nested PCR, respectively. In these DNA fragments, the base sequence derived from each genome having the adapter primer (AP2) sequence at the terminus was determined by a modification of the method described in EXAMPLES above. Based on the sequence, new gene specific primers were designed to further proceed the second genome walking toward the 5' upstream direction. That is, these primers were 4 oligo DNAs in total of R8 (SEQ ID NO:30) for the first PCR and R9 (SEQ ID NO:31) for the nested PCR on the rat chromosomal DNA, and R6 (SEQ ID NO:32) for the first PCR and R7 (SEQ ID NO:33) for the nested PCR on the mouse chromosomal DNA. Using these primers, PCR was again performed on each DNA sample from Rat GenomeWalker™ Kit and Mouse GenomeWalker™ Kit DNA under the same conditions. The amplified specific DNA fragments were newly obtained with rat and mouse, respectively. Thus, the base sequence of each of the DNA fragments obtained by the first genome walking supra as well as the amplified DNA fragments was determined. While comparing homology to the base sequence of the cDNA encoding the human novel polypeptide (precursor polypeptide) obtained in EXAMPLE 3, sequencing analysis was made.

The results revealed that the rat counterpart of the human novel polypeptide (precursor polypeptide) was a polypeptide composed of 140 amino acids shown by SEQ ID NO:17, encoded by the DNA of 420 bases shown by SEQ ID NO:18; and that the gene was composed of two exons intervened by one intervening sequence on the rat chromosome, and in the 420 bases, 184 bases shown by SEQ ID NO:41 and 236 bases shown by SEQ ID NO:42 were encoded by the first exon and the second exon, respectively. The polypeptide contained sequences characteristic of the insulin/IGF/relaxin family as in the human novel polypeptide (precursor polypeptide), i.e., the signal sequence as well as the A chain (SEQ ID NO:19) and the B chain (SEQ ID NO:20) inserted between basic amino acids and having Cys residues. The rat novel polypeptide had 75.0% homology to the human novel polypeptide.

Since, also with mouse, a sequence considered to be the 5' end site of the novel polypeptide counterpart gene was obtained in the experiment described above, 3' RACE PCR was performed to examine the sequence at the remaining 3' end as well as the expression as mRNA. Marathon™-Ready cDNA Mouse Testis (Clontech) was used as a template DNA for the RACE PCR, and 2 oligo DNAs (U1 (SEQ ID NO:34) and U2 (SEQ ID NO:35)) designed based on the sequence corresponding to the second exon site obtained in the first genome walking were chemically synthesized for gene specific primers, respectively. In the first PCR, U1 was used as a sense strand primer and AP1 attached to Marathon™-Ready cDNA Mouse Testis was used as an antisense strand primer, and U2 and AP2 attached to Marathon™-Ready cDNA Mouse Testis were used as a sense strand primer and an antisense strand primer, respectively, in the subsequent nested PCR. As a result of these PCRs, a single DNA fragment was obtained as the final amplified product, which was subjected to base sequencing by a modification of the method described above. The DNA fraction contained the base sequence corresponding to the mouse second exon site, starting from U2 and ending with the termination codon, and further containing the poly A-added signal sequence and poly A sequence at the end of the untranslational region of the 3' side. From this cDNA partial sequence and the primary structure of the mouse chromosomal DNA fragment obtained in this EXAMPLE, it was revealed that the mouse counterpart of the novel polypeptide (precursor polypeptide) was a polypeptide composed of 141 amino acid residues shown by SEQ ID NO:23 encoded by the DNA of 423 bases shown by SEQ ID NO:24, and as in rat, the gene was composed of two exons intervened by one intervening sequence on the rat chromosome, and in the 423 bases, 187 bases shown by SEQ ID NO:43 and 236 bases shown by SEQ ID NO:44 were encoded by the first exon and the second exon, respectively. The polypeptide contained sequences characteristic of the insulin/IGF/relaxin family as in the human novel polypeptide or the rat novel polypeptide, i.e., the signal sequence as well as the A chain (SEQ ID NO:19) and the B chain (SEQ ID NO:21) inserted between basic amino acids and having Cys residues. The mouse novel polypeptide had 77.3% and 92.1% homology to the human novel polypeptide and the rat novel polypeptide, respectively, and the amino acid sequences of A and B chains completely coincided with those derived from rat.

Example 6

Cloning of the Full-length cDNA Encoding the Rat Counterpart of the Novel Polypeptide (Precursor Polypeptide)

The full-length cDNA encoding the rat counterpart of the novel polypeptide was acquired by performing the PCR described below.

First, there was prepared a 50 pi mixture containing 5 pmols each of the oligo DNA (UP (SEQ ID NO:36)) chemically synthesized based on the base sequence of the 5' side untranslational region of the novel polypeptide mouse counterpart gene obtained in EXAMPLE 5 as a sense strand primer and the oligo DNA (RL (SEQ ID NO:37)) chemically synthesized based on the base sequences of public EST, AW523625 and AW521175 described in EXAMPLE 5 as an antisense strand primer, 5 µl of 100 mM Tris-hydrochloride buffer (pH 8.3), 5 µl of 500 mM potassium chloride solution, 3 µl of 25 mM magnesium chloride solution, 4 µl of 2.5 mM deoxyribonucleotide solution, 4 µl of cDNA solution prepared from the total RNA derived from SD rat (9 weeks old) testis as a template DNA, and 0.5 µl of TaKaRa Taq™ (Takara Shuzo Co., Ltd.). Next, the reaction mixture was subjected to the following reaction using TaKaRa PCR Thermal Cycler MP (Takara Shuzo Co., Ltd.) to first maintain at 95° C. for 1 minute, then repeat the reaction cycle set to include 95° C. for 30 seconds, 67° C. for 1 minute and 72° C. for 1 minute 40 times, and then react at 72° C. for further 10 minutes. After completion of the reaction, the reaction solution was electrophoresed on 1.0% agarose gel and stained with ethidium bromide, whereby the band corresponding to the DNA amplified by the PCR was confirmed at the position around 0.45 kb as converted by a molecular marker. Next, the DNA fragment was recovered using GENE CLEAN SPIN KIT (BIO101, Inc.) and subjected to TA cloning using pCR (registered trademark) 2.1-TOPO (Invitrogen, Inc.) to determine the base sequence, and the plasmid was introduced into competent cells (Invitrogen) of *E. coli* TOP10 strain. A clone bearing the foreign DNA fragment-inserted plasmid was selected from the colonies of ampicillin-resistant transformants appeared on ampicillin-containing LB agar plate medium. The plasmid DNA, pVHUPTr was prepared from the clone and the base sequence of the inserted DNA was determined.

The results revealed that pVHUPTr contained the DNA fragment of 470 base pairs shown by SEQ ID NO:39 containing the open reading frame (ORF) composed of 420 bases shown by SEQ ID NO:18, encoding the rat counterpart of the novel polypeptide precursor composed of 140 amino acids shown by SEQ ID NO:17.

The thus acquired plasmid pVHUPTr bearing the DNA encoding the rat novel polypeptide (precursor polypeptide) was transfected to *Escherichia coli* TOP10 to give *Escherichia coli* TOP10/pVHUPTr.

Example 7

Cloning of the Full-length CDNA Encoding the Mouse Counterpart of the Novel Polypeptide (Precursor Polypeptide)

The full-length cDNA encoding the mouse counterpart of the novel polypeptide was acquired by performing the PCR described below.

First, there was prepared a 50 μl mixture containing 5 pmols each of the oligo DNA (UP (SEQ ID NO:36)) chemically synthesized based on the base sequence of the 5' side untranslational region of the novel polypeptide mouse counterpart gene obtained in EXAMPLE 5 as a sense strand primer and the oligo DNA (ML (SEQ ID NO:38)) chemically synthesized based on the mouse cDNA partial sequences obtained in EXAMPLE 5 as an antisense strand primer, 5 μl of 100 mM Tris-hydrochloride buffer (pH 8.3), 5 μl of 500 mM potassium chloride solution, 3 μl of 25 mM magnesium chloride solution, 4 μl of 2.5 mM deoxyribonucleotide solution, 4 μl of Marathon™-Ready cDNA Mouse Testis (Clontech) as a template DNA, and 0.5 μl of TaKaRa Taq™ (Takara Shuzo Co., Ltd.). Next, the reaction mixture was subjected to the following reaction using TaKaRa PCR Thermal Cycler MP (Takara Shuzo Co., Ltd.) to first maintain at 95° C. for 1 minute, then repeat the reaction cycle set to include 95° C. for 30 seconds, 67° C. for 1 minute and 72° C. for 1 minute 40 times, and then react at 72° C. for further 10 minutes. After completion of the reaction, the reaction solution was electrophoresed on 1.0% agarose gel and stained with ethidium bromide, whereby the band corresponding to the DNA amplified by the PCR was confirmed at the position around 0.45 kb as converted by a molecular marker. Next, the DNA fragment was recovered using GENE CLEAN SPIN KIT (BIO101, Inc.) and subjected to TA cloning using pCR (registered trademark) 2.1-TOPO (Invitrogen, Inc.) to determine the base sequence, and the plasmid was introduced into competent cells (Invitrogen) of *E. coli* TOP10 strain. A clone bearing the foreign DNA fragment-inserted plasmid was selected from the colonies of ampicillin-resistant transformants appeared on ampicillin-containing LB agar plate medium. The plasmid DNA, pVHUPTm was prepared from the clone and the base sequence of the inserted DNA was determined.

The results revealed that pVHUPTm contained the DNA fragment of 475 base pairs shown by SEQ ID NO:40 containing the open reading frame (ORF) composed of 423 bases shown by SEQ ID NO:24, encoding the mouse counterpart of the novel polypeptide precursor composed of 141 amino acids shown by SEQ ID NO:23.

The thus acquired plasmid pVHUPTm bearing the DNA encoding the mouse novel polypeptide (precursor polypeptide) was transfected to *Escherichia coli* TOP10 to give *Escherichia coli* TOP10/pVHUPTm.

Example 8

Analysis of Chromosomal Gene Encoding the Porcine Counterpart of the Novel Polypeptide (Precursor Polypeptide)

The DNA fragment encoding a part of the porcine novel polypeptide (precursor polypeptide) was acquired by performing the PCR described below. That is, there was prepared a 40 μl mixture containing 20 pmols each of the oligo DNA shown by SEQ ID NO:53 (ex1F1) as a sense strand primer and the oligo DNA shown by SEQ ID NO:54 (ex1R1) as an antisense strand primer, further containing 20 μl of Premix Taq™ (Ex Taq™ Version) (Takara Shuzo Co., Ltd.) and 1 μl of porcine genomic DNA (Clontech, #6651-1) as a template DNA. Using a thermal cycler (GeneAmp™ PCR system model 9700 (PE Biosystems)), PCR was carried out by the program set to first maintain at 94° C. for 2 minutes, then repeat the reaction cycle set to include 94° C. for 10 seconds, 55° C. for 10 seconds and 72° C. for 30 seconds 30 times, and then extend at 72° C. for 1 minute and 30 seconds. After completion of the reaction, the reaction solution was electrophoresed on 2.0% agarose gel and stained with ethidium bromide, whereby the DNA amplified by the PCR was confirmed as a single band. The DNA fragment was recovered using QIAquick Gel Extraction Kit (Qiagen) and subjected to TA cloning using pCRTM 2.1-TOPO (Invitrogen, Inc.) to determine the base sequence. The plasmid was introduced into competent cells (Toyobo Co., Ltd.) of *E. coli* DH5α strain. A clone bearing the foreign DNA fragment-inserted plasmid was selected from the colonies of ampicillin-resistant transformants appeared on ampicillin-containing LB agar medium. In order to determine the base sequence of the inserted DNA, using as a template DNA the plasmid prepared from the cloned cells reincubated in the presence of ampicillin and commercially available DNAs (PRM-007, PRM-008 (Toyobo Co., Ltd.)) as sequencing primers, sequencing was performed on a thermal cycler (GeneAmp™ PCR system model 9700 (PE Biosystems)) using API PRISM BigDye Terminator Cycle Sequencing FS Ready Reaction Kit (PE Biosystems) similarly under the conditions given in the brochure attached. Then, the reaction sample was analyzed by DNA Sequencer ABI PRISM 377 (PE Biosystems).

The results revealed that the PCR product was the DNA fragment having the primer sequences described above at the both ends and containing therebetween the DNA of 239 base pairs shown by SEQ ID NO:56, containing the base sequence shown by SEQ ID NO:55 encoding from the N terminus of the porcine type precursor protein to the B chain peptide via the signal peptide. Next, in order to analyze the structure in the downstream (3') side, genome walking was carried out. GenomeWalker library DNA processed for the porcine genomic DNA described above with Universal GenomeWalker™ Kit (Clontech) was used as a test sample, and the test sample was treated by a method modified from that used for Rat GenomeWalker™ Kit and Mouse GenomeWalker Kit (Clontech). First, for gene specific primers, 2 oligo DNAs (POReX1F1 (SEQ ID NO:57), POReX1F2 (SEQ ID NO:58)) corresponding to a part of the base sequence shown by SEQ ID NO:56 were chemically synthesized, respectively. POReX1F1 was used for the first PCR and POReX1F2 for the nested PCR. In the amplified DNA fragment obtained after the nested PCR, the base sequence was determined by a modification from the method supra. Starting from the POReX1F2 primer sequence site, the base sequence was analyzed while comparing homology to the base sequences of cDNAs encoding mouse and rat precursor proteins. As a result, the primary structure was clarified, which then revealed that the porcine counterpart of the novel polypeptide (precursor polypeptide) was a polypeptide composed of 140 amino acid residues shown by SEQ ID NO:45 encoded by the DNA of 420 bases shown by SEQ ID NO:46; the gene was composed of two exons intervened by one intervening sequence on porcine chromosome and in the 420 bases, 193 bases shown by SEQ ID NO:59 and 227 bases shown by SEQ ID NO:60 are encoded by the first exon and the second exon, respectively. The polypeptide contained sequences characteristic of the insulin/IGF/relaxin family as in the human novel polypeptide (precursor polypeptide), i.e., the signal sequence as well as the A chain (SEQ ID NO:47) and B chain (SEQ ID NO:49) inserted between basic amino acids and having Cys residues. The porcine novel polypeptide had 77.1%, 70.0% and 67.1% homology to the mouse precursor protein and the rat novel precursor protein, respectively, on an amino acid level.

Example 9

Cloning of the Full-length cDNA Encoding a Variant of the Rat Mesenteric Adipose Tissue-Derived Novel Polypeptide (Precursor Polypeptide)

The full-length cDNA encoding a variant of the rat mesenteric adipose tissue-derived novel polypeptide (precursor polypeptide) was acquired by the following PCR.

First, there was prepared a 50 μl mixture containing 5 pmols each of UP (SEQ ID NO:36) as a sense strand primer and RL (SEQ ID NO:37) as an antisense strand primer in the oligo DNAs used in EXAMPLE 6, 5 μl of 100 mM Tris-hydrochloride buffer (pH 8.3), 5 μl of 500 mM potassium chloride solution, 3 μl of 25 mM magnesium chloride solution, 4 μl of 2.5 mM deoxyribonucleotide solution, 1 μl of a cDNA solution prepared from rat mesenteric adipose tissue-derived total RNA as a template DNA, and 0.5 μl of TaKaRa Taq™ (Takara Shuzo Co., Ltd.). Next, using TaKaRa PCR Thermal Cycler MP (Takara Shuzo Co., Ltd.), PCR was carried out on the program designed to first maintain at 95° C. for 1 minute, then repeat the reaction cycle set to include 95° C. for 30 seconds, 67° C. for 1 minute and 72° C. for 1 minute 35 times, and then react at 72° C. for further 10 minutes. After completion of the reaction, the reaction solution was electrophoresed on 1.0% agarose gel and stained with ethidium bromide, whereby the band corresponding to the DNA amplified by the PCR was detected at the position around 0.6 kb as converted by a molecular marker. Next, the DNA fragment was recovered using GENE CLEAN SPIN KIT (BIO101, Inc.) and subjected to TA cloning using pCR™ 2.1-TOPO (Invitrogen, Inc.) to determine the base sequence, and the plasmid was introduced into competent cells of *E. coli* TOP10 strain. A clone bearing the foreign DNA fragment-inserted plasmid was selected from the colonies of ampicillin-resistant transformants appeared on ampicillin-containing LB agar medium. The plasmid DNA, pVHABDr was prepared. In order to determine the base sequence of the inserted DNA, using pVHABDr as a template and commercially available DNAs (PRM-007, PRM-008 (Toyobo Co., Ltd.)) as sequencing primers, sequencing was performed on a thermal cycler (GeneAmp™ PCR system model 9700 (PE Biosystems)) using API PRISM™ BigDye Terminator Cycle Sequencing FS Ready Reaction Kit (PE Biosystems) under the conditions given in the brochure attached. Then, the reaction sample was analyzed by DNA Sequencer ABI PRISM 377 (PE Biosystems).

The results revealed that the DNA fragment of 572 base pairs shown by SEQ ID NO:61 containing the open reading frame (ORF) encoding the novel polypeptide (precursor polypeptide) variant composed of 174 amino acid residues shown by SEQ ID NO:51 encoded by the DNA of 522 bases shown by SEQ ID NO:52 was inserted in pVHABDr. The polypeptide variant contained sequences characteristic of the insulin/IGF/relaxin family, i.e., completely the same signal sequence as that of the rat counterpart of the novel polypeptide (precursor polypeptide) described in EXAMPLES 5 and 6, as well as the A chain (SEQ ID NO:19) and B chain (SEQ ID NO:21) inserted between basic amino acids and having Cys residues, and had a structure inserted with the polypeptide composed of 34 amino acid residues shown by SEQ ID NO:63 encoded by the DNA of 102 bases shown by SEQ ID NO:62 derived from a part of one intervening sequence located between the first and second exons of the novel polypeptide (precursor polypeptide) rat counterpart described in EXAMPLE 5.

The thus acquired plasmid pVHABDr was transfected to *Escherichia coli* TOP10 to give *Escherichia coli* TOP10/pVHABDr.

Example 10

Production of Human Novel Polypeptide Gene-Expressing AtT20 Cell Line

The plasmid pVHNC5Lh obtained in EXAMPLE 3, inserted with the DNA fragment encoding the novel polypeptide, was digested with restriction enzyme Eco RI. After completion of the reaction, the reaction solution was electrophoresed on 1.5% agarose gel to recover 2 bands corresponding to 0.15 kb and 0.35 kb from the gel. Mammalian cell expression vector pcDNA 3.1 (−) (Invitrogen) was digested with Eco RI followed by dephosphorylation with Calf intestine alkaline phosphatase (Takara Shuzo Co., Ltd.). After completion of the reaction, the reaction solution was electrophoresed on 1.5% agarose gel to recover a band corresponding to about 5.5 kb from the gel. After ligating these DNA fragments using DNA Ligation Kit ver. 2 (Takara Shuzo Co., Ltd.), the reaction solution was added to *E. coli* JM109 Competent Cells (Takara Shuzo Co., Ltd.) for transfection. From the resulting ampicillin-resistant colonies, there was selected a clone bearing the plasmid inserted with total 0.5 kb DNA fragments of 0.15 kb Eco RI fragment at the CMV promoter side of the vector insertion side and 0.35 kb Eco RI fragment at the poly A signal side. The plasmid was prepared in large quantities from the reincubated cells, using Plasmid Maxi Kit (QIAGEN).

Using Lipofection (GIBCO-BRL), the plasmid thus obtained was transfected to mouse pituitary tumor cell line AtT20 (Dainippon Pharmaceutical Co., Ltd.) in accordance with the method described in the protocol attached. Human novel polypeptide gene-expressing AtT20 cell line was acquired by selecting the colony capable of growing in DMEM containing 10% FCS, penicillin (100 units/ml), streptomycin (100 μg/ml) and 500 μg/ml of G418 (Wako Pure Chemical Industries, Ltd.).

Example 11

Production of Immunogen Bearing the Novel Polypeptide (Human Type) a Chain N-terminal Peptide A complex of the A chain N-terminal peptide of the novel polypeptide (human type) obtained in EXAMPLE 3 supra, AspValLeuAlaGlyLeuSerSerSerCys (N-terminal (1–10) partial sequence of SEQ ID NO:7; synthesized by a modification of publicly known methods) and hemocyanin (KLH) was prepared and used as an immunogen. That is, 20 mg of KLH was dissolved in 2.0 ml of 0.1 M phosphate buffer (pH 6.7). The solution was mixed with 200 μl of DMSO solution containing 2.8 mg of N-(γ-maleimidobutyryloxy)succinimide (GMBS) and the mixture was reacted at room temperature for 30 minutes. After an excess of GMBS reagent was removed through Sephadex G-25 column equilibrated with 0.1 M phosphate buffer (pH 6.5) containing 2 mM EDTA, 5 mg of maleimide-introduced KLH was mixed with 0.84 mg of the A chain N-terminal peptide dissolved in 0.1 ml of DMSO. The mixture was reacted at 4° C. overnight. After completion of the reaction, the mixture was dialyzed to physiological saline at 4° C. for 2 days.

BALB/C female mice of 8 weeks old were subcutaneously injected for immunization with about 0.1 mg/mouse of the A chain N-terminal peptide-KLH complex, together with complete Freund's adjuvant. After 3 weeks, the same dose of immunogen was boostered together with incomplete Freund's adjuvant and blood was collected a week later.

Example 12

Production of Horseradish Peroxidase (HRP)-labeled a Chain N-Terminal Peptide

The A chain N-terminal peptide supra was crosslinked with HRP (for enzyme immunoassay, manufactured by Boehringer Mannheim), which was used as a labeled peptide for enzyme immunoassay (EIA). That is, 23 mg of HRP was dissolved in 2.3 ml of 0.1 M phosphate buffer, pH 6.7. The solution was mixed with 0.23 ml of DMF solution containing 1.6 mg of GMBS. After reacting at 30 minutes at room temperature, the reaction mixture was fractionated through Sephadex G-25 column equilibrated with 0.1 M phosphate buffer, pH 6.5, containing 2 mM EDTA. After 2.3 mg of the thus produced maleimide-introduced HRP was mixed with 1 ml of the A chain N-terminal peptide, the mixture was reacted at 4° C. for a day. After completion of the reaction, the mixture was fractionated through Ultrogel AcA54 (manufactured by Pharmacia) column equilibrated with 0.1 M phosphate buffer, pH 6.5 to give the HRP-labeled A chain N-terminal peptide.

Example 13

Determination of Antibody Titer in the Antisera of Mouse Immunized with the a Chain N-terminal Peptide The antibody titer in mouse antisera was assayed by the following method. In order to prepare an anti-mouse immunoglobulin antibody-bound microplate, a 0.1 M carbonate buffer solution, pH 9.6, containing 0.1 mg/ml of goat anti-mouse immunoglobulin antibody (IgG fraction, manufactured by Cappel) was first dispensed onto a 96-well microplate by a 0.1 ml portion, which was allowed to stand at 4° C. for 24 hours. Next, the plate was rinsed with phosphate buffered saline (PBS, pH 7.4), and to block the excessive binding sites, 0.3 ml each of PBS, pH 7.2, containing 25% Block Ace (manufactured by Snow Brand Milk Products Co., Ltd.) and 0.05% $NaN_3$ was added to treat at 4° C. for at least 24 hours.

To each well of the mouse immunoglobulin antibody-bound microplate, 0.14 ml of mouse antiserum diluted with buffer EC [0.02 M phosphate buffer, pH 7.0, containing 0.2% BSA, 0.4 M NaCl, 0.4% Block Ace, 0.05% CHAPS [3-[(3-cholamidopropyl)dimethylammonio]-1-propanesulfonate; Boehringer Mannheim], 2 mM EDTA and 0.05% $NaN_3$] was added, and the mixture was reacted at 4° C. for 16 hours. Next, after the plate was rinsed with PBS, pH 7.4, 0.1 ml of a 100-fold dilution of the HRP-labeled A chain N-terminal peptide prepared in EXAMPLE 12 supra with buffer C [0.02 M phosphate buffer, pH 7.0, containing 1% BSA, 0.4 M NaCl and 2 mM EDTA]. The mixture was reacted at 4° C. for a day. Next, after the plate was rinsed with PBS, pH 7.4, 0.1 ml of TMB microwell peroxidase substrate system (KIRKEGAARD & PERRY LAB., dealt through Funakoshi Pharmaceutical Co., Ltd.) was added and the mixture was reacted at room temperature for 5 minutes to assay the enzyme activity on the solid phase. After 0.1 ml of 1 M phosphoric acid was added to terminate the reaction, the absorbance at 450 nm (Abs. 450) was measured by a plate reader (MTP-120 manufactured by Corona Co., or Multiskan Ascent manufactured by Labsystems). The results are shown in FIG. 4. An increase of the antibody titer to the A chain N-terminal peptide was noted in all of the immunized 8 mice.

Example 14

Production of Anti-A Chain N-terminal Peptide Monoclonal Antibody

Mouse Nos. 1 and 7, which showed a relatively high antibody titer in EXAMPLE 13, received final immunization by intravenously administering the A chain N-terminal peptide-KLH in a dose of 0.08 to 0.1 mg when calculated as KLH. Three days after the final immunization, the spleen was withdrawn from mice and subjected to compression filtration through a stainless mesh to suspend in Eagle's Minimum Essential Medium (MEM). Thus, the spleen cell suspension was obtained. BALB/C mouse-derived myeloma cells P3-X63. Ag 8. U1 (P3U1) were used as cells for cell fusion [Current Topics in Microbiology & Immunology, 81, 1 (1978)]. The cell fusion was carried out by a modification from the original method [Nature, 256, 495 (1975)]. That is, the spleen cells and p3U1 were rinsed 3 times with serum-free MEM, respectively, and mixed to be 6.6:1 in a ratio of the spleen cells to P3U1 count. The cells were deposited by centrifugation at 750 rpm for 15 minutes. After the supernatant was thoroughly removed, the sediment was gently loosened and 0.3 ml of 45% polyethylene glycol (PEG) 6000 (Kochlight). The mixture was allowed to stand for 7 minutes in a warm water bath of 37° C. for fusion. After the fusion, MEM was gradually added to the cells to 15 ml in total of MEM, followed by centrifugation at 750 rpm for 15 minutes. The supernatant was then removed. The cell sediment was suspended in GIT medium (Wako Pure Chemical Industries, Ltd.) containing 10% fetal calf serum (GIT-10% FCS)

in 2×10 P3U1/ml. The suspension was plated in 169 wells of a 24-well multi-dish (manufactured by Linbro) by 1 ml each/well. After plating, the cells were incubated in a 5% carbon dioxide gas incubator at 37° C. After 24 hours, HAT selective culture was initiated by adding GIT-10% FCS medium (HAT medium) containing HAT ($1\times10^{4}$ M hypoxanthine, $4\times10^{-7}$ M aminopterin and $1.6\times10^{-3}$ M thymidine) by 1 ml each/well. After discarding 1 ml of old medium 5 and 8 days after the initiation of the culture, 1 ml of HAT medium was added to continue the HAT selective culture. On Day 9 after the cell fusion, the supernatant was collected.

The antibody titer in the culture supernatant was assayed by a modification of the method described in EXAMPLE 13. That is, 0.07 ml of the culture supernatant and 0.07 ml of Buffer EC were added to each well of the anti-mouse immunoglobulin antibody-bound microplate. After reacting at 4° C. overnight, 0.1 ml of the HRP-labeled A chain N-terminal peptide diluted to 100o-fold with the buffer C was reacted at room temperature for 7 hours in the presence of absence of 0.002 mM non-labeled A chain N-terminal peptide. After the plate was rinsed with PBS, the enzyme activity on the solid phase was assayed by the method described in EXAMPLE 13. As a result, 31 wells, on which a specific antibody titer was recognized, were selected from the 168 wells, and the hybridomas were freeze-stored. Furthermore, hybridoma Nos. 14, 43, 144, 146 and 149 in 5 wells were cloned by the dilution method. In cloning, BALB/C mouse thymocytes were added as feeder cells in $5\times10^{5}$/well. After cloning, the antibody titer in the culture supernatant was assayed in a similar manner. Positive clones were detected from No. 14 in 2 out or 33 wells, in 1 out of 28 wells from No. 43, in 23 out of 25 wells from No. 144, in 15 out of 58 wells from No. 149, and in 7 out of 288 wells from No. 146.

From these clones, No. 144-10 (hybridoma HK4-144-10) was selected as an anti-A chain N-terminal peptide monoclonal antibody-producing hybridoma.

Example 15

Mouse Ascites Formation of Hybridoma and Purification of Monoclonal Antibody

Mouse ascites was formed using hybridoma No. 144-10. The hybridoma supra was intraperitoneally administered in a dose of 1 to $3\times10^{6}$ cells/mouse to mice (BALB/C, female) previously given 0.5 ml of mineral oil intraperitoneally. After 6 to 20 days, antibody-containing ascites was collected. The monoclonal antibody was purified from the collected ascites through protein-A column. That is, after about 25 ml of ascites was diluted with the equal volume of binding buffer (1.5 M glycine, pH 9.0, containing 3.5 M NaCl and 0.05% $NaN_3$), the dilution was passed through recombinant protein-A agarose (manufactured by Repligen) previously equilibrated with the binding buffer, and the specific antibody was eluted with an elution buffer (0.1 M citrate buffer, pH 3.0, containing 0.05% $NaN_3$). The eluate was dialyzed to PBS, pH 7.4, at 4° C. for 2 days, and then subjected to cell-free filtration through a 0.22 μm filter (manufactured by Millipore) and stored at 4° C. or −80° C. The thus obtained monoclonal antibody was named HK4-144-10.

Example 16

Purification of the Novel Polypeptide (Human Type) from the AtT20 Culture Supernatant The novel polypeptide (human type) precursor-expressing AtT20 described in EXAMPLE 10 was incubated in 10% FCS-containing DMEM medium or 5% FCS-containing OPTI-MEM medium supplemented with 0.5 mg/ml of G418. The culture supernatant of 2 liters was passed through 3.2 ml of HK4-144-10-bound Tresyl Toyopearl solid phase and then rinsed wit PBS, pH 7.4, followed by elution with 10 ml of 0.1% TFA (trifluoroacetic acid)-containing 60% acetonitrile. The HK4-144-10-bound Tresyl Toyopearl solid phase was prepared by binding 125 mg of the HK4-144-10 antibody to 5 g of AF-Tresyl Toyopearl (manufactured by TOSO) in accordance with the instructions attached. The eluate was lyophilized and dissolved in 0.5 ml of 0.1% TFA-containing 40% acetonitrile. The solution was fractionated by gel filtration using TSK G3000 PW column (7.8×300 mm, manufactured by TOSO) equilibrated with 0.1% TFA-containing 40% acetonitrile. The flow rate was set at 0.25 ml/min and 2 minute-elution was collected as 1 fraction.

The immunological activity of each fraction was examined by the competitive EIA, using the monoclonal antibody HK4-144-10 described in EXAMPLE 15 above and the HRP-labeled A chain N-terminal peptide described in EXAMPLE 12. That is, 0.05 ml of HK4-144-10 diluted to 3 ng/ml with 0.05% CHAPS-containing buffer C (buffer CC), 0.05 ml of the A chain N-terminal peptide serially diluted (0, 0.016, 0.08, 0.4, 2 and 10 ng/ml) with the buffer CC or the above gel filtration fraction diluted to 250-fold with the buffer CC, and 0.05 ml of the HRP-labeled A chain N-terminal peptide (6000-fold dilution with the buffer CC) were added to the anti-mouse immunoglobulin antibody-bound microplate. The mixture was reacted at 4° C. for a day. After the reaction, the mixture was rinsed with PBS, pH 7.4, and the enzyme activity on the solid phase was assayed by the method described in EXAMPLE 13 above. As a result, about 1.8 nmol of the immunological activity of the novel polypeptide (human type), as calculated from the standard curve for the A chain N-terminal peptide, was detected in the fraction No. 19–21.

By similar procedures, about 0.8 nmol of the immunological activity of the novel polypeptide (human type) was detected in the fraction No. 19–21, from 1 liter of the other culture supernatant of the novel polypeptide precursor (human type)-expressing AtT20.

Next, the novel polypeptide (human type) (about 2.6 nmols as the immunological activity) partially purified from 3 liters in total of the culture supernatant was fractionated through TSK ODS-80TS column (4.6×250 mm, TOSOH). The concentration of acetonitrile as an eluent was in a linear gradient of 17% to 38% (containing 0.05% TFA), which was increased over 40 minutes. The eluate for 0.5 minute at a flow rate of 1 ml/min was collected as 1 fraction, the UV peaks were determined by absorbance at 215 nm, and the immunological activity was assayed by the competitive EIA supra. The results are shown in FIG. 5. Major UV peak Nos. 1, 2 and 3 coincided with immunologically active fraction Nos. 56, 64 and 65, respectively. These fractions were applied to mass spectrometry (LCQduo, manufactured by ThermoQuest, Inc.) and amino acid sequencing (491cLC, manufactured by Biosystems, Inc.). The results showed the molecular weight of 2459.9 based on the mass spectrometry of fraction No. 56 and the A chain N-terminal peptide, AspValLeuAlaGlyLeuSerSerSer (N-terminal (1–10) partial sequence of SEQ ID NO:7) based on the amino acid sequencing. Since this molecular weight is smaller than the molecular weight of 2463.8 in the reduced A chain, it was found that the oxidized A chain was eluted solely in fraction No. 56. Turning to the mass spectrometry of fraction No. 4, the molecular weight of 5500.5 was obtained, and a mixed sequence of the B chain N-terminal sequence, ArgAlaAla- ProTyrGlyValArgLeu (N-terminal (1–9) partial sequence of SEQ ID NO:8) and the A chain N-terminal sequence, AspValLeuAlaGlyLeuSerSerSer (N-terminal (1–9) partial sequence of SEQ ID NO:7) based on the amino acid sequencing, was obtained based on the amino acid sequencing. Since this molecular weight was almost coincident with the molecular weight 5500.4 of the novel polypeptide (human type) composed of A chain having the amino acid sequence shown by SEQ ID NO:7 and B chain having the amino acid sequence shown by SEQ ID NO:8, it was found that the novel polypeptide (human type) itself was eluted in fraction No. 64. Further in the mass spectrometry of fraction No. 65, at least 2 components were detected, wherein the molecular weight of the main component was 5343.7 and that of the accessory component was 5272.8. The molecular weights of the novel polypeptide (human type) B chain devoid of the N-terminal Arg and further devoid of Ala are 5344.2 and 5273.1, respectively, and almost coincide with the molecular weights found. It was thus supposed that the main component would be the B chain devoid of the N-terminal amino acid Arg and the accessory component would be additionally devoid of Ala.

From the foregoing results, it was verified that the novel polypeptide composed of the A chain having the amino acid sequence shown by SEQ ID NO:7 and the B chain having the amino acid sequence shown by SEQ ID NO:8 was actually secreted/produced in the AtT20 cells. It was also revealed that the oxidized A chain was secreted/produced solely.

Example 17

Intracellular Cyclic Adenosine-1-phosphate (cAMP) Production-promoting Activity of the Purified Human Novel Polypeptide Preparation on Human Monocyte Cell Line THP-1 Cells (Dainippon Pharmaceutical Co., Ltd.)

A fraction containing the novel polypeptide (human type), which was separately purified from 3.5 liters of the culture supernatant with another lot of the novel polypeptide precursor (human type)-expressing AtT20 cells by the method described in EXAMPLE 16 supra, was lyophilized, and 200 μl of the buffer A (PBS, 1% BSA, 0.05% CHAPS) was added to dissolve the lyophilized fraction (concentration of 3.8 μM). The solution was used as the purified human novel polypeptide preparation in the following experiment. Human monocyte cell line THP-I cells were suspended in medium A (DMEM/F12 (1:1), 10 mM HEPES (pH 7.5), 0.1% BSA, 0.1 mM 3-isobutyl-1-methylxanthine (IBMX)) in 106 cells/ml, and 200 μl each of the cell suspension was dispensed in a microtube of 1.5 ml volume, followed by preincubation at 37° C. for an hour. Furthermore, 25 μl each of the purified human novel polypeptide preparation, which was diluted with the buffer A to $10^2$, $10^3$, $10^4$, $10^5$, $10^6$, $10^7$ and $10^8$ in terms of the dilution multiples per the reaction solution, was added to the cell suspension described above, and 25 μl each of a solution (final concentration of 1 μM) of forskolin (Wako Pure Chemical Industries, Ltd.) in the medium A was further added to the cell suspension supra, followed by incubation at 37° C. for 30 minutes. The cells were deposited by centrifugation at 3,000 rpm for 5 minutes at 4° C. After the supernatant was discarded, 1 ml of medium A was added to suspend the cells. After centrifugation (3,000 rpm, 5 minutes, 4° C.), the supernatant was discarded and the cells were suspended in 250 μl of medium A. After 50 μl of 20% perchloric acid solution was added to the suspension, the mixture was allowed to stand at 4° C. for 20 minutes. After centrifugation (15,000 rpm, 10 minutes, 4° C.), 250 μl of the supernatant was transferred to a separate microtube of 1.5 ml volume, 60 mM HEPES and 1.5 M KOH solution were added for neutralization, which was used as a sample for the cAMP assay.

Using cAMP EIA system (Amersham Pharmacia), the level of the intracellular cAMP was assayed by a modification of the protocol attached to the kit.

As a result, the purified human novel polypeptide preparation showed the activity of increasing the level of intracellular cAMP produced against the THP-1 cells dependently on the concentration (FIG. 6).

Example 18

Analysis of the Cell Stimulating Activity of the Purified Human Novel Polypeptide Preparation on the THP-1 Cell Line by a Microphysiometer The cell stimulating activity of the purified human novel polypeptide preparation on the THP-1 cell line was examined by determining an extracellular acidification rate using a microphysiometer as described below. First, confluent THP-1 cells, which had previously been subjected to suspension culture in 10% FCS-containing RPMI 1640 medium, were suspended in an assay medium (low buffered RPMI (Molecular Devices, Ltd.)) in $1\times10^8$ cells/ml. Furthermore, 7 μl each of a 3:1 mixture of the suspension and agarose cell entrap medium (Molecular Devices, Ltd.) was dispensed onto the center of each capsule cup (Molecular Devices, Ltd.). After solidification, agarose was immersed in the assay medium and in this state, a spacer and a capsule insert were sequentially put on the cup. Finally, the insert was fully immersed by the assay medium to complete the assay capsule. The capsule was immediately transferred to a sensor chamber and mounted to the body of Cytosensor™ Microphysiometer (Molecular Devices, Ltd.). Measurement of the acidification rate in the chamber and data analysis were performed by the application program Cytosoft attached to the device. A pump speed was set to have a flow rate of 100 μl/min in the assay medium during pump running, and the acidification rate was measured every interval of 40 seconds in each pump cycle of 2 minutes and 30 seconds. As a test sample, there was used a 500-fold dilution of the purified human novel polypeptide preparation obtained in EXAMPLE 16, which was obtained by dissolving in the buffer A (PBS, 1% BSA, 0.05% CHAPS) described in EXAMPLE 17, and diluting the solution with the assay medium. The dilution was set in one of 2 flow paths of the cytosensor. The human novel polypeptide solution was exposed to the cells for a given time (7 minutes) by changing bulbs. The change for the acidification rate is compared by converting the acidification rate at each time into percentage based on a rate prior to exposing the cells. As a result, showing in FIG. 9, transient increase of a rate in accompanies with the exposure of human novel polypeptide purified preparation. The cell stimulating activity of the peptide was thus detected.

Example 19

Preparation of the Human Novel Polypeptide Fused Protein-Expressing Recombinant *E. coli* Strain Using as a template pVHNC5Lh, which was the plasmid containing the DNA fragment encoding the human novel polypeptide obtained in EXAMPLE 3, the oligo DNA (CCGGATCCATGCGGGCAGCGCCTTA) shown by SEQ ID NO: 64 as a sense strand primer and the oligo DNA (ATCTCGACTGCCCCGAAGAACC) shown by SEQ ID NO:65 as an antisense strand primer, as well as the oligo DNA (CAGTCGAATGGATGTCCTGGCTGGC) shown by SEQ ID NO:66 as a sense strand primer and the oligo DNA (CCGGATCCTAGCAAAGGCTACTGATTTCA) shown by SEQ ID NO:67 as an antisense strand primer, PCR was carried out, respectively, using LA-Taq polymerase (Takara Shuzo Co., Ltd.). After completion of the reaction, the reaction solution was electrophoresed on 1.5% agarose gel, and the DNA fragments of 0.3 kb and 0.1 kb produced by the respective reactions were recovered from the gel. These DNA fragments were digested with restriction enzymes BamHI and TaqI thereby to form the terminal BamHI and the TaqI sites. pET-11a (STRATAGENE) expression vector was digested with BamHI and dephosphorylated using Calf intestine phosphatase (Takara Shuzo Co., Ltd.). After completion of the reaction, the reaction solution was electrophoresed on 1% agarose gel, and the DNA fragment of 5.5 kb was recovered from the gel. After these 3 DNA fragments were ligated using DNA Ligation Kit ver. 2 (Takara Shuzo Co., Ltd.), the reaction solution was added to *E. coli* JM109 Competent Cells (Takara Shuzo Co., Ltd.) for transfection. From the ampicillin-resistant colonies obtained, the clone bearing the plasmid (pETVHMMh) inserted with the 0.4 kb DNA fragment serially connected with the 0.1 kb fragment and the 0.3 kb fragment described above was selected. The construction map of the plasmid is shown in FIG. 7.

After the base sequence of the inserted DNA fragment was confirmed, the plasmid was transfected to Epicurian Coli BL21-Gold (DE3) Competent Cells (STRATAGENE) to give recombinant *Escherichia coli* BL21-Gold (DE3)/pETVHMMh for the expression of human novel polypeptide fused protein. The fused protein is encoded by the total 399 base sequence shown by SEQ ID NO:68 and composed of 133 amino acid residues shown by SEQ ID NO:69, which is ligated in the order of the leader peptide sequence composed of 14 amino acids-Met-B chain-processing protease recognition sequence (Arg-Trp-Arg-Arg)-C chain-Met-A chain.

Example 20

Expression of Fused Protein by the Human Novel Polypeptide Fused Protein Expressing Recombinant *E. coli* Strain After *Escherichia coli* BL21-Gold (DE3)/pETVHMMh obtained in EXAMPLE 19 was cultured in LB medium supplemented with 50 μg/ml of ampicillin at 37° C. to reach 0.5 of OD600, isopropyl-β-D-thiogalactopyranoside (IPTG) was added in a final concentration of 1 mM, followed by incubation for further 3 hours. After completion of the incubation, the cells were collected by centrifugation and proteins were extracted from all the cells for analysis by SDS-PAGE.

As shown in FIG. 8, the band of 17 KDa protein corresponding to the human novel polypeptide fused protein was observed under the IPTG induction. The fused protein was recovered as inclusion bodies from the *E. coli* cells incubated based on this EXAMPLE. After the S—S bonds were formed in a correct combination by denaturation and unwinding, the C terminal side of the Met residue is chemically cleaved by cyanogen bromide (CNBr), and limited degradation of the Arg-Trp-Arg-Arg sequence at the C terminus and breakage of the resulting two Arg residues are made through enzymatic reactions so that the mature human novel polypeptide can be obtained.

Example 21

Preparation of the Human Novel Polypeptide and its Derivative from the Human Novel Polypeptide Fused Protein Expressing Recombinant *E. coli* Strain The cells obtained by culturing *Escherichia coli* BL21-Gold (DE3)/pETVHMMh obtained in EXAMPLE 19 by the method described in EXAMPLE 20 were suspended for disruption buffer (50 nM Tris-HCl (pH 6.8), 5 mM EDTA) and subjected to ultrasonication treatment (1 min.×3 times), followed by centrifugation (15,000 rpm, 20 minutes, 4° C.). The sediment was suspended in wash buffer (50 mM Tris-HCl (pH 6.8), 5 mM EDTA, 4% Triton X-100), and the suspension was centrifuged (15,000 rpm, 20 minutes, 4° C.). Then, the sediment was resuspended in the wash buffer, followed by centrifugation in a similar manner. The sediment was suspended in distilled water and the centrifugal operation was likewise repeated twice. The thus obtained sediment, i.e., the inclusion body containing the human novel polypeptide fused protein was dissolved in solubilizing buffer (50 mM Tris-HCl (pH 6.8), 4 M guanidine hydrochloride, 5 mM 2-mercaptoethanol). After the solubilized solution was diluted to 20-fold in reproduction buffer (50 mM Tris-HCl (pH 6.8), 5 mM EDTA, S mM reduced glutathione, 0.5 mM oxidized glutathione, 0.8 M arginine hydrochloride), followed by agitation at 4° C. overnight. After the solution was centrifuged (15,000 rpm, 20 minutes, 4° C.) and the resulting supernatant was concentrated using Sep-Pak C-18 (Waters, Inc.), the concentrate was lyophilized. Using TSKgel ODS-80Ts column, the main peak fraction was fractionated from the lyophilized product containing the human novel polypeptide fused protein by a modification of the method described in EXAMPLE 16. As a result of the mass spectrometry performed by a modification of the method described in EXAMPLE 16, the value found on the molecular weight coincided with the calculated molecular weight of the polypeptide (2–133) devoid of one amino acid (Met) at the N terminus of the polypeptide composed of 133 amino acids shown by SEQ ID NO:69 (mass spectrometry: Found: 14156.9, Calcd.: 14157.0).

Next, the polypeptide (2–133) described above was incubated overnight at room temperature in the presence of 0.1 N hydrochloride and 5% cyanogens bromide (CNBr) to chemically degrade the polypeptide. The degradation product was fractionated by a modification of the method described in EXAMPLE 16, using TSKgel ODS-80Ts column, and the fraction of the main degradation product was subjected to mass spectrometry by a modification of the method described in EXAMPLE 16. Thus, the found molecular weight coincided with the calculated molecular weight of the polypeptide ((16–53)/(110–133)) composed of the peptide added with 11 amino acids (ArgArg-SerAspIleLeuAlaHisGluAlaHse) at the C terminus of the B chain having the amino acid sequence shown by SEQ ID NO:8 and the A chain having the amino acid sequence shown by SEQ ID NO:7 (mass spectrometry: Found: 6732.9, Calcd.: 6732.8).

Using the polypeptide (16–53)/(110–133) supra as substrate, the reaction product obtained after incubation in the reaction solution containing 0.1 M Tris-HCl (pH 8.5) at 37° C. for 45 minutes in the presence of trypsin (Boehringer Mannheim) and carboxypeptidase B (CPB) (Boehringer Mannheim) (enzyme/substrate (weight ratio)=1/1000, respectively), was fractionated through TSKgel ODS-80Ts column by a modification of the method described in EXAMPLE 16 (FIG. 10). In mass spectrometry of the fraction eluted at 31.681 minutes by a modification of the method described in EXAMPLE 16, the found molecular weight coincided with the calculated molecular weight of the polypeptide ((16–42)/(110–133)) composed of the B chain having the amino acid sequence shown by SEQ ID NO:8 and the A chain having the amino acid sequence shown by SEQ ID NO:7, i.e., the human novel polypeptide (mass spectrometry: Found: 5500.3, Calcd.: 5500.4). This fraction was further subjected to amino acid sequencing and mass spectrometry of 2 peptides formed after reduction. As a result, the amino acid sequencing of this fraction gave a mixed sequence of the B chain N-terminal sequence ArgAlaProTyr (N-terminal (1–5) partial sequence of SEQ ID NO:8) and the A chain N-terminal sequence AspValLeuAlaGly (N-terminal (1–5) partial sequence of SEQ ID NO:7). Also, the molecular weight found by mass spectrometry of the 2 peptides formed after reduction of this fraction coincided with the calculated molecular weight (mass spectrometry: Found: 3043.1, Calcd.: 3042.6) of the B chain having the amino acid sequence shown by SEQ ID NO:8 and with the calculated molecular weight (mass spectrometry: Found: 2463.1, Calcd.: 2463.8) of the A chain having the amino acid sequence shown by SEQ ID NO:7.

The foregoing results revealed that by treating (16–53)/(110–133) with trypsin and CPB, the polypeptide ((16–42)/(110–133)) composed of the B chain having the amino acid sequence shown by SEQ ID NO:8 and the A chain having the amino acid sequence shown by SEQ ID NO:7, i.e., the human novel polypeptide was obtained.

Furthermore, the polypeptide (16–41)/(110–133) composed of the peptide devoid of one amino acid (Trp) from the N terminus of the B chain having the amino acid sequence shown by SEQ ID NO:8 employed EXAMPLE 22 later described and the A chain having the amino acid sequence shown by SEQ ID NO:7 was also obtained as the by-product in the process described above.

Example 22

Intracellular cAMP Production Promoting Activity of the Human Novel Polypeptide Prepared from Human Novel Polypeptide Fused Protein Expressing Recombinant *E. coli* and its Derivatives on the THP-1 Cells The effect of the intracellular cAMP production of the human novel polypeptide prepared from human novel polypeptide fused protein expressing recombinant *E. coli* and its derivatives on the THP-1 cells was examined by a modification of the method described in EXAMPLE 17. As to the derivatives, the polypeptide (16–41)/(110–133) was also examined, in addition to (16–53)/(110–133). As a result, the human novel polypeptide [polypeptide ((16–42)/(110–133))] (FIG. 11) and its derivatives (FIG. 12) all displayed the activity of increasing the intracellular cAMP production level dependently on the concentration.

When comparing the activity between the human novel polypeptide and the human novel polypeptide derivatives different in the B chain C-terminal sequence, the activity was stronger in the order of (16–53)/(110–133)>(16–42)/(110–133) (human novel polypeptide)>(16–41)/(110–133).

The results revealed that the B chain C terminal sequence was critical for the activity.

Example 23

Activity of Promoting the Expression of Matrix Metalloprotease-1 (MMP-1) and Vascular Endothelial Growth Factor (VEGF) Gene by the Human Novel Polypeptide in Normal Human Lung Fibroblast Cell Line CCD-19Lu (ATCC CCL-210)

Normal human lung fibroblast cell line CCD-19Lu was suspended in medium B (Minimum Essential Medium with Earle's Salts (GIBCO-BRL), 100 μM MEM Non-Essential Amino Acids (GIBCO-BRL), 10% FCS, 100 U/ml penicillin, 100 μg/ml streptomycin) in $10^6$ cells/ml. The cell suspension was dispensed by the aliquot of 2 ml each in a 6-well plate, followed by incubation at 37° C. in a 5% carbon dioxide gas incubator. When the cells reached the confluent state, the cells were rinsed twice with 2 ml of medium C (Minimum Essential Medium with Earle's Salts (GIBCO-BRL), 100 μM MEM Non-Essential Amino Acids (GIBCO-BRL), 100 U/ml penicillin, 100 μg/ml streptomycin, 0.025% CHAPS, 0.2% BSA), the medium C was added by the aliquot of 2 ml each, followed by incubation at 37° C. for further 24 hours in a 5% carbon dioxide gas incubator. The medium was removed by suction. After the medium C was added by the aliquot of 1 ml each, the human novel polypeptide solution, which was prepared to 2-fold concentration of the final concentration per well by the medium C, was added by the aliquot of 1 ml each, followed by incubation at 37° C. for 24 hours in a 5% carbon dioxide gas incubator. After all RNAs were extracted from the thus treated cells by a modification of the protocol recommended by the manufacturer using Trisol reagent (GIBCO-BRL), reverse transcription was carried out by a modification of the protocol attached to the kit, using TaKaRa RNA PCR Kit (AMV) Ver. 2.1 (Takara Shuzo Co., Ltd.) to synthesize cDNA. For measurement of the gene expression levels of MMP-1, VEGF and housekeeping gene or glyceroaldehyde-3-phosphate dehydrogenase (G3PDH) in the CCD-19Lu cell line, the reverse transcription reaction solution was used as a template DNA in all cases, and TaqMan PCR using ABI PRISM 7700 (Applied Biosystems) was carried out using TaqMan PCR Core Reagents Kit with AmpliTaq Gold (Applied Biosystems) in accordance with the protocol attached to the kit. When measuring the gene expression level of human MMP-1, the oligo DNAs shown by SEQ ID NO:70 and SEQ ID NO:71 were used as sense strand and antisense strand primers, respectively, and the oligo DNA shown by SEQ ID NO:72 bearing Fam as a reporter dye at the 5' end and Tamra as a quencher dye at the 3' end was used as the TaqMan probe. When measuring the gene expression level of human VEGF, the oligo DNAs shown by SEQ ID NO:73 and SEQ ID NO:74 were used as sense strand and antisense strand primers, respectively, and the oligo DNA shown by SEQ ID NO:75 bearing Fam as a reporter dye at the 5' end and Tamra as a quencher dye at the 3' end was used as the TaqMan probe. When measuring the gene expression level of human G3PDH, the oligo DNAs shown by SEQ ID NO:76 and SEQ ID NO:77 were used as sense strand and antisense strand primers, respectively, and the oligo DNA shown by SEQ ID NO:78 bearing Fam as a reporter dye at the 5' end and Tamra as a quencher dye at the 3' end was used as the TaqMan probe.

PCR was carried out by the program designed to first keep at 50° C. for 2 minutes and then repeat the cycle set to include 95° C. for 15 seconds and 60° C. for 1 minute 40 times.

As a result, the purified human novel polypeptide preparation increased the relative ratio of the gene expression level of MMP-1 and VEGF to that of G3PDH (FIG. 13). These results revealed that the purified human novel polypeptide preparation had the activity of promoting the MMP-1 and VEGF gene expression in the normal human lung fibroblast cell line CCD-19Lu.

Example 24

Activity of Promoting the Expression of Vascular Endothelial Growth Factor (VEGF) Gene by the Human Novel Polypeptide in THP-1 Cells Effect on the expression of vascular endothelial growth factor (VEGF) gene by the human novel polypeptide in THP-1 cells was examined by the following procedures.

First, THP-1 cells in the growth phase were suspended in 10% FCS-containing RPMI-1640 in a density of $5\times10^4$ cells/ml, and the aliquot of 0.4 ml each of the suspension was dispensed in a 24-well culture plate. Next, a dilution of the purified human novel polypeptide preparation (having the same lot as in EXAMPLE 21) with the same medium to a given concentration was added to each well by the aliquot of 0.1 ml each. After thoroughly mixing them, the cells were incubated in the same culture plate at 37° C. for 24 hours. After the total RNAs were immediately recovered from the respective cells thus treated, using RNeasy Mini Kit (Qiagen), reverse transcription was performed using THERMOSCRIPT™ RT-PCR (Lifetech Oriental) to synthesize cDNA for a start. The gene expression was quantified by performing TaqMan™ PCR (Applied Biosystems) using the cDNA as a template DNA in accordance with a modification of the method described in EXAMPLE 23 and detecting the target specific signal formed with ABI PRISM™ 7700 Sequence Detection Systems (Applied Biosystems).

As shown in FIG. 16, the results revealed that the purified human novel polypeptide preparation had the activity of increasing the relative ratio of the VEGF gene expression level to the G3PDH gene expression level to promote the expression of the VEGF gene.

Example 25

Activity of Promoting cAMP Production of the Purified Human Novel Polypeptide Preparation on Human Normal Skin Fibroblast Cell Line NHDF Cells Human normal skin fibroblast cell line NHDF cells (BioWhittaker) were suspended in medium D (fibroblast medium kit (BioWhittaker)) in $10^5$ cells/ml. The cell suspension was dispensed by the aliquot of 1 ml each in a 24-well plate, followed by incubation at 37° C. in a 5% carbon dioxide gas incubator for 2 days. The cells were rinsed twice with 1 ml of the medium A described in EXAMPLE 17 and 0.4 ml of the medium A was added, followed by incubation at 37° C. for an hour in a 5% carbon dioxide gas incubator. After 50 μl of the purified human novel polypeptide preparation solution, which was prepared to a 10-fold concentration of the final concentration upon the reaction with the buffer A described in EXAMPLE 17, and 50 μl of 10 μM forskolin (Wako Pure Chemical Industries, Ltd.) solution were added to the cell suspension supra, the mixture was incubated at 37° C. for 30 minutes in a 5% carbon dioxide gas incubator. The cells were rinsed twice with 1 ml of the medium A. After adding 0.5 ml of the medium A to the cells, 100 μl of 20% perchloric acid solution thereto, which was then allowed to stand at 4° C. for 20 minutes. The cell extract was transferred to a microtube of 1.5 ml volume followed by centrifugation (15,000 rpm, 10 minutes, 4° C.). After 500 μl of the supernatant was transferred to another microtube of 1.5 ml volume, 60 mM HEPES and 1.5 M KOH solution were added for neutralization. The neutralized one was used as a sample for cAMP assay. The intracellular cAMP level was assayed using cAMP EIA System (Amersham Pharmacia) by a modification of the protocol attached to the kit.

As a result, the purified human novel polypeptide preparation displayed the activity of increasing the intracellular cAMP level on the NHDF cells dependently on the concentration (FIG. 14).

Example 26

Activity of Promoting cAMP Production of the Purified Human Novel Polypeptide Preparation on Rat Anterior Pituitary Primary Culture Cells The anterior pituitaries were excised from the decapitated skull of 32 unanesthetized Wistar rats (8 weeks old, male). The anterior pituitaries were placed in a laboratory dish containing the buffer B (137 mM sodium chloride, 5 mM potassium chloride, 0.7 mM disodium hydrogenphosphate, 25 mM HEPES (pH 7.3), and 50 μg/ml of gentamycin sulfate) and washed once with the buffer B. Each anterior pituitary was cut into 4 pieces by scissors and washed twice again. The pieces of the anterior pituitaries were incubated in 30 ml of Enzyme Solution I (buffer B containing 0.4% collagenase A (Boehringer Mannheim), 0.4% bovine serum albumin, 10 μg/ml of deoxyribonuclease I (Sigma) and 0.2% of glucose) at 37° C. for an hour, while shaking. After the tissue pieces were dispersed with a Komagome pipette, the dispersion was centrifuged (480×g, 6 minutes) and the supernatant was discarded. The sediment was suspended in 30 ml of Enzyme Solution II (buffer B containing 0.25% pancreatin (Sigma)) and incubated at 37° C. for 8 minutes while shaking. After adding 2 ml of fetal calf serum, the cell suspension was centrifuged (480×g, 6 minutes) again and the supernatant was discarded. The sediment was suspended in 10 ml of the medium D (Dulbecco modified Eagle's Medium (DMEM) containing 10% fetal calf serum, 20 mM HEPES (pH 7.3), 50 U/ml of penicillin G and 50 μg/ml of streptomycin) and filtered through a nylon mesh. The cells were further washed twice with 10 ml of the medium D. The count of the cells was counted, and the cells were suspended in the medium D in the cell density of $1.8\times10^5$ cells/ml. After 1 ml each of the cell suspension was dispensed in each well of a 24-well plate, the suspension was incubated at 37° C. for 3 days in a 5% carbon dioxide gas incubator. The cells were washed twice with 1 ml of the medium E (the medium A described in EXAMPLE 17, in which the IBMX concentration was made 1 mM) and 0.45 ml of the medium E was added to the cells, followed by incubation at 37° C. for an hour in a 5% carbon dioxide gas incubator. After 50 μl of the purified human novel polypeptide preparation solution, which was prepared to a 10-fold concentration of the final concentration upon the reaction with the buffer A described in EXAMPLE 17, was added to the cell suspension supra, the mixture was incubated at 37° C. for 30 minutes in a 5% carbon dioxide gas incubator. The cells were rinsed twice with 1 ml of the medium E. After adding 0.5 ml of the medium E to the cells, 100 μl of 20% perchloric acid solution thereto, which was then allowed to stand at 4° C. for 20 minutes. The cell extract was transferred to a microtube of 1.5 ml volume followed by centrifugation (15,000 rpm, 10 minutes, 4° C.). After 500 μl of the supernatant was transferred to another microtube of 1.5 ml volume, 60 mM HEPES and 1.5 M KOH solution were added for neutralization. The neutralized one was used as a sample for cAMP assay. The intracellular cAMP level was assayed using cAMP EIA System (Amersham Pharmacia) by a modification of the protocol attached to the kit.

As a result, the purified human novel polypeptide preparation displayed the activity of increasing the intracellular cAMP level on the rat anterior pituitary primary culture cells dependently on the concentration (FIG. 15).

Example 27

Activity of Promoting cAMP Production of the Purified Human Novel Polypeptide Preparation on Mouse Pulmonary Alveolar Macrophage Mouse pulmonary alveolar macrophage was obtained by recovering alveolar lavage fluids from BALB/C mouse (female, 8 weeks old) under anesthesia with Nembutal (Dainippon Pharmaceutical Co., Ltd.) using Hank's solution (Lifetech Oriental) in accordance with a publicly known method. The alveolar macrophage cells were seeded on a 24-well culture plate in a density of $5\times10^4$ cells/well and subjected to stationary culture in 10% FCS-containing RPMI-1640 medium at 37° C. for 2 hours to adhere the cells to the bottom surface of the culture plate. Next, RPMI-1640 medium containing 10% FCS and 50 μM IBMX was replaced for the medium. After the purified human novel polypeptide preparation solution (which was separately purified from the novel precursor (human type) expressing AtT20 cells by the method described in EXAMPLE 16 and dissolved in the buffer A described in EXAMPLE 17 in a concentration of 5.0 μM) was added to a final concentration of 100 nM, the cells were subjected to stationary culture at 37° C. for further 45 minutes. The intracellular cAMP level of the thus treated cells was assayed using cAMP EIA System (Amersham Pharmacia) by a modification of the protocol attached to the kit.

As a result, it was perceived that the mouse pulmonary alveolar macrophage added with the purified human novel polypeptide preparation increased the intracellular cAMP level by about 1.4 times, as compared to the control group without the addition of the preparation.

Example 28

Determination of the Class and Subclass of the Mouse Monoclonal Antibody HK4-144-10

The class and subclass of the mouse monoclonal antibody HK4-144-10 described in EXAMPLE 15 supra were identified to be IgGI and K, by EIA using commercially available antisera (manufactured by Bio-Rad).

Example 29

Construction of the Animal Cell Expression Vector for the Human Novel Polypeptide Gene The expression vector for expressing the human novel polypeptide gene in COS-7 cells was constructed. Because of failure to express the processing enzyme PC1 necessary for processing the polypeptide precursor in COS-7 cells, the PC1 processing recognition sequence (Arg-Xaa-Xaa-Arg) was replaced with the sequence (Arg-Xaa-Arg-Xaa-Arg-Arg) that was recognized and processed by processing enzyme furin, and an expression plasmid capable of simultaneously expressing human furin was further constructed. In this case, the part corresponding to the C-terminal transmembrane domain was removed so as to be able to obtain the furin expression product as a secretory protein. Furthermore for easy detection, His-tag sequence composed of 6 amino acid residues was introduced into the C-terminal side.

In order to produce human furin cDNA, using as a template human pancreas cDNA (Clontech) and further using the synthetic DNA (SEQ ID NO:79) corresponding to the translation initiation site of human furin protein, the synthetic DNA (SEQ ID NO:80) designed to contain the amino acid sequence up to $^{595}$Ala of furin protein, His-His-His-His-His-His sequence and then termination codon, PCR (reaction conditions: 94° C. for 1 min.→(98° C. for 10 secs.→68° C. for 3 mins. and 30 secs.)×25 cycles→72° C. for 10 mins→4° C.) was carried out to give the DNA fragment. After digesting this DNA fragment with restriction enzyme BlnI (Takara Shuzo Co., Ltd.), the digestion product was introduced into pCAN618 at the BlnI site to construct secretory furin/His-tag expression plasmid for a start.

Next, using as a template the cDNA fragment encoding the human novel polypeptide gene and further using the synthetic DNA (SEQ ID NO:81) designed to have the MfeI restriction enzyme site immediately before ATG of the translation initiation codon, the synthetic DNA (SEQ ID NO:82) designed to have the sequence encoding the C terminus of the human novel polypeptide gene and then termination codon, and Pfu DNA polymerase (Stratagene), PCR (reaction conditions: 95° C. for 1 min.→(98° C. for 10 secs.→68° C. for 35 secs.)×25 cycles→72° C. for 5 mins→4° C.) was carried out. Thus, the DNA fragment containing ORF of the human novel polypeptide gene and with the amino acid substitution of $^{113}$Val→$^{113}$Arg and $^{117}$Ser→$^{117}$Arg was obtained. After digesting this DNA fragment with restriction enzyme MfeI (New England Biolabs), the digestion product was introduced into the secretory furin/His-tag expression plasmid obtained supra at the EcoRI site and the blunt end NotI site to give human novel polypeptide precursor/furin-His-tag co-expression vector pCAN618/hVH13 containing, before the A chain, the sequence (Arg-Leu-Arg-Gly-Arg-Arg) recognition-processed by furin.

At the same time, human novel polypeptide precursor protein/furin-His-tag co-expression vector without any amino acid substitution was similarly constructed for control.

Using as a template the cDNA fragment encoding the human novel polypeptide gene and further using the synthetic DNA (SEQ ID NO:81) designed to have the MfeI restriction enzyme site immediately before ATG of the translation initiation codon, the synthetic DNA (SEQ ID NO:83) designed to contain the sequence encoding the C terminus of the human novel polypeptide gene and then termination codon NotI restriction enzyme site, and Pfu DNA polymerase (Stratagene), PCR (reaction conditions: 95° C. for 1 min.→(98° C. for 10 secs.→68° C. for 35 secs.)×25 cycles→72° C. for 5 mins→4° C.) was carried out. Thus, the DNA fragment containing ORF of the human polypeptide precursor was obtained. After double digestion with restriction enzymes MfeI (New England Biolabs) and NotI (New England Biolabs) was applied to this DNA fragment, the digestion product was introduced into the secretory furin/His-tag expression plasmid obtained above at the EcoRI and NotI sites to give human polypeptide precursor/furin-His-tag co-expression vector pCAN618/hVH1,4.

Example 30

Construction of the Animal Cell Expression Vector for the Mouse Novel Polypeptide Gene The expression vector for expressing the mouse novel polypeptide gene in COS-7 cells was constructed by the procedures similar to those of EXAMPLE 29 above.

First, using as a template the cDNA fragment encoding the mouse novel polypeptide gene and further using the synthetic DNA (SEQ ID NO:84) designed to have the EcoRI restriction enzyme site immediately before ATG of the translation initiation codon, the synthetic DNA (SEQ ID NO:85) designed to have the sequence encoding the C terminus of the mouse novel polypeptide gene and then the termination codon NotI restriction enzyme site, and Pfu DNA polymerase (Stratagene), PCR (reaction conditions: 95° C. for 1 min.→(98° C. for 10 secs.→68° C. for 35 secs.)×25 cycles→72° C. for 5 mins→4° C.) was carried out to give the DNA fragment containing ORF of the mouse novel polypeptide precursor and with the amino acid substitution of $^{112}$Val→$^{112}$Arg and $^{116}$Ser→$^{116}$Arg. After double digesting this DNA fragment with restriction enzymes EcoRI and NotI (New England Biolabs), the digestion product was introduced into the secretory furin/His-tag expression plasmid obtained in EXAMPLE 29 supra at the EcoRI and NotI sites. Thus, the mouse polypeptide precursor/furin-His-tag co-expression vector pCAN618/mVH1,3 containing before the A chain the sequence (RVRGRR) recognition-processed by furin, was obtained.

At the same time, the mouse polypeptide precursor protein/furin-His-tag co-expression vector without any amino acid substitution was similarly constructed for control.

Using as a template the cDNA fragment encoding the mouse novel polypeptide gene and further using the synthetic DNA (SEQ ID NO:84) designed to have the EcoRI restriction enzyme site immediately before ATG of the translation initiation codon, the synthetic DNA (SEQ ID NO:86) designed to contain the sequence encoding the C terminus of the mouse novel polypeptide gene and then termination codon NotI restriction enzyme site, and Pfu DNA polymerase (Stratagene), PCR (reaction conditions: 95° C. for 1 min.→(98° C. for 10 secs.→68° C. for 35 secs.)×25 cycles→72° C. for 5 mins <4° C.) was carried out. Thus, the DNA fragment containing ORF of the polypeptide precursor was obtained. After double digesting this DNA fragment with restriction enzymes EcoRI and NotI (New England Biolabs), the digestion product was introduced into the secretory furin/His-tag expression plasmid obtained in EXAMPLE 29 supra at the EcoRI and NotI sites to give the mouse polypeptide precursor/furin-His-tag co-expression vector pCAN618/mVH1,2.

Example 31

Expression and Secretion of the Novel Mature Polypeptide in the COS-7 Culture Supernatant In order to confirm expression and secretion of the novel mature polypeptide in the culture supernatant, the human polypeptide precursor expression vector produced in EXAMPLES 29 and 30 supra was transfected to COS-7 cells and the mature peptide in the culture supernatant was assayed by EIA. On the day before transfection, the expression vector produced in EXAMPLE 29 supra was plated on a 6-well plate in $4\times10^5$ cells/well, followed by incubation in 10% FBS (Hyclone)-containing DMEM medium (Gibco-BRL) for 24 hours in a $CO_2$ incubator. Twenty-four hours after the transfection effected using the expression vector produced in EXAMPLE 29 supra, pCAN618 and FuGENE6 (Roche Diagnostics), DMEM (Phenol Red) medium (Gibco-BRL) containing 1 ml of 0.1 mM 4-(2-aminoethylbenzene-sulfonyl fluoride (pABSF) (Wako Pure Chemical Industries, Ltd.) and 0.05% CHAPS (Dojin Kagaku) was replaced for the medium. Incubation was continued for further 48 hours. The culture supernatant was transferred to an Eppendorf sample tube and centrifuged to remove the floating cells. This stock solution was used directly for the EIA assay. EIA was conducted by a modification of the competitive method described in EXAMPLE 16 (FIG. 17).

The results revealed that about 35 nM of the immunoreactive polypeptide was present in the culture supernatant of COS-7 cells transfected by the human polypeptide precursor/furin-His-tag co-expression vector pCAN618/hVH1,3 containing, before the A chain, the sequence (RLRGRR) recognition-processed by furin and that about 41 nM of the immuno-reactive polypeptide was present in the culture supernatant of COS-7 cells transfected by the mouse polypeptide precursor/furin-His-tag co-expression vector pCAN618/mVH1,3.

Example 32

Activity of Promoting the Intracellular cAMP Production of the Novel Polypeptide Present in the COS-7 Culture Supernatant on THP-1 Cells It was confirmed in EXAMPLE 31 that the immunoreactive human polypeptide was expressed and secretedin the culture supernatant of COS-7 cells. In order to verify this biological activity, the intracellular cAMP production promoting activity on THP-1 cells was examined by the method shown in EXAMPLE 17, using the stock solution of the culture supernatant (FIG. 18).

The results revealed that when the culture supernatant of COS-7 cells transfected by the human polypeptide precursor/furin-His-tag co-expression vector pCAN618/hVH1,3 containing, before the A chain, the sequence (RLRGRR) recognition-processed by furin was added, the intracellular cAMP production promoting activity on THP-1 cells increased by about 1.8 times, and when the culture supernatant of COS-7 cells transfected by the mouse polypeptide precursor/furin-His-tag co-expression vector pCAN618/mVH1,3 was added, the intracellular cAMP production promoting activity on THP-1 cells increased by about 1.6 times, indicating that the novel polypeptides having the biological activity were produced.

INDUSTRIAL APPLICABILITY

The polypeptide of the present invention and the DNA encoding the same can be used for the diagnosis, treatment or prevention of various diseases such as abnormalities (e.g., diabetes mellitus, etc.) in metabolic regulation (sugar metabolism, lipid metabolism, etc.) of energy sources such as carbohydrates; inhibition of growth/proliferation/differentiation of tissues; hypogonadism; dysplasia of connective tissues (e.g., scleroderma, etc.), fibrillation of tissues (e.g., liver cirrhosis/pulmonary fibrosis, scleroderma, renal fibrosis, etc.); circulatory disorders (peripheral arterial diseases, cardiac infarction or cardiac failure, etc.), endocrine disruption, abnormality of body fluid balance, central diseases, immune system diseases such as allergy, etc., angiogenic disorders, or the like. The polypeptide of the present invention is also useful as a reagent for screening compounds or salts thereof that promote or inhibit the activity of the polypeptide of the present invention. The antibody to the polypeptide of the present invention is capable of specifically recognizing the polypeptide of the present invention and can thus be used for the detection, quantification, neutralization, etc. of the polypeptide of the present invention in a test fluid.

The invention claimed is:

1. An isolated polypeptide having the amino acid sequence represented by SEQ ID NO:7, its amide or ester, or a salt thereof or the amino acid sequence represented by SEQ ID NO:8, its amide or ester, or a salt thereof.

2. An isolated polypeptide or its amide or ester, or a salt thereof according to claim 1 which contains a first amino acid segment comprising the amino acid sequence represented by SEQ ID NO:7, and a second amino acid segment comprising the amino acid sequence represented by SEQ ID NO:8.

3. An isolated polypeptide or its amide or ester, or a salt thereof, of claim 2, wherein the first amino acid segment and die second amino acid segment are bonded together through disulfide bonds.

4. An isolated polypeptide or its amide or ester, or a salt thereof, according to claim 1, comprising the amino acid sequence represented by SEQ ID NO:3.

5. A method of screening a compound that promotes or inhibits the activity of a polypeptide or its amide or ester, or a salt thereof, according to claim 1 which comprises comparing (i) the binding when a polypeptide of claim 1 is brought into contact with tissues, cells or membrane fractions thereof, to:

(ii) the binding when a polypeptide of claim 1 is brought into contact with tissues, cells or membrane fractions thereof, in the presence of a test compound, and (iii) determining if the binding of said isolated polypeptide to the said tissues, cells or membrane fractions is increased or inhibited by the test compound.

6. A kit for screening a compound or its salt that promotes or inhibits the activity of a polypeptide or its amide or ester, or a salt thereof according to claim 1, comprising a polypeptide or its amide or ester, or a salt thereof, according to claim 1.

7. A pharmaceutical composition comprising a polypeptide, its amide or ester, or a salt thereof, according to claim 1 and a pharmaceutically acceptable carrier, diluent or excipient.

8. A method for making a pharmaceutical for preventing or treating abnormality of metabolic regulation inhibition of growth/proliferation/differentiation of tissue, hypogonadism, dysplasia of connective tissue, fibrillation of tissue, circulatory disorders, endocrine disruption, abnormality of body fluid balance, central disease, immune system disease or angiogenic disorder, comprising combining an effective amount of a polypeptide comprising the amino acid sequence represented by SEQ ID NO:7, or the amino acid sequence represented by SEQ ID NO:8, its amide or ester, or a salt thereof, with a pharmaceutically acceptable carrier, diluent or excipient.

9. A method of screening a compound that promotes or inhibits the activity of a polypeptide or its amide or ester, or a salt thereof, according to claim 2 which comprises comparing (i) the binding when a polypeptide of claim 2 is brought into contact with tissues, cells or membrane fractions thereof, to (ii) the binding when a polypeptide of claim 2 is brought into contact with tissues, cells or membrane fractions thereof, in the presence of a test compound, and (iii) determining if the binding of said isolated polypeptide to the said tissues, cells or membrane fractions is increased or inhibited by the test compound.

10. A kit for screening a compound or its salt that promotes or inhibits the activity of a polypeptide or its amide or ester, or a salt thereof; according to claim 2, comprising a polypeptide or its amide or ester, or a salt thereof; according to claim 2.

11. A pharmaceutical composition comprising a polypeptide, its amide or ester, or a salt thereof, according to claim 2 and a pharmaceutically acceptable carrier, diluent or excipient.

12. The method of claim 8 wherein a polypeptide having the amino acid sequence represented by SEQ ID NO:7, and a polypeptide having the amino acid sequence represented by SEQ ID NO:8 are joined.

13. A method of screening a compound that promotes or inhibits the activity of a polypeptide or its amide or ester, or a salt thereof, according to claim 4 which comprises comparing (i) the binding when a polypeptide of claim 4 is brought into contact with tissues, cells or membrane fractions thereof, to (ii) the binding when a polypeptide of claim 4 is brought into contact with tissues, cells or membrane fractions thereof, in the presence of a test compound, and (iii) determining if the binding of said isolated polypeptide to the said tissues, cells or membrane fractions is increased or inhibited by the test compound.

14. A kit for screening a compound or its salt that promotes or inhibits the activity of a polypeptide or its amide or ester, or a salt thereof, according to claim 4, comprising a polypeptide or its amble or ester, or a salt thereof; according to claim 4.

15. A pharmaceutical composition comprising a polypeptide, its amide or ester, or a salt thereof, according to claim 4 and a pharmaceutically acceptable carrier, diluent or excipient.

* * * * *